US007829102B2

(12) United States Patent
Buchholz et al.

(10) Patent No.: US 7,829,102 B2
(45) Date of Patent: *Nov. 9, 2010

(54) PRODUCTION OF ATTENUATED, HUMAN-BOVINE CHIMERIC RESPIRATORY SYNCYTIAL VIRUS VACCINES

(75) Inventors: Ursula Buchholz, Silver Spring, MD (US); Peter L. Collins, Silver Spring, MD (US); Brian R. Murphy, Bethesda, MD (US); Stephen S. Whitehead, Montgomery Village, MD (US); Christine D. Krempl, Wuerzburg (DE)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 670 days.

This patent is subject to a terminal disclaimer.

(21) Appl. No.: 11/097,946

(22) Filed: Mar. 31, 2005

(65) Prior Publication Data

US 2006/0057158 A1 Mar. 16, 2006

Related U.S. Application Data

(63) Continuation of application No. 09/602,212, filed on Jun. 23, 2000, now abandoned.

(60) Provisional application No. 60/143,132, filed on Jul. 9, 1999.

(51) Int. Cl.
*A61K 39/155* (2006.01)

(52) U.S. Cl. ............... 424/211.1; 424/199.1; 424/202.1

(58) Field of Classification Search ........................ None
See application file for complete search history.

(56) References Cited

U.S. PATENT DOCUMENTS

| 4,683,195 | A | 7/1987 | Mullis et al. |
|---|---|---|---|
| 4,683,202 | A | 7/1987 | Mullis |
| 4,800,078 | A | 1/1989 | Prince et al. |
| 5,716,821 | A | 2/1998 | Wertz et al. |
| 5,789,229 | A | 8/1998 | Wertz et al. |
| 5,869,036 | A | 2/1999 | Belshe et al. |
| 5,882,651 | A | 3/1999 | Murphy et al. |
| 5,922,326 | A | 7/1999 | Murphy et al. |
| 5,993,824 | A | 11/1999 | Murphy et al. |
| 6,033,886 | A | 3/2000 | Conzelmann |
| 6,264,957 | B1 | 7/2001 | Collins |
| 6,689,367 | B1 | 2/2004 | Collins et al. |
| 6,699,476 | B1 | 3/2004 | Collins et al. |
| 6,713,066 | B1 | 3/2004 | Collins et al. |
| 7,465,794 | B2 | 12/2008 | Collins |
| 2002/0146433 | A1 | 10/2002 | Krempl et al. |

FOREIGN PATENT DOCUMENTS

| EP | 0 440 219 A1 | 8/1991 |
|---|---|---|
| EP | 0 702 085 A1 | 3/1996 |
| WO | WO-93 14207 | 7/1993 |
| WO | WO-93 21310 | 10/1993 |
| WO | WO-94 17105 | 8/1994 |
| WO | WO-97 06270 | 2/1997 |
| WO | WO-97 11093 | 3/1997 |
| WO | WO 97/12032 A1 * | 4/1997 |
| WO | WO-97 12032 A1 | 4/1997 |
| WO | WO-97 20468 | 6/1997 |
| WO | WO-98 02530 | 1/1998 |
| WO | WO-98 43668 | 10/1998 |
| WO | WO-98 53078 | 11/1998 |
| WO | WO-99 02657 | 1/1999 |
| WO | WO-99 15631 | 4/1999 |
| WO | WO-99 24564 | 5/1999 |
| WO | WO-00 61611 | 10/2000 |
| WO | WO-00 61737 | 10/2000 |
| WO | WO-01 04271 | 1/2001 |
| WO | WO-01 04321 | 1/2001 |

OTHER PUBLICATIONS

Collins et al. PNAS USA, 1995, 92:11563-11567.*
Tang et al. J. Virology, 2001, 75(23):11328-11335.*
Ahmadian et al., Expression Of The ORF-2 Protein Of The Human Respiratory Syncytial Virus M2 Gene, EMBO J vol. 19 2681-2689 (2000).
Anderson, Larry J., Antigenic Characterization of Respiratory Syncytial Virus Strains With Monoclonal Antibodies, Journal Infectious Diseases, vol. 151, No. 4, 626-633 (1985).

(Continued)

*Primary Examiner*—Stacy B Chen
(74) *Attorney, Agent, or Firm*—Woodcock Washburn LLP

(57) ABSTRACT

Chimeric human-bovine respiratory syncytial virus (RSV) are infectious and attenuated in humans and other mammals and useful in vaccine formulations for eliciting an anti-RSV immune response. Also provided are isolated polynucleotide molecules and vectors incorporating a chimeric RSV genome or antigenome which includes a partial or complete human or bovine RSV "background" genome or antigenome combined or integrated with one or more heterologous gene(s) or genome segment(s) of a different RSV strain. Chimeric human-bovine RSV of the invention include a partial or complete "background" RSV genome or antigenome derived from or patterned after a human or bovine RSV strain or subgroup virus combined with one or more heterologous gene(s) or genome segment(s) of a different RSV strain or subgroup virus to form the human-bovine chimeric RSV genome or antigenome.

7 Claims, 17 Drawing Sheets

OTHER PUBLICATIONS

Atreya et al., The NS1 Protein Of Human Respiratory Syncytial Virus Is A Potent Inhibitor Of Minigenome Transcription And RNA Replication, J. Virol. vol. 72 1452-1461 (1998).

Bailly et al., A Recombinant Human Parainfluenza Virus Type 3 (PIV3) In Which the Nucleocapsid N Protein Has Been Replaced, Journal Virology, vol. 74, No. 7, 3188-3195 (2000).

Baron et al., Rescue of Rinderpest Virus From Cloned cDNA, Journal Virology, vol. 71, No. 2, 1265-1271 (1997).

Belshe et al., Evaluation of Five Temperature-Sensitive Mutants of Respiratory Syncytial virus In Primates, Journal Medical Virology, vol. 3, 101-110 (1978).

Belshe et al., Experimental Respiratory Syncytial Virus Infection of Four Species of Primates, Journal Medical Virology, vol. 1, 157-162 (1977).

Bermingham et al., The M2-2 Protein of Human Respiratory Syncytial Virus, Proc. Natl. Acad. Sci., vol. 96 11259-11264 (1999).

Buchholz, Ursula J., Chimeric Bovine Respiratory Syncytial Virus With Glycoprotein Gene Substitutions, Journal Virology, vol. 74, No. 3, 1187-1199 (2000).

Buchholz, Ursula J., Generation of Bovine Respiratory Syncytial Virus (BRSV) from cDNA, Journal Virology, vol. 73, No. 1, 251-259 (1999).

Bukreyev, Alexander, Interferon Gamma Expressed By A Recombinant Respiratory Syncytial Virus, Proc. Natl. Acad. Sci., vol. 96 2367-2372 (1999).

Bukreyev, Alexander, Recombinant Respiratory Syncytial Virus From Which Entire SH Gene Deleted Grows In Cell Culture, Journal Virology, vol. 71, No. 12, 8973-8982 (1997).

Bukreyev, Alexander, Recovery of Infectious Respiratory Syncytial Virus Expressing An Additional, Foreign Gene, Journal Virology, vol. 70, No. 10, 6634-6641 (1996).

Cahour et al., Growth-Restricted Dengue Virus Mutants Containing Deletions In The 5 Noncoding Region Of The RNA Genome, Virology vol. 207 68-76 (1995).

Cheng et al., Effective Amplification of Long Targets From Cloned Inserts and Human Genomic DNA, Proc. Natl. Acad. Sci. USA, vol. 91, 5695-5699 (1994).

Chin et al., Field Evaluation Of A Respiratory Syncytial Virus Vaccine And A Trivalet Parainfluenza Virus Vaccine In A Pediatric Population, Am. J. Epidemiol. vol. 89 449-463 (1968).

Clements et al., Evaluation of Bovine Cold-Adapted Human, and Wild-Type Human Parainfluenza Type 3 Viruses in Adult Volunteers, J. Clinical Microbiology, vol. 29, 1175-1182 (1991).

Collins et al., Envelope-Associated 22K Protein of Human Respiratory Syncytial Virus, Journal Virology, vol. 54, No. 1, 65-71 (1985).

Collins et al., Evaluation In Chimpanzees of Vaccinia Virus Recombinants That express The Surface, Vaccine vol. 8 164-168 (1990).

Collins et al., Gene Overlap And Site Specific Atenuation Of Transcription, Proc. Natl. Acad. Sci. USA vol. 84 5134-5138 (1987).

Collins et al., Nucleotide Sequences For The Gene Junction Of Human Respiratory Syncytial Virus Reveal, Proc. Natl. Acad. Sci. USA vol. 83 4594-4598 (1986).

Collins et al., Production of Infectious Human Respiratory Syncytial Virus From Cloned cDNA, Pro. Natl. Acad. Sci., vol. 92, 11563-11567 (1995).

Collins et al., Rational Design Of Live Attenuated Recombinant Vaccine Virus For Human Respiratory Syncytial Virus By Reverse Genetics, Adv. Virus Res. vol. 54 423-451 (1999).

Collins et al., Respiratory Syncytial Virus, Fields Virology, 2nd Ed., 1313-1352, (1996).

Collins et al., Support Plasmids and Support Proteins Required for Recovery of Recombinant Respiratory Syncytial Virus, Virology, vol. 259, 251-255 (1999).

Collins et al., Transcription Elongation Of Respiratory Syncytial Virus A Nonsegmented Negative-Strand RNA Virus, Proc. Natl. Acad. Sci. USA vol. 93 81-85 (1996).

Collins et al., Two Open Reading Frames of 22K mRNA of Human Respiratory Syncytial Virus, Journal General Virology, vol. 71, 3015-3020 (1990).

Connors et al., A Cold Passaged Attenuated Strain of Human Respiratory Syncytial Virus Contains Mutations in the F and L Genes, Virology, vol. 208, 478-484 (1995).

Connors et al., Respiratory Syncytial Virus (RSV) F, G, M2 (22K), And N Proteins Each Induce Resistance To RSV Challenge, J. Virol. vol. 65(3) 1634-1637 (1991).

Connors, Mark, Resistance To Respiratory Syncytial Virus (RSV), Journal Virology, vol. 66, No. 2, 1277-1281 (1992).

Conzelmann, Karl-Klaus, Genetic Manipulation of Non-Segmented Negative-Strand RNA Viruses, Journal General Virology, vol. 77, 381-389 (1996).

Conzelmann, Karl-Klaus, Rescue of Synthetic Genomic RNA Analogs of Rabies Virus By Plasmid-Encoded Proteins, Journal Virology, vol. 68, No. 2, 713-719 (1994).

Corsaro et al., Enhancing The Efficiency Of DNA Mediated Gene Transfer In Mammalian Cells, Somatic Cell Genetics vol. 7 603-616 (1981).

Crowe et al., A Comparison In Chimpanzees of Immunogenic Efficacy of Live Attenuated Respiratory Syncytial Virus (RSV), Vaccine, vol. 11, Issue 14, 1395-1404 (1993).

Crowe et al., Satisfactorily Attenuated Protective Mutants Derived From Partially Attenuated Cold Passaged Respiratory Syncytial Virus, Vaccine, vol. 12, No. 8, 691-699 (1994).

Crowe, James E., A Further Attenuated Derivative of Cold-Passaged Temperature-Sensitive Mutant of Human Respiratory Syncytial Virus, Vaccine, vol. 12, No. 9, 783-790 (1994).

Crowe, James E., Acquisition of the ts Phenotype By Chemically Mutagenized Cold Passaged Human Respiratory Syncytial Virus Vaccine, Virus Genes, vol. 13-3, 269-273 (1996).

Delenda, Christophe, Normal Cellular Replication of Sendai Virus Without Trans-Frame, Nonstructural V Protein, Virology, vol. 228, 55-62 (1997).

Durbin et al., Recovery of Infections Human Parainfluenza Virus Type 3 from cDNA, Virology, vol. 235, 323-332 (1997).

Emerson, Suzanne U., A Simian Strain of Hepatitis A Virus, AGM-27, Functions As An Attenuated Vaccine for Chimpanzees, Journal Infectious Diseases, vol. 173, 592-597 (1996).

Falsey, et al., Respiratory Syncytial Virus And Influenza A Infections In The Hospitalized Elderly, J. Infect. Dis. vol. 172 389-394 (1995).

Fernie & Gerin, The Stabilization And Purification Of Respiratory Syncytial Virus Using MgSO4, Virology vol. 106 141-144 (1980).

Friedewald et al., Low-Temperature-Grown RS Virus In Adult Volunteers, J. Amer. Med. Assoc. vol. 204 690-694 (1968).

Fouillard et al., Severe Respiratory Syncytial Virus Pneumonia After Autologous Bone Marrow Transplantation: A Report Of Three Cases Review, Bone Marrow Transplant vol. 9 97-100 (1992).

Furze et al., Antigenic Heterogeneity Of The Attachment Protein Of Bovine Respiratory Syncytial Virus, J. Gen. Virol. vol. 75 363-370 (1994).

Garcia-Barreno et al., Marked Differences In The Antigenic Structure Of Human Respiratory Syncytial Virus F and G Glycoproteins, J. Virol. vol. 63 No. 925-932 (1989).

Garcin et al., A Highly Recombinogenic System For Recovery of Infectious Sendai Paramyxovirus For cDNA, EMBO Journal, vol. 14, No. 24 6087-6094 (1995).

Gharpure et al., al., Temperature-Sensitive Mutants Of Respiratory Syncytial Virus, J. Virol. vol. 3 414-421 (1969).

Graham et al., A New Technique for The Assay of Infectivity of Human Adenovirus 5 DNA, Virology vol. 52 456 (1973).

Gromeier et al., Dual Stem Loops Within The Poliovirus Internal Ribosomal Entry Site Control Neurovirulence, J. Virol. vol. 73 958-964 (1999).

Groothuis, et al., Prophylactic Administration Of Respiratory Syncytial Virus Immune Globulin To High Risk Infants And Young Children, N. Engl. J. Med. vol. 329 1524-1530 (1993).

Grosfeld et al., RNA Replication By Respiratory Syncytial Virus (RSV) Is Directed By N, P, and L Proteins, Journal Virology, vol. 69, No. 9, 5677-5686 (1995).

Haas et al., Codon Usage Limitation In The Expression Of HIV-1 Envelope Glycoprotein, Current Biol. vol. 6 315-324 (1996).

Hawley-Nelson et al., A New Higher Efficiency Polycationic Liposome Transfection Reagent, Focus vol. 15 73-79 (1993).

He et al., Recovery of Infectious SV5 From Cloned DNA and Expression of A Foreign Gene, Virology, vol. 237, 249-260 (1997).

He, Biao, The Paramyxovirus SV5 Small Hydrophobic (SH) Protein Is Not Essential For Virus Growth In Tissue Culture Cells, Virology, vol. 250, 30-40 (1998).

Heilman et al., Respiratory Syncytial and Parainfluenza Virus, J. Infect. Dis. vol. 161 402-406 (1990).

Hendricks et al., Further Characterization of the Soluble Form of the G Glyoprotein of Respiratory Synsytial Virus, Journal Virology, vol. 62, No. 7, 2228-2233 (1988).

Hodes et al., Genetic Alteration In A Temperature Sensitive Mutant of Respiratory Syncytial Virus After Replication In Vivo (37972), Proc. Soc. Exp. Biol. Med. vol. 145 1158-1164 (1974).

Hoffman et al., An Infectious Clone of Human Parainfluenza Virus Type 3, Journal Virology, vol. 71, No. 6, 4272-4277 (1997).

Hurwitz, Julia L., Intranasal Sendai Virus Vaccine Protects African Green Monkeys From Infection With Human Parainfluenza Virus Type One, Vaccine, vol. 15, No. 5, 533-540 (1997).

Jin et al., Recombinant Human Respiratory Syncytial Virus (RSV) from cDNA and Construction of Subgroup A and B Chimeric RSV, Virology, vol. 251, 206-214 (1998).

Jin et al., Respiratory Syncytial Virus That Lacks Open Reading Frame 2 of the M2 Gene, Journal Virology, vol. 74, No. 1, 74-82 (2000).

Johnson, Philip R., Antigenic Relatedness Between Glycoproteins of Human Respiratory Syncytial Virus Subgroups A and B, Journal Virology, vol. 61, No. 10, 3163-3166 (1987).

Johnson, Philip R., The Fusion Glycoproteins of Human Respiratory Syncytial Virus of Subgroups A and B, Journal General Virology, vol. 69, 2623-2628 (1988).

Johnson, Philip R., The G Glycoprotein of Human Respiratory Syncytial Viruses of Subgroups A and B, Proc. Natl. Acad. Sci., vol. 84, 5625-5629 (1987).

Johnson and Collins, The 1B (NS2), 1C(NS1) And N Proteins Of Human Respiratory Syncytial Virus (RSV) Of Antigenic Subgroups A And B, J, Gen. Virol. vol. 70 1539-1547 (1989).

Johnson, Teresa R., Priming with Secreted Glycoprotein G of Respiratory Syncytial Virus (RSV) Augments Interleukin 5 Production, Journal Virology, vol. 72, No. 4, 2871-2880 (1998).

Juhasz et al., The Temperature Sensitive (ts) Phenotype of A Cold Passaged (cp) Live Attenuated Respiratory Syncytial Virus Vaccine Candidate, Journal Virology, vol. 71, No, 8, 5814-5819 (1997).

Juhasz et al., The Major Attenuating Mutations of the Respiratory Syncytial Virus Vaccine Candidate, J. Virol. vol. 73 5176-5180 (1999).

Juhasz et al., The Two Amino Acid Substitutions In The L Protein of cpts530 1009,Vaccine vol. 17 1416-1424 (1999).

Kapikian et al., An Epidemiologic Study Of Altered Clinical Reactivity To Respiratory Syncytial (RS) Virus, Am. J. Epidemiol. vol. 89 405-421 (1968).

Kapikian et al., Update On Jennerian And Modified Jennerian Approach To Vaccination Of Infants And Young Children, Adv. Exp. Med. Biol. vol. 327, 59-69 (1992).

Karron et al., Evaluation of Two Live cold Passaged Temperature Senstive Respiratory Syncytial Virus Vaccines in Chimpanzees and in Human, Journal Infectious Diseases, vol. 176, 1428-1436 (1997).

Karron et al., Respiratory Syncytial Virus (RSV) SH and G Proteins Are Not Essential For Viral Replication In Vitro, Proc. Natl. Acad. Sci., vol. 94, 13961-13966 (1997).

Karron, Ruth A., A Live Human Parainfluenza Type 3 Virus Vaccine Is attenuated and Immunogenic In Healthy Infants and Children, Journal Infectious Diseases, vol. 172, 1445-1450 (1995).

Kato et al., Initiation of Sendai Virus Multiplication From Transfected cDNA or RNA with Negative or Positive Sense, Genes To Cells, vol. 1, 569-579 (1996).

Kato, Atsushi, The Paramyxovirus Sendai Virus V Protein Encodes A Luxury Function Required For Viral Pathogenesis, EMBO Journal, vol. 16, No. 3, 578-587 (1997).

Kim et al., Safety and Antigenicity of Temperature Sensitive (TS) Mutant Respiratory Syncytial Virus (RSV) In Infants and Children, Pediatrics, vol. 52, No. 1, 56-62 (1973).

Kim et al, Respiratory Syncytial Virus Disease In Infants Despite Prior Administration of Antigenic Inactivated Vaccine, Am. J. Epidemiol. vol. 89 422-434 (1968).

Kretschmer et al., Normal Replication of Vesicular Stomatitis Virus Without C Proteins, Virology vol. 216 309-316 (1996).

Kunkel et al., Rapid and Efficient Site-Specific Mutagenesis Without Phenotypic Selection, Methods Enzymol 154 367-382 (1987).

Kuo et al., Effect of Mutations In Gene Start and Gene End Sequence Motifs On Transcription, Journal Virology, vol. 70, No. 10, 6892-6901 (1996).

Kurotani, Atsusi, Sendai Virus C Proteins Are Categorically Nonessential Gene Products, Genes To Cells, vol. 3, 111-124 (1998).

Langedijk et al., Antigenic Structure Of The Central Conserved Region Of Protein G Of Bovine Respiratory Syncytial Virus, J. Virol. vol. 71 4055-4061 (1997).

Latorre, Patrizia, The Various Sendai Virus C Proteins Are Not Functionally Equivalent, Journal Virology, vol. 72, No. 7, 5984-5993 (1998).

Lawson, Nathan D., Recombinant Vesicular Stomatitis Viruses From DNA, Proc. Natl. Acad. Sci., vol. 92, 4477-4481 (1995).

Lerch et al., Nucleotide Sequence Analysis and Expression from Recombinant Vectors, J. Virol. vol. 64 5559-5569 (1990).

Lerch et al., Nucleotide Sequence Analysis and Expression from Recombinant Vectors, Virology vol. 181 118-131 (1991).

Lopez et al., Antigenic Structure of Human Respiratory Syncytial Virus Fusion Glycoprotein, J. Virol. vol. 72 6922-6928 (1998).

Lopez et al., Nucleotide Sequence Of The Fusion And Phosphoprotein Genes Of Human Respiratory Syncytial (RS) Virus Long Strain: Evidence Of Subtype Genetic Heterogeneity, Virus Res. vol. 10 249-261 (1988).

Mallipeddi, Sanjay K., Sequence Comparison Between the Phosphoprotein mRNAs of Human and Bovine Respiratory Syncytial Viruses, Journal General Virology, vol. 73, 2441-2444 (1992).

Mallipeddi, Sanjay K., Sequence Variability of the Glycoprotein Gene of Bovine Respiratory Syncytial Virus, Journal General Virology, vol. 74, 2001-2004 (1993).

Mallipeddi et al., Structural Difference In The Fusion Protein Among Strains of Bovine Respiratory Syncytial Virus, Vet. Microbiol. vol. 36 359-367 (1993).

Martinez & Melero, Enhanced Neutralization Of Human Respiratory Syncytial Virus By Mixtures Of Monoclonal Antibodies To The Attachment (G) Glyoprotein, J. Gen. Virol. vol. 79 2215-2220 (1998).

Melero et al., Antigenic Structure Evolution and Immunobioloby of Human Respiratory Syncytial Virus Attachment (G) Protein, Journal General Virology, vol. 78, 2411-2418 (1997).

Men et al., Dengue Type 4 Virus Mutants Containing Deletions in the 3 Noncoding Region of the RNA, J. Virol. vol. 70 3930-3937 (1996).

McIntosh et al., Attenuated Respiratory Syncytial Virus Vaccines In Asthmatic Children, Pediatr. Res. vol. 8 689-696 (1974).

Mink et al., Nucleotide Sequences of the 3 Leader and 5 Trailer Regions of Human Respiratory Syncytial Virus Genomic RNA, Virology, vol. 185, 615-624 (1991).

Mohanty et al., Experimentally Induced Respiratory Syncytial Viral Infection In Calves, American Journal Vet. Res. vol. 36 417-419 (1975).

Mufson, Maurice A., Two Distinct Subtypes of Human Respiratory Syncytial Virus, Journal General Virology, vol. 66, 2111-2124 (1985).

Murphy et al., Enhanced Pulmonary Histopathology Is Observed In Cotton Rats Immunized, Vaccine, vol. 8, 497-502 (1990).

Murphy, Brian R., Current Approaches to the Development of Vaccines Effective Against Parainfluenza, Virus Research, vol. 11, 1-15 (1988).

Murphy et al., Production and Level of Genetic Stability of an Influenza A Virus Temperature Sensitive Mutant Containing Two Genes Infect. Immun., vol. 37, No. 1, 235-242 (1982).

Muster et al., An Influenza A Virus Containing Influenza B Virus 5' and 3' Noncoding, Proc. Natl. Acad. Sci. USA vol. 88 5177-5181 (1991).

Needleman and Wunsch, A General Method Applicable To The Search For Similarities In The Amino Acid Sequence Of Two Proteins, J. Mol. Biol. vol. 48 443 (1970).

Neumann et al., Gene Transfer Into Mouse Lymoa Cells By Electroporation In High Electric Fields EMBO J. vol. 1, 841-845 (1982).

Olmsted et al., Expression of the F Glycoprotein of Respiratory Syncytial Virus By A Recombinant Vaccinia Virus, Proc. Natl. Acad, Sci, vol. 83, 7462-7466 (1986).

Palese, Pater, Negative Strand RNA Viruses Genetic Engineering and Applications, Proc. Natl. Acad. Sci., vol. 93, 11354-11358 (1996).

Pastey, Manoj K., Nucleotide Sequence Analysis of the Non-Structural NS1 (1C) and NS2 (1B) Proptein Genes of Bovine Respiratory Syncytial Virus, Journal General Virology, vol. 76, 193-197 (1995).

Pastey, Manoj K., Structure and Sequence Comparison of Bovine Respiratory Syncytial Virus Fusion Protein, Virus Research, vol. 29, 195-202 (1993).

Pearson and Lipman, Improved Tools For Biological Sequence Comparison, Proc. Natl. Acad. Sci. USA, vol. 85, 2444-2448 (1988).

Pecters et al., Rescue of Newcastle Disease Virus form Cloned cDNA Evidence that Cleavability of Fusion Protein is A Major Determinant, Journal Virology, vol. 73, No. 6, 5001-5009 (1999).

Perez-Schael, Irene, Efficacy of Rhesus Rotavirus Based Quadrivalent Vaccine In Infants and Young Children In Venezuela, New England J. Med. vol. 337, No. 17, 1181-1187 (1997).

Perrotta et al., A Pseudoknot-Like Structure Required For Efficient Self-Cleavage Of Hepatitis Delta Virus RNA, Nature vol. 350 434-436 (1991).

Piazza et al., Bovine Respiratory Syncytial Virus Protects Cotton Rats Against Human Respiratory Syncytial Virus Infection, J. Virol. vol. 67 1503-1510 (1993).

Prince et al., Immunoprophylaxis and Immunotherapy Of Respiratory Syncytial Virus Infection In The Cotton Rat, Virus Res. vol. 3 193-206 (1985).

Radecke et al., Rescue of Measles Viruses from Cloned DNA, EMBO Journal, vol. 14, No. 23, 5773-5784 (1995).

Radecke, Frank, The Nonstructural C. Protein Is Not Essential for Multiplication of Edmonstron B Strain Measles Virus In Cultured Cells, Virology, vol. 217, 418-421 (1996).

Randhawl, J. S., Nucleotide Sequences of Genes Encoding the Putative Attachment Glycoprotein (G) of Mouse and Tissue Culture Passaged Strains of Pneumonia. Virology, vol. 207 240-245 (1995).

Richardson et al., Evaluation of Five Temperature Sensitive Mutant of Respiratory syncytial Virus In Primates, Journal Mudical Virology, vol. 3, 91-100 (1978).

Roberts et al., Membrane Associated and Secreted Forms of Respiratory Syncytial Virus Attachment Glycoprotein G Are Synthesized, Journal Virology, vol. 68, No. 7, 4538-4546 (1994).

Roberts et al., Recovery of Negative-Strand RNA Viruses from Plasmid DNAs: A Positive Approach Revitalizes A Negative Field, Virology, vol. 247, 1-6 (1998).

Sakai, Yuko, Accommodation of Foreign Genes Into Sendai Virus Genome Sizes of Inserted Genes and Viral Replication, FEBS Letters, vol. 456, 221-226 (1999).

Samal et al., Nucleotide Sequence Analysis of a Matrix and Small Hydrophobic Protein, J. Gen. Virol. vol. 72 1717-1720 (1991).

Samal et al., RNA Replication By A Respiratory Syncytial Virus, J. Virol. vol. 70 5075-5082 (1996).

Samal et al., Molecular Cloning and Sequence Analysis of Bovine Respiratory Syncytial Virus mRNA Encoding the Major Nucleocapsid Protein, Virology vol. 180 453-456 (1991).

Schneider, Henriette, Recombinant Measles Viruses Defective for RNA Editing and V Protein Synthesis Are Viable In Cultured Cells, Virology, vol. 227, 314-322 (1997).

Schnell et al., Infectious Rabies Viruses from cloned cDNA, EMBO J. vol. 13 4195-4203 (1994).

Srikiatkhachorn, Anon, virus Specific CD8 T Lymphocytes Downregulate T Helper Cell Type 2 Cytokine Secretion, Journal Exp. Med., vol. 186, No. 3, 421-432 (1997).

Steinhoff, Mark C., A/Mallard/6750/78 Avian Human But Not A/Ann Arbor/6/60 Cold Adapted Influenza, Journal Infectious Diseases, vol. 163, 1023-1028 (1991).

Sigurs, et al. Asthma and Immunoglobulin E Antibodies After Respiratory Syncytial Virus Bronchiolitis, Pediatrics vol. 95 500-505 (1995).

Smith and Waterman, Comparison of Biosequences, Adv. Appl. Math vol. 2 482 (1981).

Stec et al., Sequence Analysis of Polymerase L Gene of Human Respiratory Syncytial Virus, Virology, vol. 183, 273-287 (1991).

Teng, Michael N., Identification of Respiratory Syncytial virus Proteins Required for Formation and Passage, Journal Virology, vol. 72, No. 7, 5707-5716 (1998).

Teng, Michael N., Altered Growth Characteristic of Recombinant Respiratory Syncytial Viruses, Journal Virology, vol. 73, No. 1, 466-473 (1999).

Van der Poel et al., Respiratory Syncytial Virus Infections In Humans Beings And In Cattle, J. Infect. vol. 29, 215-228 (1994).

Van Wyke Coelingh, Kathleen L., Attenuation of Bovine Parainfluenza Virus Type 3 In Nonhuman Primates-Journal Infectious Diseases, vol. 157, No. 4, 655-662 (1988).

Walravens et al., Sequence Comparison Between The Fusion Protein Of Human And Bovine Respiratory Syncytial Viruses, J. Gen. Virol. vol. 71 3009-3014 (1990).

Walsh et al., Immunization with Glycoprotein Subunits of Respiratory Syncytial Virus To Protect Cotton Rats Against Viral Infection, J. Infect. Dis. vol. 155 1198-1204 (1987).

Wathen, M. W., Characterization of A Novel Human Respiratory syncytial virus Chimeric FG Glycoprotein Expressed Using a Baculovirus Vector, Journal General Virology, vol. 70, 2625-2635 (1989).

Whelan, Sean P. J., Efficient Recovery of Infectious Vesicular Stomatitis Virus Entirely from cDNA Clones, Proc. Natl. Acad. Sci., vol. 92, 8388-8392 (1995).

Whitehead, Stephen S., A Single Nucleotide Substitution In Trascription Start Signal of M2 Gene, Virology, vol. 247, 232-239 (1998).

Whitehead, Stephen S., Recombinant Respiratory Syncytial Virus (RSV) Bearing A Set of Mutations, Journal Virology, vol. 72, No. 5, 4467-4471 (1998).

Wright et al., Administration of A Highly Attenuated Live Respiratory Syncytial Virus Vaccine to Adults and Children, Infection and Immunity, vol. 37, No, 1, 397-400 (1982).

Whitehead et al., Recombinant Respiratory Syncytial Virus Bearing A Deletion of Either the NS2 or SH Gene, Journal Virology, vol. 73, No. 4, 3438-3442 (1999).

Whitehead et al, Addition of A Missense Mutation Present In The L Gene of Respiratory Syncytial Virus (RSV) cpts530 1030 to RSV Vacine Candidate cpts 248 404, J. Virol. vol. 73 871-877 (1999).

Whitehead et al., Replacement of The F and G Proteins of Respiratory Syncytial Virus (RSV) Subgroup A, J. Virol. vol. 73 9773-9780 (1999).

Wigler et al., Biochemical Transfer Of Single Copy Encaryotic Genes Using Total Cellular DNA As Donor, Cell vol. 14 725-731 (1978).

Wright et al., Evaluation of a Live Attenuated Respiratory Syncytial Virus Vaccine In Infants, Journal Pediatrics, vol. 88, No. 6, 931-936 (1976).

Wright et al., Genetic Studies Of Respiratory Syncytial Virus Temperature Sensitive Mutants, Archiv Fur Die Gesamte Virusforschung vol. 41, 238-247 (1973).

Wyatt et al., Replication Deficient Vaccinia Virus Encoding Bacteriophage T7 RNA Polymerase For Transient Gene Expression In Mammalian Cells, Virology vol. 210 202-205 (1995).

Yunus et al, Sequence Analysis Of A Functional Polymerase (L) Gene Of Bovine Respiratory Syncytial Virus: Determination Of Minimal Trans-Acting Requirements For RNA Replication, J. Gen. Virol. vol. 79 2231-2238 (1998).

Zamora, Miguel, Gene Junction Sequences of Bovine Respiratory Syncytial Virus, Virus Research, vol. 24, 115-151 (1992).

Zamora et al., Sequence Analysis of M2 mRNA of Bovine Respiratory Syncytial Virus, Journal General Virology, vol. 73, 737-741 (1992).

Zimmermann et al., The Poly(C) Region Affects Progression Of Encephalomyocarditis Virus Infection in Langerhans' Islets But Not In The Myocardium, J. Virol. vol. 71 4145-4149 (1997).

Karron et al., A Live Attenuated Bovine Parainfluenza Virus Type 3 Vaccines is Safe, Infectious, Immunogenic, and Phenotypically Stable in Infants and Children, J. Inf. Dis. 171:1107-1114, 1995a.

Lamb et al., Paramyxoviridae The Viruses and Their Replication, Fields Virology vol. 1 1177-1204 (1996).

Wagner et al., Rhabdoviridae: The Viruses and Their Replication, Fields Virology 1121-1135 (1996).

Young et al., Paramyxoviridae Use Distinct Virus Specific mechanisms to Circumvent the Interferon Response, Virology vol. 269 383-390 (2000).

Meignier et al., eds., Animal Models of Respiratory Syncytial Virus Infection, *Merieux Foundation Publication*, 1991.

Ausubel et al., (ed.) Current Protocols in Molecular Biology, *John Wiley and Sons, Inc.*, NY, 1987.

Buchholz, "Generation of Bovine Respiratory Syncytial Virus (BRSV) from cDNA: BRSV NS2 is not Essential for Virus Replication in Tissue Culture, and the Human RSV Leader Region Acts as a Functional BRSV Genome Promoter," Journal of Virology, Jan. 1999, p. 251-259.

* cited by examiner

I. SH/G intergenic region

```
                      5'                                                                                    3'
ATue51908    4640  AGTTATTTAAAATTAAACTTAAAAATGGTTTATGGTTACATACAGATGTTGGGGCAAATACAAGTATGTCCAACCATACC  4719
                  ||||||||||||||||||||||||||||||||||||||||||||||||||||||||||||||||||||||||||||||
rBRSV        4640  AGTTATTTAAAATTAAACTTAAAAATGGTTTATGTTACATACAGATGTTGGGGCAAATACAAGTATGTCCAACCATACC  4719
                  ||||||||||||||||||||||||||||||||||||||||||||||||||||||||||||||||||||||||||||||
rBRSV/LongF  4640  AGTTATTTAAAATTAAACTTAAAAATGGTTTATGTCGACATACAGATGTTGGGGCAAATACAAGTATGTCCAACCATACC  4719
                                                      SalI                G gene start        ↳ G orf
                   SH gene end                                             signal
                   signal
```

II. G/F intergenic region

```
                      5'                                                                               3'
ATue51908    5517  AGTTATTTAAAAGATATGTATAATTCACTAATTAAAACTAAGGATGGCGACA                              5578
                  |||||||||||||||||||||||||||||||||||||||||||||||||||
rBRSV        5517  AGTTATTTAAAAGATATGCATGCTTCACTAATTAAAACTAAGGATGGCGACA                              5578
                                     SphI
rBRSV/LongF  5517  AGTTATTTAAAAGATATGCATGC..........GGGGCAAATAACAATGGAGTTG                           5562
                                     SphI              F gene start    ↳ F orf
                   G gene end                           signal
                   signal
```

III. F/M2 intergenic region

```
                      5'                                                                                                3'
ATue51908    7436  CCATGTTGATAGTTATATAAAATATTATATTAGTTCTCAAAGAATAAATTATTAACAACCAATCATTCAAAAGATGGGGCAAAT  7522
                  ||||||||||||||||||||||||||||||||||||||||||||||||||||||||||||||||||||||||||||||||||||
rBRSV        7436  CCATGTTGATAGTTATATAAAATATTATATTAGTTCTCGAGAATAAATCGATTAACAACCAATCATTCAAAAGATGGGGCAAAT  7522
                                                        XhoI           ClaI
rBRSV/LongF  7422  CCTAGTTTATAGTTATATAAAA..........AATAAATCGATTAACAACCAATCATTCAAAAGATGGGGCAAAT          7496
                                                                ClaI                    M2 gene start
                   F noncod. F gene end                                                  signal
                   signal
```

Figure 10

A. rBRSV

B. Modifications to rBRSV to create rBRSV/A2-G1F2 leader—GCGGCCGCTAAATTTAACTCCCTTGCTTAGCGATG
        NotI                          BlpI
(SEQ ID NO. 15)

leader—GGGGCAAATA|CAAGTTAATTCGCGGCCGCCCCTCTCTTCTACAGAAATG
        Gene-start                NotI
(SEQ ID NO. 14)

GE|CACAAT|GGGGCAAATA|AGCTTAGCGGCCGC
          Gene-start    BlpI    NotI
(SEQ ID NO. 16)

C. rBRSV/A2-G1F2

Figure 13

A. Insert MluI site into rBRSV/A2

```
         taaaa
    TAAAGACGCGTT   MluI
         3204
         P-M IG
```

B. Replace BRSV M and SH genes with HRSV M gene to create rBRSV/A2-MGF

```
AGTTAGTAAAAATAAAGACGCGTT    TTATGTCGACTGGGGCAAATGCAAACATG...
                   MluI       SalI
BRSV P                      M-G IG    HRSV G
gene-end                              gene-start
     3203   3252                4210
            P-M IG
            HRSV M gene
```

C. Structure of rBRSV/A2-MGF

PRODUCTION OF ATTENUATED, HUMAN-BOVINE CHIMERIC RESPIRATORY SYNCYTIAL VIRUS VACCINES

CROSS-REFERENCES TO RELATED APPLICATIONS

This application is a continuation of U.S. patent application Ser. No. 09/602,212, filed on Jun. 23, 2000, now abandoned, which claims the benefit of U.S. Provisional Patent Application No. 60/143,132, filed by Buchholz et al. on Jul. 9, 1999.

BACKGROUND OF THE INVENTION

Human respiratory syncytial virus (HRSV) is the leading viral agent of serious pediatric respiratory tract disease worldwide (Collins, et al., *Fields Virology* 2:1313-1352, 1996). RSV outranks all other microbial pathogens as a cause of pneumonia and bronchiolitis in infants under one year of age. Virtually all children are infected by two years of age, and reinfection occurs with appreciable frequency in older children and young adults (Chanock et al., in *Viral Infections of Humans*, 3rd ed., A. S. Evans, ed., Plenum Press, N.Y., 1989). RSV is responsible for more than one in five pediatric hospital admissions due to respiratory tract disease, and in the United States alone causes nearly 100,000 hospitalizations and 4,500 deaths yearly. (Heilman, *J Infect Dis* 161:402-6, 1990). In addition, there is evidence that serious respiratory tract infection early in life can initiate or exacerbate asthma (Sigurs, et al., *Pediatrics* 95:500-5, 1995).

While human RSV usually is thought of in the context of the pediatric population, it also is recognized as an important agent of serious disease in the elderly (Falsey, et al., *J. Infect. Dis.* 172:389-394, 1995). Human RSV also causes life-threatening disease in certain immunocompromised individuals, such as bone marrow transplant recipients (Fouillard, et al., *Bone Marrow Transplant* 9:97-100, 1992).

For treatment of human RSV, one chemotherapeutic agent, ribavirin, is available. However, its efficacy and use is controversial. There are also licensed products for RSV intervention which are composed of pooled donor IgG (Groothuis, et al. *N Engl J Med* 329:1524-30, 1993) or a humanized RSV-specific monoclonal antibody. These are administered as passive immunoprophylaxis agents to high risk individuals. While these products are useful, their high cost and other factors, such as lack of long term effectiveness, make them inappropriate for widespread use. Other disadvantages include the possibility of transmitting blood-borne viruses and the difficulty and expense in preparation and storage. Moreover, the history of the control of infectious diseases, and especially diseases of viral origin, indicates the primary importance of vaccines.

Despite decades of investigation to develop effective vaccine agents against RSV, no safe and effective vaccine has yet been achieved to prevent the severe morbidity and significant mortality associated with RSV infection. Failure to develop successful vaccines relates in part to the fact that small infants have diminished serum and secretory antibody responses to RSV antigens. Thus, these individuals suffer more severe infections from RSV, whereas cumulative immunity appears to protect older children and adults against more serious impacts of the virus.

The mechanisms of immunity in RSV infection have recently come into focus. Secretory antibodies appear to be most important in protecting the upper respiratory tract, whereas high levels of serum antibodies are thought to have a major role in resistance to RSV infection in the lower respiratory tract. RSV-specific cytotoxic T cells, another effector arm of induced immunity, are also important in resolving an RSV infection. However, while this latter effector can be augmented by prior immunization to yield increased resistance to virus challenge, the effect is short-lived. The F and G surface glycoproteins are the two major protective antigens of RSV, and are the only two RSV proteins which have been shown to induce RSV neutralizing antibodies and long term resistance to challenge (Collins et al., *Fields Virology*, Fields et al. eds., 2:1313-1352, Lippincott-Raven, Philadelphia, 1996; Connors et al., *J. Virol.* 65(3):1634-7, 1991). The third RSV surface protein, SH, did not induce RSV-neutralizing antibodies or significant resistance to RSV challenge.

An obstacle to developing live RSV vaccines is the difficulty in achieving an appropriate balance between attenuation and immunogenicity, partly due to the genetic instability of some attenuated viruses, the relatively poor growth of RSV in cell culture, and the instability of the virus particle. In addition the immunity which is induced by natural infection is not fully protective against subsequent infection. A number of factors probably contribute to this, including the relative inefficiency of the immune system in restricting virus infection on the luminal surface of the respiratory tract, the short-lived nature of local mucosal immunity, rapid and extensive virus replication, reduced immune responses in the young due to immunological immaturity, immunosuppression by transplacentally derived maternal serum antibodies, and certain features of the virus such as a high degree of glycosylation of the G protein. Also, as will be described below, human RSV exists as two antigenic subgroups A and B, and immunity against one subgroup is of reduced effectiveness against the other.

Although RSV can reinfect multiple times during life, reinfections usually are reduced in severity due to protective immunity induced by prior infection, and thus immunoprophylaxis is feasible. A live-attenuated RSV vaccine would be administered intranasally to initiate a mild immunizing infection. This has the advantage of simplicity and safety compared to a parenteral route. It also provides direct stimulation of local respiratory tract immunity, which plays a major role in resistance to RSV. It also abrogates the immunosuppressive effects of RSV-specific maternally-derived serum antibodies, which typically are found in the very young. Also, while the parenteral administration of RSV antigens can sometimes be associated with immunopathologic complications (Murphy et al., *Vaccine* 8(5):497-502, 1990), this has never been observed with a live virus.

A formalin-inactivated virus vaccine was tested against RSV in the mid-1960s, but failed to protect against RSV infection or disease, and in fact exacerbated symptoms during subsequent infection by the virus. (Kim et al., *Am. J. Epidemiol.*, 89:422-434, 1969; Chin et al., *Am J. Epidemiol.*, 89:449-463, 1969; Kapikian et al., *Am. J. Epidemiol.*, 89:405-421, 1969).

More recently, vaccine development for RSV has focused on attenuated RSV mutants. Friedewald et al., (*J. Amer. Med. Assoc.* 204:690-694, 1968) reported a cold passaged mutant of RSV (cpRSV) which appeared to be sufficiently attenuated to be a candidate vaccine. This mutant exhibited a slight increased efficiency of growth at 26° C. compared to its wild-type (wt) parental virus, but its replication was neither temperature sensitive nor significantly cold-adapted. The cold-passaged mutant, however, was attenuated for adults. Although satisfactorily attenuated and immunogenic for infants and children who had been previously infected with RSV (i.e., seropositive individuals), the cpRSV mutant retained a low level virulence for the upper respiratory tract of seronegative infants.

Similarly, Gharpure et al., (*J. Virol.* 3:414-421, 1969) reported the isolation of temperature sensitive RSV (tsRSV) mutants which also were promising vaccine candidates. One mutant, ts-1, was evaluated extensively in the laboratory and in volunteers. The mutant produced asymptomatic infection in adult volunteers and conferred resistance to challenge with wild-type virus 45 days after immunization. Again, while seropositive infants and children underwent asymptomatic infection, seronegative infants developed signs of rhinitis and other mild symptoms. Furthermore, instability of the ts phenotype was detected. Although virus exhibiting a partial or complete loss of temperature sensitivity represented a small proportion of virus recoverable from vaccinees, it was not associated with signs of disease other than mild rhinitis.

These and other studies revealed that certain cold-passaged and temperature sensitive RSV strains were underattenuated and caused mild symptoms of disease in some vaccinees, particularly seronegative infants, while others were overattenuated and failed to replicate sufficiently to elicit a protective immune response, (Wright et al., *Infect. Immun.*, 37:397-400, 1982). Moreover, genetic instability of candidate vaccine mutants has resulted in loss of their temperature sensitive phenotype, further hindering development of effective RSV vaccines. See generally, (Hodes et al., *Proc. Soc. Exp. Biol. Med.* 145:1158-1164, 1974; McIntosh et al., *Pediatr. Res.* 8:689-696, 1974; and Belshe et al., *J. Med. Virol.*, 3:101-110, 1978).

As an alternative to live-attenuated RSV vaccines, investigators have also tested subunit vaccine candidates using purified RSV envelope glycoproteins. The glycoproteins induced resistance to RS virus infection in the lungs of cotton rats, (Walsh et al., *J. Infect. Dis.* 155:1198-1204, 1987), but the antibodies had very weak neutralizing activity and immunization of rodents with purified subunit vaccine led to disease potentiation (Murphy et al., *Vaccine* 8:497-502, 1990).

Recombinant vaccinia virus vaccines which express the F or G envelope glycoprotein have also been explored. These recombinants express RSV glycoproteins which are indistinguishable from the authentic viral counterpart, and rodents infected intradermally with vaccinia-RSV F and G recombinants developed high levels of specific antibodies that neutralized viral infectivity. Indeed, infection of cotton rats with vaccinia-F recombinants stimulated almost complete resistance to replication of RSV in the lower respiratory tract and significant resistance in the upper tract. (Olmsted et al., *Proc. Natl. Acad. Sci. USA* 83:7462-7466, 1986). However, immunization of chimpanzees with vaccinia-F and -G recombinant provided almost no protection against RSV challenge in the upper respiratory tract (Collins et al., *Vaccine* 8:164-168, 1990) and inconsistent protection in the lower respiratory tract (Crowe et al., *Vaccine* 11:1395-1404, 1993).

Despite these various efforts to develop an effective RSV vaccine, no licensed vaccine has yet been approved for RSV. The unfulfilled promises of prior approaches underscores a need for new strategies to develop RSV vaccines, and in particular methods for manipulating recombinant RSV to incorporate genetic changes that yield new phenotypic properties in viable, attenuated RSV recombinants. However, manipulation of the genomic RNA of RSV and other non-segmented negative-sense RNA viruses has heretofore proven difficult. Major obstacles in this regard include non-infectivity of naked genomic RNA of these viruses, poor viral growth in tissue culture, lengthy replication cycles, virion instability, a complex genome, and a refractory organization of gene products.

Recombinant DNA technology has made it possible to recover infectious non-segmented negative-stranded RNA viruses from cDNA, to genetically manipulate viral clones to construct novel vaccine candidates, and to rapidly evaluate their level of attenuation and phenotypic stability (for reviews, see Conzelmann, *J. Gen. Virol.* 77:381-89, 1996; Palese et al., *Proc. Natl. Acad. Sci. U.S.A.* 93:11354-58, 1996). In this context, recombinant rescue has been reported for infectious respiratory syncytial virus (RSV), parainfluenza virus (PIV), rabies virus (RaV), vesicular stomatitis virus (VSV), measles virus (MeV), rinderpest virus and Sendai virus (SeV) from cDNA-encoded antigenomic RNA in the presence of essential viral proteins (see, e.g., Garcin et al., *EMBO J.* 14:6087-6094, 1995; Lawson et al., *Proc. Natl. Acad. Sci. U.S.A.* 92:4477-81, 1995; Radecke et al., *EMBO J.* 14:5773-5784, 1995; Schnell et al., *EMBO J.* 13:4195-203, 1994; Whelan et al., *Proc. Natl. Acad. Sci. U.S.A.* 92:8388-92, 1995; Hoffman et al., *J Virol.* 71:4272-4277, 1997; Pecters et al., *J. Virol.* 73:5001-5009, 1999; Kato et al., *Genes to Cells* 1:569-579, 1996; Roberts et al., *Virology* 247(1), 1-6, 1998; Baron et al., *J Virol.* 71:1265-1271, 1997; International Publication No. WO 97/06270; U.S. Provisional Patent Application No. 60/007,083, filed Sep. 27, 1995; U.S. patent application Ser. No. 08/720,132, filed Sep. 27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. Pat. No. 5,993,824, issued Nov. 30, 1999 (corresponding to International Publication No. WO 98/02530); U.S. patent application Ser. No. 09/291,894, filed by Collins et al. on Apr. 13, 1999; U.S. Provisional Patent Application No. 60/129,006, filed by Murphy et al. on Apr. 13, 1999; Collins, et al., *Proc Nat. Acad. Sci. USA* 92:11563-11567, 1995; Bukreyev, et al., *J Virol* 70:6634-41, 1996, Juhasz et al., *J. Virol.* 71(8):5814-5819, 1997; Durbin et al., *Virology* 235:323-332, 1997; He et al. *Virology* 237:249-260, 1997; Baron et al. *J. Virol.* 71:1265-1271, 1997; Whitehead et al., *Virology* 247(2):232-9, 1998a; Buchholz et al. *J. Virol.* 73:251-9, 1999; Whitehead et al., *J. Virol.* 72(5):4467-4471, 1998b; Jin et al. *Virology* 251:206-214, 1998; and Whitehead et al., *J. Virol.* 73:(4)3438-3442, 1999, and Bukreyev, et al., *Proc Nat Acad Sci USA* 96:2367-72, 1999, each incorporated herein by reference in its entirety for all purposes).

Bovine RSV (BRSV), which is antigenically-related to human RSV (HRSV), offers an alternative approach to the development of a live attenuated virus vaccine for HRSV. The first vaccine used in humans, live vaccinia virus believed to be of bovine origin, was developed by Jenner almost 200 years ago for the control of smallpox. During the ensuing two centuries, vaccinia virus was successful in controlling this disease and played an essential role in the final eradication of smallpox. In this "Jennerian" approach to vaccine development, an antigenically-related animal virus is used as a vaccine for humans. Animal viruses that are well adapted to their natural host often do not replicate efficiently in humans and hence are attenuated. At present, there is a lack of a thorough understanding regarding the genetic basis for this form of host range restriction. Evolution of a virus in its animal or avian host results in significant divergence of nucleotide (nt) and amino acid sequences from that of the corresponding sequences in the related human virus. This divergent sequence, consisting of a large number of sequence differences, specifies the host range attenuation phenotype. Having an attenuation phenotype which is based on numerous sequence differences is a desirable property in a vaccine virus since it should contribute to the stability of the attenuation phenotype of the animal virus following its replication in humans.

The recently licensed quadrivalent rotavirus is an example of the Jennerian approach to vaccine development in which a nonhuman rotavirus strain, the rhesus rotavirus (RRV), was found to be attenuated in humans and protective against human serotype 3 to which it is antigenically highly related (Kapikian et al., *Adv. Exp. Med. Biol.* 327:59-69, 1992, incorporated herein by reference). Since there was a need for a multivalent vaccine that would induce resistance to each of the four major human rotavirus serotypes, the Jennerian approach was modified by constructing three reassortant viruses using conventional genetic techniques of gene reassortment in tissue culture. Each single gene reassortant virus contained 10 RRV genes plus a single human rotavirus gene that coded for the major neutralization antigen (VP7) of serotype 1, 2, or 4. The intent was to prepare single gene substitution RRV reassortants with the attenuation characteristics of this simian virus and the neutralization specificity of human rotavirus serotype 1, 2, or 4. The quadrivalent vaccine based on the host range restriction of the simian RRV in humans provided a high level of efficacy against human rotavirus infection in infants and young children (Perez-Schael et al., *N. Engl. J. Med.* 337:1181-7, 1997, incorporated herein by reference).

However, the licensed vaccine retains mild reactogenicity in older seronegative infants lacking maternal antibody, therefore a second generation Jennerian vaccine, based on the UK strain of bovine rotavirus, is being developed to replace the RRV vaccine. The Jennerian approach also is being explored to develop vaccines for parainfluenza type 1 virus and for hepatitis A virus (Emerson et al., *J. Infect. Dis.* 173: 592-7, 1996; Hurwitz et al., *Vaccine* 15, 533-40, 1997, each incorporated herein by reference). The Jennerian approach was used for the development of a live attenuated vaccine for influenza A virus but it failed to produce a consistently attenuated vaccine for use in humans (Steinhoff et al., *Journal of Infectious Diseases* 163:1023-1028, 1991, incorporated herein by reference).

Based on the foregoing developments, it is now possible to recover infectious RSV from cDNA and to design and implement various genetic manipulations to RSV clones to construct novel vaccine candidates. Thereafter, the level of attenuation and phenotypic stability, among other desired phenotypic characteristics, can be evaluated and adjusted. The challenge which thus remains is to develop a broad and diverse menu of genetic manipulations that can be employed, alone or in combination with other types of genetic manipulations, to construct infectious, attenuated RSV clones that are useful for broad vaccine use. In this context, an urgent need remains in the art for additional tools and methods that will allow engineering of safe and effective vaccines to alleviate the serious health problems attributable to RSV. Surprisingly, the present invention fulfills this need by providing additional tools for constructing infectious, attenuated RSV vaccine candidates.

SUMMARY OF THE INVENTION

The present invention provides a human-bovine chimeric respiratory syncytial virus (RSV) that is infectious and attenuated in humans and other mammals. In related aspects, the invention provides novel methods for designing and producing attenuated, human-bovine chimeric RSV that are useful in various compositions to generate a desired immune response against RSV in a host susceptible to RSV infection. Included within these aspects of the invention are novel, isolated polynucleotide molecules and vectors incorporating such molecules that comprise a chimeric RSV genome or antigenome including a partial or complete human or bovine RSV "background" genome or antigenome combined or integrated with one or more heterologous gene(s) or genome segment(s) of a different RSV strain or subgroup virus. Human-bovine chimeric RSV according to the invention may elicit an immune response to a specific RSV subgroup or strain, or a polyspecific response against multiple RSV subgroups or strains. Yet additional compositions and methods are provided for designing and producing attenuated, human-bovine chimeric RSV as vectors for incorporating antigenic determinants of other pathogens to generate a desired immune response against different pathogens of interest. Also provided within the invention are methods and compositions incorporating human-bovine chimeric RSV for prophylaxis and treatment of infection and disease caused by RSV and other pathogens.

Chimeric human-bovine RSV of the invention are recombinantly engineered to incorporate nucleotide sequences from both human and bovine RSV strains and produce an infectious, chimeric virus or subviral particle therefrom. In this manner, candidate vaccine viruses are recombinantly engineered to elicit an immune response against RSV or another pathogen in a mammalian host susceptible to infection from the pathogen of interest, including humans and non-human primates.

Exemplary human-bovine chimeric RSV of the invention incorporate a chimeric RSV genome or antigenome comprising both human and bovine polynucleotide sequences, as well as a major nucleocapsid (N) protein, a nucleocapsid phosphoprotein (P), a large polymerase protein (L), and a RNA polymerase elongation factor. Additional RSV proteins may be included in various combinations to provide a range of infectious subviral particles, up to a complete viral particle or a viral particle containing supernumerary proteins, antigenic determinants or other additional components.

Chimeric human-bovine RSV of the invention include a partial or complete "background" RSV genome or antigenome derived from or patterned after a human or bovine RSV strain or subgroup virus combined with one or more heterologous gene(s) or genome segment(s) of a different RSV strain or subgroup virus to form the human-bovine chimeric RSV genome or antigenome. In certain aspects of the invention, chimeric RSV incorporate a partial or complete bovine RSV background genome or antigenome combined with one or more heterologous gene(s) or genome segment(s) from a human RSV. In alternate aspects of the invention chimeric RSV incorporate a partial or complete human RSV background genome or antigenome combined with one or more heterologous gene(s) or genome segment(s) from a bovine RSV.

In exemplary embodiments, the invention is directed to infectious chimeric respiratory syncytial viruses (RSVs) that comprise a major nucleocapsid (N) protein, a nucleocapsid phosphoprotein (P), a large polymerase protein (L), a RNA polymerase elongation factor, and a partial or complete RSV background genome or antigenome of a human or bovine RSV combined with one or more heterologous gene(s) and/or genome segment(s) of a different RSV to form a human-bovine chimeric RSV genome or antigenome. The heterologous gene(s) and/or genome segment(s) that are useful within the invention include one or more RSV NS1, NS2, N, P, M, SH, M2(ORF1), M2(ORF2), L, F or G gene(s) or genome segment(s). Alternatively, heterologous genes and genome segments for incorporation within human-bovine chimeric RSV may include a leader, trailer or intergenic region of the RSV genome, or a segment thereof.

Within more detailed embodiments, human-bovine chimeric RSV of the invention incorporate one or more heterologous genes and/or genome segments that encode a RSV F, G and/or SH glycoprotein or an immunogenic domain or epitope thereof. Alternatively, the human-bovine chimeric RSV may incorporate a chimeric glycoprotein having both human and bovine glycoprotein domains or immunogenic epitopes. For example, the latter type of chimera may be constructed by incorporation into a bovine background genome or antigenome a heterologous genome segment encoding a glycoprotein ectodomain in proper reading frame with a genome segment encoding a functional remaining portion of the corresponding glycoprotein in the bovine genome or antigenome, whereby the resultant chimeric virus expresses a functional chimeric glycoprotein.

In other alternative embodiments of the invention, human-bovine chimeric RSV are provided wherein a human RSV is attenuated by incorporation of a selected bovine gene, genome segment, or plurality of genes or genome segments. In certain embodiments selected heterologous gene sets from BRSV are coordinately transferred into a HRSV background genome or antigenome. Exemplary bovine RSV genes from which individual or coordinately transferred groups of genes may be selected include the RSV N, P, NS1, NS2, M2-1 and M genes, which may be replaced singly or in any combination in a human RSV background genome or antigenome by one or more heterologous gene(s) from a bovine RSV to yield an attenuated chimeric derivative. In more detailed aspects, both N and P genes of a human RSV are replaced coordinately by counterpart N and P genes from a bovine RSV. This coordinate gene replacement is facilitated by functional cooperativity between certain genes in the RSV genome, which often arises in the case of neighboring gene pairs in the genome. Thus, in other alternative embodiments, both NS1 and NS2 genes of a human RSV are replaced by counterpart NS1 and NS2 genes from a bovine RSV. In yet additional embodiments, two or more of the M2-1, M2-2 and L genes of a HRSV are replaced by counterpart genes from a bovine RSV. For certain vaccine candidates within the invention for which a high level of host-range restriction is desired, each of the N, P, NS1, NS2, M2-1 and M genes of a human RSV are replaced by counterpart N, P, NS1, NS2, M2-1 and M genes from a bovine RSV.

Within a different aspect of the invention, human-bovine chimeric RSV are constructed wherein the chimeric genome or antigenome comprises a partial or complete bovine RSV background genome or antigenome combined with one or more heterologous gene(s) and/or genome segment(s) from a human RSV. In certain embodiments, one or more human RSV glycoprotein genes selected from F, G and SH, or one or more genome segment(s) encoding cytoplasmic domain, transmembrane domain, ectodomain or immunogenic epitope portion(s) of F, G, and/or SH is/are added or substituted within a partial or complete bovine RSV background genome or antigenome. For example, one or both human RSV glycoprotein genes F and G may be substituted to replace one or both counterpart F and G glycoprotein genes in a partial bovine RSV background genome or antigenome. Within these and related embodiments, the human-bovine chimeric genome or antigenome can incorporate antigenic determinants from one or both subgroup A and subgroup B human RSV. In more detailed aspects, both human RSV glycoprotein genes F and G are substituted to replace counterpart F and G glycoprotein genes in the bovine RSV background genome or antigenome. An exemplary human-bovine chimeric RSV bearing these features describe in the examples below is rBRSV/A2.

Yet additional human-bovine chimeric RSV of the invention incorporate one or more human RSV glycoprotein genes selected from F, G and SH which are added or substituted at a position that is more promoter-proximal compared to a wild-type gene order position of a counterpart gene or genome segment within a partial or complete bovine RSV background genome or antigenome. In one such embodiment, both human RSV glycoprotein genes G and F are substituted at gene order positions 1 and 2, respectively, to replace counterpart G and F glycoprotein genes deleted at wild type positions 7 and 8, respectively in a partial bovine RSV background genome or antigenome. An exemplary human-bovine chimeric RSV bearing these features describe in the examples is rBRSV/A2-G1F2.

Coordinate gene transfers within human-bovine chimeric RSV are also directed to introduction of human antigenic genes within a bovine background genome or antigenome. In certain embodiments, one or more human RSV envelope-associated genes selected from F, G, SH, and M is/are added or substituted within a partial or complete bovine RSV background genome or antigenome. For example, one or more human RSV envelope-associated genes selected from F, G, SH, and M may be added or substituted within a partial bovine RSV background genome or antigenome in which one or more envelope-associated genes selected from F, G, SH, and M is/are deleted. In more detailed aspects, one or more genes from a gene set defined as human RSV envelope-associated genes F, G, and M are added within a partial bovine RSV background genome or antigenome in which envelope-associated genes F, G, SH, and M are deleted. An exemplary human-bovine chimeric RSV bearing these features describe in the examples below is rBRSV/A2-MGF.

As used herein, "RSV gene" generally refers to a portion of the RSV genome encoding an mRNA and typically begins at the upstream end with the 10-nucleotide gene-start (GS) signal and ends at the downstream end with the 12 to 13-nucleotide gene-end (GE) signal. Ten such genes for use within the invention are known for RSV, namely NS1, NS2, N, P, M, SH, G, F, M2 and L. The term "gene" is also used herein to refer to a "translational open reading frame" (ORF). ORF is more specifically defined as a translational open reading frame encoding a significant RSV protein, of which 11 are currently recognized: NS1, NS2, N, P, M, SH, G, F, M2-1 (alternatively, M2(ORF1)), M2-2 (alternatively, M2(ORF2)), and L. Thus, the term "gene" interchangeably refers to a genomic RNA sequence that encodes a subgenomic RNA, and to a ORF (the latter term applies particularly in a situation such as in the case of the RSV M2 gene, where a single mRNA contains two overlapping ORFs that encode distinct proteins). Collins et al., *J. Gen. Virol.* 71:3015-3020, 1990; Bermingham and Collins, *Proc. Natl. Acad. Sci. USA* 96:11259-11264, 1999; Ahmadian et al., *EMBO J.* 19:2681-2689, 2000; Jin et al., *J. Virol.* 74:74-82, 2000 (each incorporated herein by reference). When the term "gene" is used in the context of determining gene position relative to a promoter position, the term ordinarily refers strictly to an mRNA-encoding sequence bordered by transcription gene-start and gene-end signal motifs (Collins et al., *Proc. Natl. Acad. Sci. USA* 83:4594-4598, 1986; Kuo et al., *J. Virol.* 70:6892-6901, 1996; each incorporated herein by reference).

By "genome segment" is meant any length of continuous nucleotides from the RSV genome, which may be part of an ORF, a gene, or an extragenic region, or a combination thereof.

The partial or complete background genome or antigenome typically acts as a recipient backbone or vector into which are imported heterologous genes or genome segments of the counterpart, human or bovine RSV. Heterologous genes or genome segments from the counterpart, human or bovine RSV represent "donor" genes or polynucleotides that are combined with, added to, or substituted within, the background genome or antigenome to yield a chimeric RSV that exhibits novel phenotypic characteristics compared to one or both of the contributing RSVs. For example, addition or substitution of heterologous genes or genome segments within a selected recipient RSV strain may result in an increase or decrease in attenuation, growth changes, altered immunogenicity, or another desired phenotypic changes as compared with a corresponding phenotype(s) of the unmodified recipient and/or donor.

Genes and genome segments that may be selected for use as heterologous inserts or additions within the invention include genes or genome segments encoding a NS1, NS2, N, P, M, SH, M2(ORF1), M2(ORF2), L, F or G protein or portion thereof. Regulatory regions, such as the extragenic leader or trailer regions, can also be considered. In preferred embodiments of the invention, chimeric RSV incorporates one or more heterologous gene(s) that encode an RSV F, G or SH glycoprotein. Alternatively, the chimeric RSV may incorporate a genome segment encoding a cytoplasmic domain, transmembrane domain, ectodomain or immunogenic epitope of a RSV F, G or SH glycoprotein. These immunogenic proteins, domains and epitopes are particularly useful within human-bovine chimeric RSV because they generate novel immune responses in an immunized host. In particular, the G and F proteins, and immunogenic domains and epitopes therein, provide major neutralization and protective antigens. In addition, genes and genome segments encoding non-RSV proteins, for example, an SH protein as found in mumps and SV5 viruses, may be incorporated within human-bovine PIV of the invention. Regulatory regions, such as the extragenic 3' leader or 5' trailer regions, and gene-start, gene-end, intergenic regions, or 3' or 5' non-coding regions, are also useful as heterologous substitutions or additions.

For example, addition or substitution of one or more immunogenic gene(s) or genome segment(s) from a human RSV subgroup or strain to or within a bovine recipient genome or antigenome yields a recombinant, chimeric virus or subviral particle capable of generating an immune response directed against the human donor virus, including one or more specific human RSV subgroups or strains, while the bovine backbone confers an attenuated phenotype making the chimera a useful candidate for vaccine development. In one such exemplary embodiment, one or more human RSV glycoprotein genes F, SH, and/or G are added to or substituted within a partial or complete bovine genome or antigenome to yield an attenuated, infectious human-bovine chimera that elicits an antihuman RSV immune response in a susceptible host. In alternate embodiments human-bovine chimeric RSV additionally incorporates a gene or genome segment encoding an immunogenic protein, protein domain or epitope from multiple human RSV strains, for example two F or G proteins or immunogenic portions thereof from both RSV subgroups A and B. In yet additional alternate embodiments a human-bovine chimeric RSV genome or antigenome encodes a chimeric glycoprotein in the recombinant virus or subviral particle having both human and bovine glycoprotein domains or immunogenic epitopes. For example, a heterologous genome segment encoding a glycoprotein ectodomain from a human RSV F, SH or G glycoprotein may be joined with a genome segment encoding corresponding bovine F, SH or G glycoprotein cytoplasmic and endodomains in the background bovine genome or antigenome.

According to the methods of the invention, human-bovine chimeric RSV may be constructed by substituting the heterologous gene or genome segment for a counterpart gene or genome segment in a partial RSV background genome or antigenome. Alternatively, the heterologous gene or genome segment may be added as a supernumerary gene or genome segment in combination with a complete (or partial if another gene or genome segment is deleted) RSV background genome or antigenome. For example, two human RSV G or F genes or genome segments can be included, one each from RSV subgroups A and B.

Often, a heterologous gene or genome segment is added at an intergenic position within a partial or complete RSV background genome or antigenome. Alternatively, the gene or genome segment can be placed in other noncoding regions of the genome, for example, within the 5' or 3' noncoding regions or in other positions where noncoding nucleotides occur within the partial or complete genome or antigenome. In one aspect, noncoding regulatory regions contain cis-acting signals required for efficient replication, transcription, and translation, and therefore represent target sites for modification of these functions by introducing a heterologous gene or genome segment or other mutation as disclosed herein. In more detailed aspects of the invention, attenuating mutations are introduced into cis-acting regulatory regions to yield, e.g., (1) a tissue specific attenuation (Gromeier et al., *J. Virol.* 73:958-64, 1999; Zimmermann et al., *J. Virol.* 71:4145-9, 1997), (2) increased sensitivity to interferon (Zimmermann et al., *J. Virol.* 71:4145-9, 1997), (3) temperature sensitivity (Whitehead et al., *Virology* 247:232-9, 1998), (4) a general restriction in level of replication (Men et al., *J. Virol.* 70:3930-7, 1996; Muster et al., *Proc. Natl. Acad. Sci. USA* 88:5177-5181, 1991), and/or (5) host specific restriction of replication (Cahour et al., *Virology* 207:68-76, 1995). These attenuating mutations can be achieved in various ways to produce an attenuated human-bovine chimeric RSV of the invention, for example by point mutations, exchanges of sequences between related viruses, or deletions.

In yet additional alternative methods provided herein, a heterologous gene or genome segment may be added or substituted at a position corresponding to a wild-type gene order position of a counterpart gene or genome segment within the partial or complete RSV background genome or antigenome. In other embodiments, the heterologous gene or genome segment is added or substituted at a position that is more promoter-proximal or promoter-distal compared to a wild-type gene order position of a counterpart gene or genome segment within the background genome or antigenome, to enhance or reduce expression, respectively, of the heterologous gene or genome segment.

In general aspects of the invention, bovine genes or genome segments may be added to or substituted within a human RSV background to form an attenuated, human-bovine chimeric RSV. Alternatively, the chimera may be comprised of one or more human gene(s) or genome segment(s) added to or substituted within a bovine RSV background to form an attenuated RSV vaccine candidate. In this context, a chimeric RSV genome or antigenome is formed of a partial or complete bovine RSV background genome or antigenome combined with a heterologous gene or genome segment from a human RSV. The chimeric RSV thus formed may incorporate a heterologous gene or genome segment from a subgroup A or subgroup B human RSV, or from a specific human RSV strain. In preferred aspects, one or more human RSV glycoprotein genes F, G and, SH or a genome segment encoding a cytoplasmic domain, transmembrane domain, ectodomain or immunogenic epitope of a human RSV glycoprotein gene is substituted for a counterpart gene or genome segment within the bovine RSV background genome or antigenome.

In exemplary embodiments one or both of the human RSV glycoprotein genes F and G is/are substituted to replace one or both counterpart F and G glycoprotein genes in a bovine RSV background genome or antigenome. In a specific example described below, both human RSV glycoprotein genes F and G are substituted to replace counterpart F and G glycoprotein genes in the bovine RSV background genome or antigenome. In a parallel fashion, the chimeric human-bovine RSV of the invention can be readily designed to incorporate antigenic determinants from more than one RSV strain or subgroup, e.g., both human RSV subgroup A and subgroup B.

In additional aspects of the invention, attenuated, human-bovine chimeric RSV are produced in which the chimeric genome or antigenome is further modified by introducing one or more attenuating mutations specifying an attenuating phenotype in the resultant virus or subviral particle. These attenuating mutations may be generated de novo and tested for attenuating effects according to a rational design mutagenesis strategy. Alternatively, the attenuating mutations may be identified in existing biologically derived mutant RSV and thereafter incorporated into a human-bovine chimeric RSV of the invention.

The invention provides a new basis for the attenuation of a live virus vaccine against RSV and other pathogens, which attenuation is based in part on host range effects. Earlier studies involved swapping of an extragenic leader region of BRSV (45 nucleotides) with a corresponding sequence from HRSV (44 nucleotides) (Buchholz et al, *J. Virol.* 73:251-259, 1999). Neither sequence encodes a protein, and no significant phenotypic effect was observed. The instant disclosure provides attenuated, chimeric RSV by the introduction of genome segments, entire genes or multiple genes between HRSV and BRSV.

Host range differences between HRSV and BRSV are exemplified by the highly permissive growth of HRSV in chimpanzees compared to the barely detectable or undetectable growth of BRSV in the same animal. The chimpanzee is a widely accepted and faithful model of RSV infection and immunogenic activity in humans, exhibiting virus replication and disease comparable to that of humans. As illustrated herein below, host range differences of chimeric RSV observed in chimpanzees are correlated with host range differences observed in cell culture, providing a convenient preliminary assay.

Host range effects observed in the chimeric, human-bovine RSV of the invention are generally related to nucleotide and amino acid sequence differences observed between HRSV and BRSV. For example, the percent amino acid identity between HRSV and BRSV for each of the following proteins is: NS1 (69%), NS2 (84%), N (93%), P (81%), M (89%), SH (38%), G (30%), F (81%), M2-1 (80%), L (77%). Because of the extensive genetic divergence between HRSV and BRSV (replacement of the N gene of HRSV with that of BRSV, for example, involves approximately 26 amino acid differences), chimeric bovine-human RSV of the invention are particularly useful vaccine candidates. As exemplified herein below, replacement of the BRSV G and F glycoproteins with those of HRSV increases the permissivity of recombinant BRSV for replication in chimpanzees. The involvement of multiple genes and genome segments each conferring multiple amino acid or nucleotide differences provides a broad basis for attenuation which is highly stable to reversion. This mode of attenuation contrasts sharply to HRSV viruses attenuated by one or several point mutations, where reversion of an individual mutation will yield a significant or complete reacquisition of virulence. In addition, known attenuating point mutations in HRSV typically yield a temperature sensitive phenotype. This is because the temperature sensitive phenotype was specifically used as the first screen to identify altered progeny following exposure of HRSV to mutagens. One problem with attenuation associated with temperature sensitivity is that the virus can be overly restricted for replication in the lower respiratory tract while being under attenuated in the upper respiratory tract. This is because there is a temperature gradient within the respiratory tract, with temperature being higher (and more restrictive) in the lower respiratory tract and lower (less restrictive) in the upper respiratory tract. The ability of an attenuated virus to replicate in the upper respiratory tract can result in complications including congestion, rhinitis, fever and otitis media. Thus, attenuation achieved solely by temperature sensitive mutations may not be ideal. In contrast, host range mutations present in human-bovine chimeric RSV of the invention will not in most cases confer temperature sensitivity. Therefore, this novel method of attenuation will (i) be more stable genetically and phenotypically, and (ii) be less likely to be associated with residual virulence in the upper respiratory tract than other live vaccine approaches.

In combination with the host range phenotypic effects provided in the human-bovine chimeric RSV of the invention, it is often desirable to adjust the attenuation phenotype by introducing additional mutations that increase or decrease attenuation of the chimeric virus. Thus, candidate vaccine strains can be further attenuated by incorporation of at least one, and preferably two or more different attenuating mutations, for example mutations identified from a panel of known, biologically derived mutant RSV strains. Preferred human mutant RSV strains are cold passaged (cp) and/or temperature sensitive (ts) mutants, for example the mutants designated "cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579)" (each deposited under the terms of the Budapest Treaty with the American Type Culture Collection (ATCC) of 10801 University Boulevard, Manassas, Va. 20110-2209, U.S.A., and granted the above identified accession numbers). From this exemplary panel of biologically derived mutants, a large "menu" of attenuating mutations are provided which can each be combined with any other mutation(s) within the panel for calibrating the level of attenuation in the recombinant, human-bovine chimeric RSV for vaccine use. Additional mutations may be derived from RSV having non-ts and non-cp attenuating mutations as identified, e.g., in small plaque (sp), cold-adapted (ca) or host-range restricted (hr) mutant strains. The mutations may be incorporated in either a human or bovine antigenomic sequence, and attenuating mutations identified in a human, bovine or other RSV mutant may be transferred to the heterologous RSV recipient (e.g., bovine or human RSV, respectively) by mapping the mutation to the corresponding, homologous site in the recipient genome and mutating the native sequence in the recipient to the mutant genotype (either by an identical or conservative mutation), as described in U.S. Provisional Patent Application No. 60/129, 006, filed by Murphy et al. on Apr. 13, 1999, incorporated herein by reference.

Human-bovine chimeric RSV designed and selected for vaccine use often have at least two and sometimes three or more attenuating mutations to achieve a satisfactory level of attenuation for broad clinical use. In one embodiment, at least one attenuating mutation occurs in the RSV polymerase gene L (either in the donor or recipient gene) and involves one or more nucleotide substitution(s) specifying an amino acid change in the polymerase protein specifying an attenuation phenotype which may or may not involve a temperature-sensitive (ts) phenotype. Chimeric RSV of the invention may incorporate an attenuating mutation in any additional RSV gene besides L, e.g., in the M2 gene. However, preferred human-bovine chimeric RSV in this context incorporate one or more nucleotide substitutions in the large polymerase gene L resulting in an amino acid change at amino acid Asn43, Cys319, Phe 521, Gln831, Met1169, Tyr1321 and/or His 1690 in the RSV polymerase gene L, as exemplified by the changes, Ile for Asn43, Leu for Phe521, Leu for Gln831, Val for Met1169, and Asn for Tyr1321. Other alternative amino acid changes, particularly conservative changes with respect to identified mutant residues, at these positions can of course be made to yield a similar effect as the identified, mutant substitution. Additional desired mutations for incorporation into human-bovine chimeric RSV of the invention include attenuating mutations specifying an amino acid substitution at Val267 in the RSV N gene, Glu218 and/or Thr523 in the RSV F gene, and a nucleotide substitution in the gene-start sequence of gene M2. Any combination of one or more attenuating mutations identified herein, up to and including a full complement of these mutations, may be incorporated in human-bovine chimeric RSV to yield a suitably attenuated recombinant virus for use in selected populations or broad populations of vaccine recipients.

Attenuating mutations for incorporation in human-bovine chimeric RSV of the invention may be selected in coding portions of a donor or recipient RSV gene or in non-coding regions such as a cis-regulatory sequence. Exemplary non-coding mutations include single or multiple base changes in a gene start sequence, as exemplified by a single or multiple base substitution in the M2 gene start sequence at nucleotide 7605 (nucleotide 7606 in recombinant sequence).

Infectious chimeric RSV according to the invention can incorporate heterologous, coding or non-coding nucleotide sequences from any RSV or RSV-like virus, e.g., human, bovine, murine (pneumonia virus of mice), or avian (turkey rhinotracheitis virus) pneumovirus, or from another enveloped virus, e.g., parainfluenza virus (PIV). Exemplary heterologous sequences include RSV sequences from one human RSV strain combined with sequences from a different human RSV strain in a human-bovine chimeric RSV. For example, chimeric RSV of the invention may incorporate sequences from two or more wild-type or mutant RSV strains, for example mutant strains selected from cpts RSV 248, cpts 248/404, cpts 248/955, cpts RSV 530, cpts 530/1009, or cpts 530/1030. Alternatively, human-bovine chimeric RSV may incorporate sequences from two or more, wild-type or mutant human RSV subgroups, for example a combination of human RSV subgroup A and subgroup B sequences. In yet additional aspects, one or more human RSV coding or non-coding polynucleotides are substituted with a counterpart sequence from a heterologous RSV or non-RSV virus, alone or in combination with one or more selected attenuating mutations, e.g., cp and/or ts mutations, to yield novel attenuated vaccine strains.

Mutations incorporated within chimeric cDNAs, vectors and viral particles of the invention can be introduced individually or in combination into a full-length human-bovine chimeric RSV cDNA and the phenotypes of rescued virus containing the introduced mutations can be readily determined. In exemplary embodiments, amino acid changes displayed by attenuated, biologically-derived viruses versus a wild-type RSV, for example changes exhibited by cpRSV or tsRSV, are incorporated in combination within a recombinant human-bovine chimeric RSV to yield a desired level of attenuation.

In yet additional aspects of the invention, chimeric human-bovine RSV can be readily designed as "vectors" to incorporate antigenic determinants from different pathogens, including more than one RSV strain or group (e.g., both human RSV A and RSV B subgroups), human parainfluenza virus (HPIV) including HPIV3, HPIV2 and HPIV1, measles virus and other pathogens (see, e.g., U.S. Provisional Patent Application Ser. No. 60/170,195; U.S. patent application Ser. No. 09/458,813; and U.S. patent application Ser. No. 09/459,062, each incorporated herein by reference). Within various embodiments, the bovine-human chimeric genome or antigenome comprises a partial or complete RSV "vector genome or antigenome" combined with one or more heterologous genes or genome segments encoding one or more antigenic determinants of one or more heterologous pathogens. The heterologous pathogen may be a heterologous RSV (i.e., a RSV of a different strain or subgroup), and the heterologous gene or genome segment may encode a RSV NS1, NS2, N, P, M, SH, M2(ORF1), M2(ORF2), L, F or G protein or fragment (e.g., a immunogenic domain or epitope) thereof. For example, the vector genome or antigenome may be a partial or complete RSV A genome or antigenome and the heterologous gene(s) or genome segment(s) may encode antigenic determinant(s) of a RSV B subgroup virus.

In alternative embodiments, the human-bovine chimeric RSV vector genome or antigenome is a partial or complete BRSV genome or antigenome and the heterologous gene(s) or genome segment(s) encoding the antigenic determinant(s) is/are of one or more HRSV(s). For example, the partial or complete BRSV genome or antigenome may incorporate one or more gene(s) or genome segment(s) encoding one or more HRSV glycoprotein genes selected from F, G and SH, or one or more genome segment(s) encoding cytoplasmic domain, transmembrane domain, ectodomain or immunogenic epitope portion(s) of F, G, and/or SH of HRSV.

In other alternate embodiments, human-bovine chimeric RSV designed as "vectors" for carrying heterologous antigenic determinants incorporate one or more antigenic determinants of a non-RSV pathogen, such as a human parainfluenza virus (HPIV). In one exemplary embodiment, one or more HPIV1, HPIV2, or HPIV3 gene(s) or genome segment(s) encoding one or more HN and/or F glycoprotein(s) or antigenic domain(s), fragment(s) or epitope(s) thereof is/are added to or incorporated within the partial or complete HRSV vector genome or antigenome. In more detailed embodiments, a transcription unit comprising an open reading frame (ORF) of an HPIV1, HPIV2, or HPIV3 HN or F gene is added to or incorporated within the chimeric HRSV vector genome or antigenome.

In yet additional alternate embodiments, the vector genome or antigenome comprises a partial or complete HRSV or BRSV genome or antigenome and the heterologous pathogen is selected from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses. Based on this exemplary list of candidate pathogens, the selected heterologous antigenic determinant(s) may be selected from measles virus HA and F proteins, subgroup A or subgroup B respiratory syncytial virus F, G, SH and M2 proteins, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein; filovirus G protein, bunyavirus G protein, Flavivirus E and NS1 proteins, and alphavirus E protein, and antigenic domains, fragments and epitopes thereof. In one embodiment, the heterologous pathogen is measles virus and the heterologous antigenic determinant(s) is/are selected from the measles virus HA and F proteins and antigenic domains, fragments and epitopes thereof. To achieve such a chimeric construct, a transcription unit comprising an open reading frame (ORF) of a measles virus HA gene may be added to or incorporated within a HRSV vector genome or antigenome.

The present invention thus provides human-bovine chimeric RSV clones, polynucleotide expression constructs (also referred to as vectors) and particles which can incorporate multiple, phenotype-specific mutations introduced in selected combinations into the chimeric genome or antigenome to produce an attenuated, infectious virus or subviral particle. This process coupled with routine phenotypic evaluation provides human-bovine chimeric RSV having such desired characteristics as attenuation, temperature sensitivity, altered immunogenicity, cold-adaptation, small plaque size, host range restriction, etc. Mutations thus identified are compiled into a "menu" and introduced in various combinations to calibrate a vaccine virus to a selected level of attenuation, immunogenicity and stability.

In yet additional aspects of the invention, human-bovine chimeric RSV, with or without attenuating mutations, are constructed to have a nucleotide modification to yield a desired phenotypic, structural, or functional change. Typically, the selected nucleotide modification will specify a phenotypic change, for example a change in growth characteristics, attenuation, temperature-sensitivity, cold-adaptation, plaque size, host range restriction, or immunogenicity. Structural changes in this context include introduction or ablation of restriction sites into RSV encoding cDNAs for ease of manipulation and identification.

In preferred embodiments, nucleotide changes within human-bovine chimeric RSV include modification of a viral gene by deletion of the gene or ablation of its expression. Target genes for mutation in this context include the attachment (G) protein, fusion (F) protein, small hydrophobic (SH), RNA binding protein (N), phosphoprotein (P), the large polymerase protein (L), the transcription elongation factor (M2 ORF1), the RNA regulatory factor M2 ORF2, the matrix (M) protein, and two nonstructural proteins, NS1 and NS2. Each of these proteins can be selectively deleted, substituted or rearranged, in whole or in part, alone or in combination with other desired modifications, to achieve novel chimeric RSV recombinants.

In one aspect of the invention, an SH, NS1, NS2, G or M2-2 gene is modified in the human-bovine chimeric RSV. For example, each of these genes may be deleted or its expression ablated (e.g., by introduction of a stop codon) to alter the phenotype of the resultant human-bovine chimeric RSV clone to improve growth, attenuation, immunogenicity or other desired phenotypic characteristics. For example, deletion of the SH gene in the background or heterologous (i.e. recipient or donor, respectively) portion of the recombinant genome or antigenome will yield a chimeric RSV having novel phenotypic characteristics such as enhanced growth in vitro and/or attenuation in vivo. In a related aspect, an SH gene deletion, or deletion of another selected non-essential gene or genome segment such as a NS1, NS2, G or M2-2 gene deletion is constructed in a human-bovine chimeric RSV, alone or in combination with one or more different mutations specifying an attenuated phenotype, e.g., a point mutation adopted directly (or in modified form, e.g., by introducing multiple nucleotide changes in a codon specifying the mutation) from a biologically derived attenuated RSV mutant. For example, the SH, NS1, NS2, G or M2-2 gene may be deleted in combination with one or more cp and/or ts mutations adopted from cpts248/404, cpts530/1009, cpts530/1030 or another selected mutant RSV strain, to yield a chimeric RSV having increased yield of virus, enhanced attenuation, improved immunogenicity and genetic resistance to reversion from an attenuated phenotype due to the combined effects of the different mutations.

Alternative nucleotide modifications can include a deletion, insertion, addition or rearrangement of a cis-acting regulatory sequence for a selected gene in the human-bovine chimera. In one example, a cis-acting regulatory sequence of one RSV gene is changed to correspond to a heterologous regulatory sequence, which may be a counterpart cis-acting regulatory sequence of the same gene in a different RSV or a cis-acting regulatory sequence of a different RSV gene. For example, a gene end signal may be modified by conversion or substitution to a gene end signal of a different gene in the same RSV strain. In other embodiments, the nucleotide modification may comprise an insertion, deletion, substitution, or rearrangement of a translational start site within the chimeric genome or antigenome, e.g., to ablate an alternative translational start site for a selected form of a protein. In one example, the translational start site for a secreted form of the RSV G protein is ablated to modify expression of this form of the G protein and thereby produce desired in vivo effects.

In addition, a variety of other genetic alterations can be produced in a human-bovine chimeric RSV genome or antigenome, alone or together with one or more attenuating mutations adopted from a biologically derived mutant RSV. For example, genes or genome segments from non-RSV sources may be inserted in whole or in part. Alternatively, the order of genes can be changed, gene overlap removed, or an RSV genome promoter replaced with its antigenome counterpart. Different or additional modifications in the chimeric genome or antigenome can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences. In yet additional aspects, polynucleotide molecules or vectors encoding the chimeric RSV genome or antigenome can be modified to encode non-RSV sequences, e.g., a cytokine, a T-helper epitope, a restriction site marker, or a protein of a microbial pathogen (e.g., virus, bacterium or fungus) capable of eliciting a protective immune response in an intended host. In one such embodiment, human-bovine chimeric RSV are constructed that incorporate a gene or genome segment from a parainfluenza virus (PIV), for example a PIV HN or F glycoprotein or an immunogenic domain or epitope thereof.

All of the foregoing modifications within the human-bovine chimeric RSV genome or antigenome, including nucleotide insertions, rearrangements, deletions or substitutions yielding point mutations, site-specific nucleotide changes, and changes involving entire genes or genome segments, may be made to either the heterologous donor gene or genome segment, or the recipient, background genome or antigenome. In each case, these alterations will preferably specify one or more phenotypic change(s) in the resulting recombinant RSV, such as a phenotypic change that results in attenuation, temperature-sensitivity, cold-adaptation, small plaque size, host range restriction, alteration in gene expression, or a change in an immunogenic epitope.

In another aspect of the invention, compositions (e.g., isolated polynucleotides and vectors incorporating an RSV-encoding cDNA) and methods are provided for producing an isolated infectious human-bovine chimeric RSV. Using these compositions and methods, infectious chimeric RSV particles or subviral particles are generated from a human-bovine chimeric RSV genome or antigenome coexpressed with a nucleocapsid (N) protein, a nucleocapsid phosphoprotein (P), a large (L) polymerase protein, and an RNA polymerase elongation factor. In related aspects of the invention, compositions and methods are provided for introducing the aforementioned structural and phenotypic changes into a recombinant human-bovine chimeric RSV yield infectious, attenuated vaccine viruses.

In one embodiment, an expression vector is provided which comprises an isolated polynucleotide molecule encoding a human-bovine chimeric RSV genome or antigenome. Also provided is the same or different expression vector comprising one or more isolated polynucleotide molecules encoding N, P, L and RNA polymerase elongation factor proteins. Then proteins also can be expressed directly from the genome or antigenome cDNA. The vector(s) is/are preferably expressed or coexpressed in a cell or cell-free lysate, thereby producing an infectious human-bovine chimeric RSV particle or subviral particle.

The RSV genome or antigenome and the N, P, L and RNA polymerase elongation factor (preferably the product of the M2(ORF1) of RSV) proteins can be coexpressed by the same or different expression vectors. In some instances the N, P, L and RNA polymerase elongation factor proteins are each encoded on different expression vectors. The polynucleotide molecule encoding the human-bovine chimeric RSV genome or antigenome is a chimera of human and bovine polynucleotide sequences operably joined to allow production of infectious virus or viral particles therefrom. In alternative aspects of the invention, the human-bovine chimeric RSV genome or antigenome can include sequences from multiple human RSV strains or subgroups (A and B), as well as other non-human (e.g., murine) RSV sequences. In other alternate aspects, the human-bovine chimeric RSV genome or antigenome can incorporate non-RSV sequences, for example a polynucleotide containing sequences from human and bovine RSV operably joined with a nucleotide or polynucleotide encoding a point mutation, protein, protein domain or immunogenic epitope of PIV or another negative stranded RNA virus.

The above methods and compositions for producing human-bovine chimeric RSV yield infectious viral or subviral particles, or derivatives thereof. An infectious virus is comparable to the authentic RSV virus particle and is infectious as is. It can directly infect fresh cells. An infectious subviral particle typically is a subcomponent of the virus particle which can initiate an infection under appropriate conditions. For example, a nucleocapsid containing the genomic or antigenomic RNA and the N, P, L and M2(ORF1) proteins is an example of a subviral particle which can initiate an infection if introduced into the cytoplasm of cells. Subviral particles provided within the invention include viral particles which lack one or more protein(s), protein segment(s), or other viral component(s) not essential for infectivity.

In other embodiments the invention provides a cell or cell-free lysate containing an expression vector which comprises an isolated polynucleotide molecule encoding a human-bovine chimeric RSV genome or antigenome as described above, and an expression vector (the same or different vector) which comprises one or more isolated polynucleotide molecules encoding the N, P, L and RNA polymerase elongation factor proteins of RSV. One or more of these proteins also can be expressed from the genome or antigenome cDNA. Upon expression the genome or antigenome and N, P, L, and RNA polymerase elongation factor proteins combine to produce an infectious human-bovine chimeric RSV viral or subviral particle.

Attenuated human-bovine chimeric RSV of the invention is capable of eliciting a protective immune response in an infected human host, yet is sufficiently attenuated so as to not cause unacceptable symptoms of severe respiratory disease in the immunized host. The attenuated chimeric virus or subviral particle may be present in a cell culture supernatant, isolated from the culture, or partially or completely purified. The virus may also be lyophilized, and can be combined with a variety of other components for storage or delivery to a host, as desired.

The invention further provides novel vaccines comprising a physiologically acceptable carrier and/or adjuvant and an isolated attenuated human-bovine chimeric RSV. In one embodiment, the vaccine is comprised of a human-bovine chimeric RSV having at least one, and preferably two or more attenuating mutations or other nucleotide modifications as described above. The vaccine can be formulated in a dose of $10^3$ to $10^6$ PFU of attenuated virus. The vaccine may comprise attenuated chimeric virus that elicits an immune response against a single RSV strain or antigenic subgroup, e.g. A or B, or against multiple RSV strains or subgroups. In this regard, human-bovine chimeric RSV of the invention can individually elicit a monospecific immune response or a polyspecific immune response against multiple RSV strains or subgroups. Human-bovine chimeric RSV can be combined in vaccine formulations with other chimeric RSV or non-chimeric RSV having different immunogenic characteristics for more effective protection against one or multiple RSV strains or subgroups.

In related aspects, the invention provides a method for stimulating the immune system of an individual to elicit an immune response against one or more strains or subgroups of RSV in a mammalian subject. The method comprises administering a formulation of an immunologically sufficient amount of an attenuated, human-bovine chimeric RSV in a physiologically acceptable carrier and/or adjuvant. In one embodiment, the immunogenic composition is a vaccine comprised of human-bovine chimeric RSV having at least one, and preferably two or more attenuating mutations or other nucleotide modifications specifying a desired phenotype as described above. The vaccine can be formulated in a dose of $10^3$ to $10^6$ PFU of attenuated virus. The vaccine may comprise attenuated human-bovine chimeric RSV virus that elicits an immune response against a single RSV strain or antigenic subgroup, e.g. A or B, or against multiple RSV strains or subgroups. In this context, the human-bovine chimeric RSV can elicit a monospecific immune response or a polyspecific immune response against multiple RSV strains or subgroups. Alternatively, human-bovine chimeric RSV having different immunogenic characteristics can be combined in a vaccine mixture or administered separately in a coordinated treatment protocol to elicit more effective protection against one RSV strain, or against multiple RSV strains or subgroups. Preferably the immunogenic composition is administered to the upper respiratory tract, e.g., by spray, droplet or aerosol. Often, the composition will be administered to an individual seronegative for antibodies to RSV or possessing transplacentally acquired maternal antibodies to RSV.

BRIEF DESCRIPTION OF THE DRAWINGS

FIGS. 1A and 1B depict replacement of the G and F genes of recombinant (r) bovine RSV (BRSV) strain ATue51908 with the G and F genes of the human RSV (HRSV) strain A2 to create the recombinant chimeric virus rBRSV/A2.

FIG. 1A is a diagram of the rBRSV genome, illustrating the replacement of the F and G genes with those of HRSV. The location of the open reading frames (ORFs) are shown as shaded (BRSV) or open (HRSV) rectangles. The G and F genes are shown as enlargements, in which gene end/polyadenylation signals are represented by bars, gene start signals are shown as filled triangles, and the positions of synthetic restriction sites serving as genetic markers or as boundaries of swapped restriction fragments are indicated by arrowheads with the position in the complete antigenome sequence shown underneath. The size of the fragments framed by the marker restriction sites is indicated in parentheses. The genome length of the recombinant viruses is indicated on the left. The roman numerals (I, II and III) refer to intergenic regions which are expanded in FIG. 1B.

FIG. 1B illustrates alignment of the SH/G (I), G/F (II), and F/M2 (III) intergenic regions of a biologically-derived BRSV strain ATue51908 (top line); the recombinant version, rBRSV ATue51908 (second line), a recombinant chimeric virus rBRSV/A2 (third line), and biologically derived HRSV strain A2 (bottom line). FIG. 1B, Panel I: SH/G intergenic region: ATue51908 (top line) (SEQ ID NO. 1); rBRSV (second line) (SEQ ID NO. 2); rBRSV/A2 (third line) (SEQ ID NO. 3); HRSV strain A2 (bottom line) (SEQ ID NO. 4). FIG. 1B, Panel II: G/F intergenic region: ATue 51908 (top line) (SEQ ID NO. 5); rBRSV (second line) (SEQ ID NO. 6); rBRSV/A2 (third line) (SEQ ID NO. 7); HRSV A2 (bottom line) (SEQ ID NO. 8). FIG. 1B, Panel 3: F/M2 intergenic region: ATue51908 (top line) (SEQ ID NO. 9); rBRSV (second line) (SEQ ID NO. 10); rBRSV/A2 (third line) (SEQ ID NO. 11); HRSV A2 (SEQ ID NO. 12). The sequences are shown as DNA positive strand. Gaps are indicated by dots, gene start and gene end signals are shaded, and translation start codons are in bold. Hash marks indicate nucleotide identity. Restriction sites are indicated, with recognition sequences shaded. Orf is open reading frame. Numbering refers to the genomic positions (for BRSV, strain ATue51908: GenBank accession no. AF092942; for HRSV strain A2: GenBank accession no. M74568).

FIGS. 2A-2C demonstrate marker restriction sites in the genomes of biologically derived BRSV (ATue51908); its recombinant version rBRSV, and the recombinant chimera rBRSV-A2. RT-PCR was performed on total RNA of BSR T7/5 cells infected with the indicated virus. The PCR products were subjected to restriction analysis and analyzed on a 2% (FIGS. 2A, 2B) or 3% agarose gel (FIG. 2C). Nucleotide lengths are estimates based on calculated sizes. In all cases, a PCR product was not detected when the RT step was omitted. M, 1 kb DNA ladder (Life Technologies, Gaithersburg, Md.). The size of some marker fragments is indicated on the right.

FIG. 2A shows an analysis of RT-PCR products corresponding to positions 3612 to 4886 (ATue51908 and rBRSV) or positions 3612 to 4885 (rBRSV/A2), encompassing the SalI site (position 4673) contained in the SH/G intergenic regions of the recombinant virus isolates. The PCR products corresponding to the predicted size of approximately 1,273-1274 bp were digested with SalI. This did not cleave the biologically-derived ATue51908, which lacked this introduced site, whereas for the recombinant viruses this resulted in bands of 1,061 bp (both viruses) and 213 bp (rBRSV) or 212 bp (rBRSV/A2).

FIG. 2B shows an analysis of RT-PCR products corresponding to positions 5372 to 5964 (ATue51908 and rBRSV) or positions 5452 to 6062 (rBRSV/A2), containing the G/F intergenic regions and the respective marker restriction sites in the recombinant viruses (an SphI site at rBRSV position 5539 or a StuI site in rBRSV-A2 position 5619). The PCR products were of the expected size of approximately 592 (ATue51908 and rBRSV) or 610 (rBRSV/A2). SphI digested only rBRSV, as predicted, resulting in fragments of 425 bp and 167 bp. StuI digested only rBRSV/A2, as predicted, resulting in fragments of 443 bp and 167 bp.

FIG. 2C shows an analysis of RT-PCR products spanning positions 7218 to 7852 (ATue51908 and rBRSV) or 7316 to 7939 (rBRSV/A2), containing the F/M2 intergenic region. As predicted, digestion with XhoI did not cleave ATue51908 but in the case of rBRSV and rBRSV/A2 resulted in fragments of 395 bp (both viruses) and 267 bp (rBRSV) or 256 bp (rBRSV/A2). This revealed the presence of the introduced XhoI site (rBRSV position 7471, rBRSV-A2 position 7558) in the genomes of the recombinant viruses.

FIGS. 7A and 7B depict replacement of the F gene of rBRSV strain ATue51908 with the F gene of HRSV strain Long to create the recombinant chimeric virus rBRSV/LongF.

FIG. 7A is a diagram of the rBRSV genome illustrating the replacement of the F gene with that of HRSV strain Long. The location of the open reading frames (ORFs) are shown as shaded (BRSV) or open (HRSV) rectangles. The F gene is shown as an enlargement, in which gene end/polyadenylation signals are represented by bars, gene start signals are shown as filled triangles, and the positions of synthetic restriction sites serving as genetic markers or as boundaries of swapped restriction fragments are indicated by arrowheads with the position in the complete antigenome sequence shown underneath. The size of the fragments framed by the marker restriction sites is indicated (in parentheses). The genome length of the recombinant viruses is indicated on the left. The roman numerals (I, II and III) refer to intergenic regions which are expanded in FIG. 8B.

FIG. 7B shows alignment of the SH/G (I), G/F (II), and F/M2 (III) intergenic regions of biologically derived BRSV strain ATue51908 (top line); the recombinant version, rBRSV ATue51908 (second line), and the recombinant chimeric virus rBRSV/LongF (bottom line). Annotations are as in FIG. 1. FIG. 7B, Panel I: SH/G intergenic region: ATue51908 (top line) (SEQ ID NO. 1); rBRSV (second line) (SEQ ID NO. 2); rBRSV/LongF (third line) (SEQ ID NO. 2). FIG. 7B, Panel II: G/F intergenic region: ATue 51908 (top line) (SEQ ID NO. 5); rBRSV (second line) (SEQ ID NO. 6); rBRSV/LongF (third line) (SEQ ID NO. 13). FIG. 7B, Panel 3: F/M2 intergenic region: ATue51908 (top line) (SEQ ID NO. 9); rBRSV (second line) (SEQ ID NO. 10); rBRSV/A2 (third line) (SEQ ID NO. 11).

FIG. 10 details construction of a chimeric rBRSV/HRSV genome in which the BRSV G and F genes have been deleted and the G and F genes of HRSV have been placed in a promoter-proximal position. BRSV genes are shaded; HRSV genes are clear. Nucleotide sequence position numbers are relative to the complete rBRSV antigenome (Buchholz et al., J. Virol. 73:251-259, 1999; Buchholz et al., J. Virol. 74:1187-1199, 2000; GenBank accession number AF092942 or complete rHRSV antigenome in Collins et al., Proc. Natl. Acad. Sci. USA 92:11563-11567, 1995; each incorporated herein by reference); sequence position numbers that refer to the HRSV sequence are underlined. FIG. 10, panel A details structure of rBRSV containing NotI, SalI and XhoI sites that were added in previous work (Buchholz et al., J. Virol. 73:251-259, 1999; Buchholz et al., J. Virol. 74:1187-1199, 2000). FIG. 10, panel B depicts modifications to rBRSV to create rBRSV/A2-G1F2. The BRSV G and F genes were deleted by digestion with SalI and XhoI and religation of the resulting compatible cohesive ends. The region of the genome of HRSV from nucleotides 4692 to 7557, containing the G and F genes, was amplified by PCR using primers that contained desired changes to be incorporated into each end of the cDNA. The amplified PCR product contained (in upstream to downstream order): a NotI site, a BlpI site, the complete HRSV G ORF, its downstream noncoding and GE signal, the HRSV G-F IG sequence, the complete HRSV F gene, 6 nucleotides from the HRSV F-M2 IG sequence (CACAAT), the NS1 GS signal, a BlpI site and a NotI site. This cDNA was cloned into the unique NotI site at position 67 of rBRSV. FIG. 10, panel C illustrates structure of the genomic RNA of rBRSV/A2-G1 F2.

FIG. 13 details construction of a chimeric rBRSV/HRSV containing the M, G and F genes of HRSV. BRSV genes are shaded; HRSV genes are clear. Sequence position numbers that refer to HRSV genes are underlined. FIG. 13, panel A depicts modification of rBRSV/A2 to contain a unique MluI site at position 3204, within the intergenic region between the P and M genes (P-M IG). The sequence of the IG is shown, with small case letters indicating the original nucleotide assignments. The underlined letters indicate the MluI site created by the 5 nucleotide substitutions. Nucleotide sequence position numbers are relative to the complete rBRSV antigenome (Buchholz et al., J. Virol. 73:251-259, 1999; Buchholz et al., J. Virol. 74:1187-1199, 2000; GenBank accession number AF092942 or complete rHRSV antigenome in Collins et al., *Proc. Natl. Acad. Sci. USA* 92:11563-11567, 1995); sequence position numbers that refer to the HRSV sequence are underlined. FIG. 13, panel B illustrates modification of rBRSV/A2 to create rBRSV/A2-MGF. The MluI-SalI fragment containing the BRSV M and SH genes was excised and replaced with an MluI-SalI fragment containing the HRSV M gene. The MluI-SalI fragment containing the HRSV M gene is shown in the box. Also shown is the sequence immediately upstream of the MluI site (SEQ ID NO. 17), including the BRSV P gene-end sequence, and the sequence immediately downstream of the SalI site (SEQ ID NO. 18), including the intergenic sequence between the M and G genes (M-G IG), the HRSV G gene-start signal, and the ATG (bold, italics) that begins the G ORF. FIG. 13, panel C depicts the structure of the genome of rBRSV/A2-MGF.

DESCRIPTION OF THE SPECIFIC EMBODIMENTS

Figure 1A:
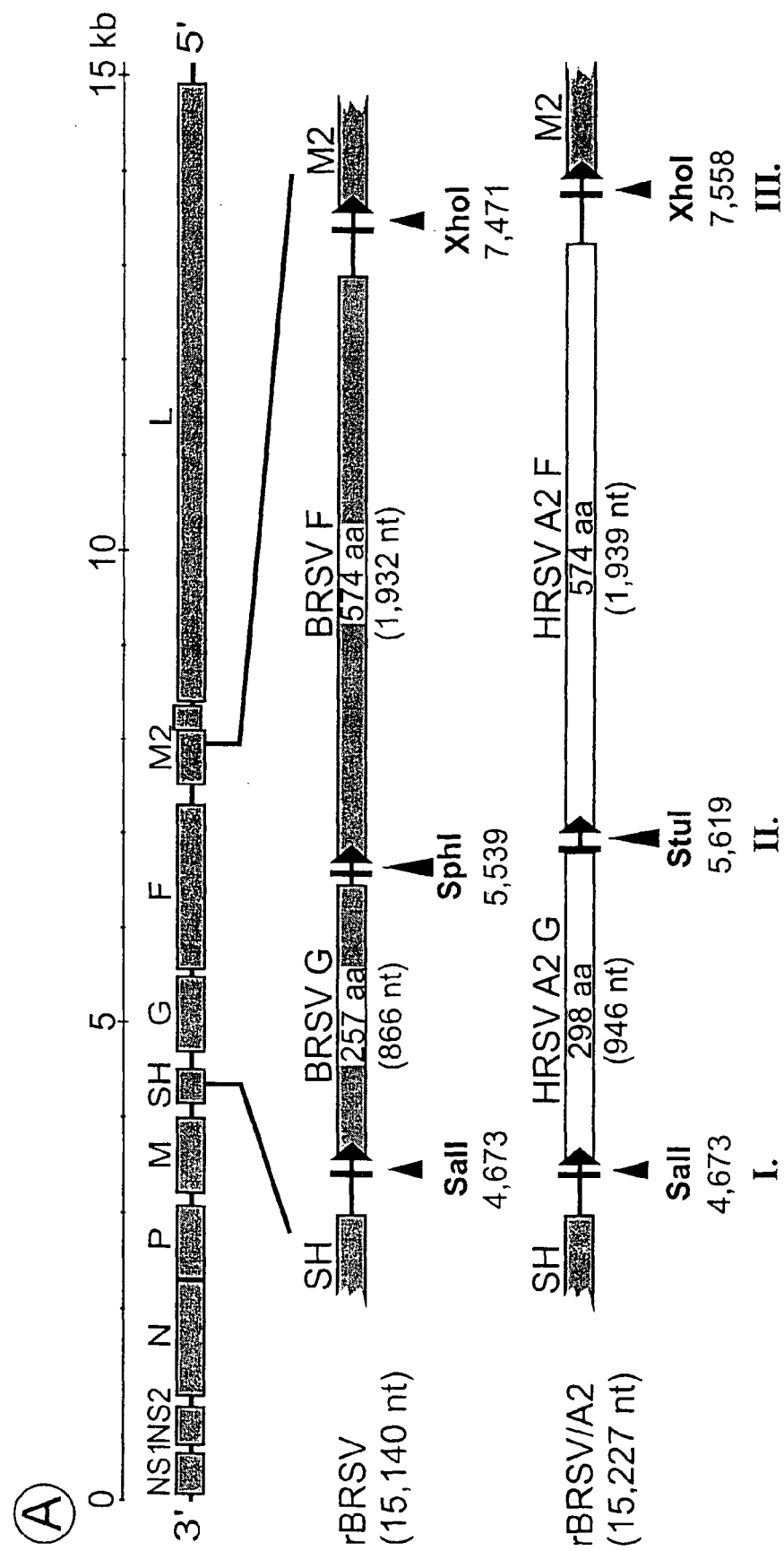

The present invention provides recombinant respiratory syncytial virus (RSV) cloned as a chimera of human and bovine RSV genomic or antigenomic sequences to yield a human-bovine chimeric RSV. The chimeric construction of human-bovine RSV yields a viral particle or subviral particle that is infectious in mammals, particularly humans, and useful for generating immunogenic compositions for clinical use. Also provided within the invention are novel methods and compositions for designing and producing attenuated, human-bovine chimeric RSV, as well as methods and compositions for the prophylaxis and treatment of RSV infection. Human-bovine chimeric RSV and immunogenic compositions according to the invention may elicit an immune response to a specific RSV subgroup or strain, or they may elicit a polyspecific response against multiple RSV subgroups or strains.

RSV is generally characterized as an enveloped nonsegmented negative strand RNA virus of the paramyxovirus family (Collins, et al., *Fields Virology* 2:1313-1352, 1996). Its genome, which is 15,222 nucleotides (nt) in length for the well known strain A2, is transcribed into 10 messenger RNAs that encode 11 proteins (Collins, et al., *Fields Virology* 2:1313-1352, 1996; Atreya, et al., *J. Virol.* 72:1452-61, 1998; Bukreyev, et al., *J. Virol.* 71:8973-82, 1997; Collins, et al., *Proc. Natl. Acad. Sci. USA* 93:81-5, 1996; Teng and Collins, *J. Virol.* 72:5707-16, 1998; Teng and Collins, *J. Virol.* 73:466-473, 1999; Whitehead, et al., *J. Virol.* 73:3438-42, 1999, each incorporated herein by reference). Four of these are nucleocapsid/polymerase proteins, namely the major nucleocapsid N protein, the phosphoprotein P, and polymerase protein L, and the transcription antitermination protein M2-1. Three are surface glycoproteins, namely the attachment G protein, the fusion F glycoprotein responsible for penetration and syncytium formation, and the small hydrophobic SH protein of unknown function. The matrix M protein is an internal virion protein involved in virion formation. There are two nonstructural proteins NS1 and NS2 of unknown function. Finally, there is a second open reading frame (ORF) in the M2 mRNA which encodes an RNA regulatory factor M2-2.

The G and F proteins are the major neutralization and protective antigens (Collins, et al., *Fields Virology* 2:1313-1352, 1996; Connors, et al., *J. Virol.* 66:1277-81, 1992). Resistance to reinfection by RSV is largely mediated by serum and mucosal antibodies specific against these proteins. RSV-specific cytotoxic T cells are also induced by RSV infection and can be directed against a number of different proteins, but this effector has not yet been shown to be an important contributor to long term resistance to reinfection. However, both CD8+ and CD4+ cells can be important in regulating the immune response, and both may be involved in viral pathogenesis (Johnson, et al., *J. Virol.* 72:2871-80, 1998; Srikiatkhachorn and Braciale, *J. Exp. Med.* 186:421-32, 1997). Thus, F and G are the most important antigenic determinants, but other proteins can also play important roles in the immune response.

RSV isolates can be segregated into two antigenic subgroups, A and B, by reactivity with monoclonal antibodies (Anderson, et al., *J. Infect. Dis.* 151:626-33, 1985, Mufson, et al., *J. Gen. Virol.* 66:2111-24, 1985). The two subgroups exhibit differences across the genome, but are the most divergent in the ectodomain of the G protein where the percent amino acid sequence divergence can exceed 50% and the antigenic divergence is 95% based on reactivity of monospecific polyclonal antisera (Johnson, et al., *Proc. Natl. Acad. Sci. USA* 84:5625-9, 1987; Johnson, et al., *J. Virol.* 61:3163-6, 1987). The F protein is approximately 10% divergent by amino acid sequence and 50% divergent antigenically between RSV A and B subgroups (Johnson, et al., *J. Virol.* 61:3163-6, 1987; Johnson and Collins, *J. Gen. Virol.* 69:2623-8, 1988). Thus, both subgroups should be represented in a vaccine.

Bovine RSV (BRSV) is related to human RSV (HRSV) and is a ubiquitous, commercially-important agent of respiratory tract disease in cattle (Mohanty, et al., *Am. J. Vet. Res.* 36:417-9, 1975; Van der Poel, et al., *J. Infect.* 29:215-28, 1994). The amount of sequence divergence between BRSV and HRSV is about twice as much as between the HRSV A and B subgroups noted above. Thus, the F proteins have approximately 20% amino acid divergence between BRSV and HRSV, and the G proteins approximately 70% divergence (Lerch, et al., *J. Virol.* 64:5559-69, 1990; Lerch, et al., *Virology* 181:118-31, 1991; Mallipeddi and Samal, *J. Gen. Virol.* 74:2001-4, 1993; Mallipeddi and Samal, *Vet. Microbiol.* 36:359-67, 1993; Samal et al., *Virology* 180:453-456, 1991; Samal and Zamora, *J. Gen. Virol.* 72:1717-1720, 1991; Zamora and Samal, *Virus Res.* 24:115-121, 1992; ibid, *J. Gen. Virol.* 73:737-741, 1992; Mallipeddi and Samal, *J. Gen. Virol.* 73:2441-2444, 1992, Pastey and Samal, *J. Gen. Virol.* 76:193-197, 1995; Walravens et al., *J. Gen. Virol.* 71:3009-3014, 1990; Yunnus et al., *J. Gen. Virol.* 79:2231-2238, 1998, each incorporated herein by reference). The ability to produce infectious HRSV from cDNA has been extended to allow recombinant production of BRSV, and infectious recombinant virus has thereby been produced (Buchholz, et al., *J. Virol.* 73:251-9, 1999).

BRSV has been evaluated in cotton rats (Piazza, et al., *J. Virol.* 67:1503-10, 1993), owl monkeys and chimpanzees (Prince, et al., *Animal Models of Respiratory Syncytial Virus Infections.* 1990) as a vaccine against HRSV. BRSV was highly restricted in all three experimental animals, and immune responses were very low. In rats, significant resistance to HRSV challenge was observed in one study, but the basis of this protective effect remains unclear. In monkeys, antibody responses to the BRSV vaccine were detected in only 2 of 9 animals. Upon subsequent challenge with HRSV, the duration of shedding was slightly reduced, but neither the magnitude of shedding nor disease symptoms were affected. In a parallel study of two chimpanzees which received a high inoculum of BRSV, there was evidence of replication in only one animal and, upon subsequent challenge with HRSV, the duration of shedding was slightly reduced but otherwise the titer of HRSV and the magnitude of clinical symptoms were undiminished. These studies indicate that isolates of BRSV found in nature are not suited for direct vaccine use.

The instant invention provides for development of live-attenuated RSV vaccine candidates based on chimeras between HRSV and BRSV. Chimeras are constructed through a cDNA intermediate and cDNA-based recovery system. Recombinant viruses which are made from cDNA replicate independently and are propagated in the same manner as if they were biologically-derived, and indeed can only be distinguished from biologically derived viruses by the presence of mutations which have been specifically inserted. Chimeric HRSV/BRSV vaccine candidates preferably bear one or more of the major antigenic determinants of HRSV in a background which is attenuated by the presence of one or more BRSV genes. In addition, human-bovine chimeric RSV according to the invention can be further modified to incorporate specific attenuating mutations, as well as a variety of other mutations and nucleotide modifications, to yield desired structural or phenotypic affects.

Detailed descriptions of the materials and methods for producing recombinant RSV from cDNA, and for making and testing the full range of mutations and nucleotide modifications disclosed herein as supplemental aspects of the present invention, are set forth in, e.g., U.S. Provisional Patent Application No. 60/007,083, filed Sep. 27, 1995; U.S. patent application Ser. No. 08/720,132, filed Sep. 27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. Pat. No. 5,993,824, issued Nov. 30, 1999 (corresponding to International Publication No. WO 98/02530); U.S. patent application Ser. No. 09/291,894, filed by Collins et al. on Apr. 13, 1999; U.S. Provisional Patent Application No. 60/129,006, filed by Murphy et al. on Apr. 13, 1999; Crowe et al., *Vaccine* 12: 691-699, 1994; and Crowe et al., *Vaccine* 12: 783-790, 1994; Collins, et al., *Proc Nat. Acad. Sci. USA* 92:11563-11567, 1995; Bukreyev, et al., *J Virol* 70:6634-41, 1996, Juhasz et al., *J. Virol.* 71(8):5814-5819, 1997; Durbin et al., *Virology* 235: 323-332, 1997; Karron et al., *J. Infect. Dis.* 176:1428-1436, 1997); He et al. *Virology* 237:249-260, 1997; Baron et al. *J. Virol.* 71:1265-1271, 1997; Whitehead et al., *Virology* 247(2): 232-9, 1998a; Whitehead et al., *J. Virol.* 72(5):4467-4471, 1998b; Jin et al. *Virology* 251:206-214, 1998; Bukreyev, et al., *Proc. Nat. Acad. Sci. USA* 96:2367-2372, 1999; Bermingham and Collins, *Proc. Natl. Acad. Sci. USA* 96:11259-11264, 1999 Juhasz et al., *Vaccine* 17:1416-1424, 1999; Juhasz et al., *J. Virol.* 73:5176-5180, 1999; Teng and Collins, *J. Virol.* 73:466-473, 1999; Whitehead et al., *J. Virol.* 73:9773-9780, 1999; Whitehead et al., *J. Virol.* 73:871-877, 1999; and Whitehead et al., *J. Virol.* 73:3438-3442, 1999. Exemplary methods for producing recombinant RSV from cDNA involve intracellular coexpression, typically from plasmids cotransfected into tissue culture cells, of an RSV antigenomic RNA and the RSV N, P, M2-1 and L proteins. This launches a productive infection that results in the production of infectious cDNA-derived virus, which is termed recombinant virus. Once generated, recombinant RSV is readily propagated in the same manner as biologically-derived virus, and a recombinant virus and a counterpart biologically-derived virus cannot be distinguished unless the former had been modified to contain one or more introduced changes as markers.

In more detailed aspects, the foregoing incorporated documents describe methods and procedures useful within the invention for mutagenizing, isolating and characterizing RSV to obtain attenuated mutant strains (e.g., temperature sensitive (ts), cold passaged (cp) cold-adapted (ca), small plaque (sp) and host-range restricted (hr) mutant strains) and for identifying the genetic changes that specify the attenuated phenotype. In conjunction with these methods, the foregoing documents detail procedures for determining replication, immunogenicity, genetic stability and protective efficacy of biologically derived and recombinantly produced attenuated human RSV, including human RSV A and B subgroups, in accepted model systems, including murine and non-human primate model systems. In addition, these documents describe general methods for developing and testing immunogenic compositions, including monovalent and bivalent vaccines, for prophylaxis and treatment of RSV infection.

The ability to generate infectious RSV from cDNA provides a method for introducing predetermined changes into infectious virus via the cDNA intermediate. This method has been demonstrated to produce a wide range of infectious, attenuated derivatives of RSV, for example recombinant vaccine candidates containing one or more amino acid substitutions in a viral protein, deletion of one or more genes or ablation of gene expression, and/or one or more nucleotide substitutions in cis-acting RNA signals yielding desired effects on viral phenotype (see, e.g., Bukreyev et al., *J. Virol.* 71:8973-8982, 1997; Whitehead et al., *J. Virol.* 72:4467-4471, 1998; Whitehead et al., *Virology* 247:232-239, 1998; Bermingham and Collins, *Proc. Natl. Acad. Sci. USA* 96:11259-11264, 1999; Juhasz et al., *Vaccine* 17:1416-1424, 1999; Juhasz et al., *J. Virol.* 73:5176-5180, 1999; Teng and Collins, *J. Virol.* 73:466-473, 1999; Whitehead et al., *J. Virol.* 73:871-877, 1999; Whitehead et al., *J. Virol.* 73:3438-3442, 1999; and Collins et al., *Adv. Virus Res.* 54:423-451, 1999, each incorporated herein by reference).

Exemplary of the foregoing teachings are methods for constructing and evaluating infectious recombinant RSV modified to incorporate phenotype-specific mutations identified in biologically-derived RSV mutants, e.g., cp and ts mutations adopted in recombinant RSV from biologically derived designated cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579). These methods are readily adapted for construction of recombinant human-bovine chimeric RSV of the invention. The recombinant RSV thus provided may incorporate two or more ts mutations from the same, or different, biologically derived RSV mutant(s), for example one or more of the 248/404, 248/955, 530/1009, or 530/1030 biological mutants. In the latter context, multiply attenuated recombinants may have a combination of attenuating mutations from two, three or more biological mutants, e.g., a combination of attenuating mutations from the RSV mutants 530/1009/404, 248/404/1009, 248/404/1030, or 248/404/1009/1030 mutants. In exemplary embodiments, one or more attenuating mutations specify a temperature-sensitive substitution at amino acid Asn43, Phe521, Gln831, Met1169, or Tyr1321 in the RSV polymerase gene or a temperature-sensitive nucleotide substitution in the gene-start sequence of gene M2. Preferably, these mutations involve identical or conservative changes with the following changes identified in biologically derived mutant RSV, for example changes conservative to the following substitutions identified in the L polymerase gene: Ile for Asn43, Leu for Phe521, Leu for Gln831, Val for Met1169, and Asn for Tyr1321.

Yet additional mutations that may be incorporated in human-bovine chimeric RSV of the invention are mutations, e.g., attenuating mutations, identified in heterologous RSV or more distantly related negative stranded RNA viruses. In particular, attenuating and other desired mutations identified in one negative stranded RNA virus may be "transferred", e.g., copied, to a corresponding position within a human or bovine RSV genome or antigenome, either within the human-bovine chimeric RSV or as a means of constructing the human-bovine chimeric RSV. Briefly, desired mutations in one heterologous negative stranded RNA virus are transferred to the RSV recipient (e.g., bovine or human RSV, respectively). This involves mapping the mutation in the heterologous virus, thus identifying by sequence alignment the corresponding site in human or bovine RSV, and mutating the native sequence in the RSV recipient to the mutant genotype (either by an identical or conservative mutation), as described in U.S. Provisional Patent Application No. 60/129,006, filed by Murphy et al. on Apr. 13, 1999, incorporated herein by reference. As this disclosure teaches, it is preferable to modify the chimeric genome or antigenome to encode an alteration at the subject site of mutation that corresponds conservatively to the alteration identified in the heterologous mutant virus. For example, if an amino acid substitution marks a site of mutation in the mutant virus compared to the corresponding wild-type sequence, then a similar substitution should be engineered at the corresponding residue(s) in the recombinant virus. Preferably the substitution will involve an identical or conservative amino acid to the substitute residue present in the mutant viral protein. However, it is also possible to alter the native amino acid residue at the site of mutation non-conservatively with respect to the substitute residue in the mutant protein (e.g., by using any other amino acid to disrupt or impair the function of the wild-type residue). Negative stranded RNA viruses from which exemplary mutations are identified and transferred into a human-bovine chimeric RSV of the invention include other RSVs (e.g., murine), PIV, Sendai virus (SeV), Newcastle disease virus (NDV), simian virus 5 (SV5), measles virus (MeV), rindepest virus, canine distemper virus (CDV), rabies virus (RaV) and vesicular stomatitis virus (VSV). A variety of exemplary mutations are disclosed, including but not limited to an amino acid substitution of phenylalanine at position 521 of the RSV L protein (corresponding to a substitution of phenylalanine at position 456 of the HPIV3 L protein). In the case of mutations marked by deletions or insertions, these can be introduced as corresponding deletions or insertions into the recombinant virus, however the particular size and amino acid sequence of the deleted or inserted protein fragment can vary.

A variety of additional types of mutations are also disclosed in the foregoing incorporated references and can be readily engineered into a recombinant human-bovine chimeric RSV of the invention to calibrate attenuation, immunogenicity or provide other advantageous structural and/or phenotypic effects. For example, restriction site markers are routinely introduced within the human-bovine chimeric genome or antigenome to facilitate cDNA construction and manipulation. Also described in the incorporated references are a wide range of nucleotide modifications other than point or site-specific mutations that are useful within the instant invention. For example, methods and compositions are disclosed for producing recombinant RSV expressing an additional foreign gene, e.g., a chloramphenicol acetyl transferase (CAT) or luciferase gene. Such recombinants generally exhibit reduced growth associated with the inserted gene. This attenuation appears to increase with increasing length of the inserted gene. The finding that insertion of a foreign gene into recombinant RSV reduces level of replication and is stable during passage in vitro provides another effective method for attenuating RSV for vaccine use. Similar or improved effects can thus be achieved by insertion of other desired genes, for example cytokines such as interferon-γ, interleukin-2, interleukin-4 and GM-CSF, among others.

Additional nucleotide modifications disclosed in the foregoing references for incorporation into recombinant human-bovine chimeric RSV of the invention include partial or complete deletion or ablation of a selected RSV gene. Thus, RSV genes or genome segments may be deleted, including partial or complete deletions of open reading frames and/or cis-acting regulatory sequences of the RSV NS1, NS2, N, P, M, G, F, SH, M2(ORF1), M2(ORF2) and/or L genes. In one example, a recombinant RSV was generated in which expression of the SH gene was been ablated by removal of a polynucleotide sequence encoding the SH mRNA and protein. Deletion of the SH gene yielded not only recoverable, infectious RSV, but one which exhibited substantially improved growth in tissue culture based on both yield of infectious virus and plaque size. This improved growth in tissue culture specified by the SH deletion provides useful tools for developing human-bovine chimeric RSV vaccines, for example by overcoming problems of poor RSV yields in culture. Moreover, these deletions are highly stable against genetic reversion, rendering RSV clones derived therefrom particularly useful as vaccine agents.

SH-minus RSV recombinants also exhibit site-specific attenuation in the upper respiratory tract of mice, which presents novel advantages for vaccine development. Current RSV strains under evaluation as live virus vaccines, for example cp mutants, do not exhibit significantly altered growth in tissue culture. These are host range mutations and they restrict replication in the respiratory tract of chimpanzees and humans approximately 100-fold in the lower respiratory tract. Another exemplary type of mutation, ts mutations, tend to preferentially restrict virus replication in the lower respiratory tract due to the gradient of increasing body temperature from the upper to the lower respiratory tract. In contrast to these cp and ts mutants, SH-minus RSV mutants have distinct phenotypes of greater restriction in the upper respiratory tract. This is particularly desirable for vaccine viruses for use in very young infants, because restriction of replication in the upper respiratory tract is required to ensure safe vaccine administration in this vulnerable age group whose members breathe predominantly through the nose. Further, in any age group, reduced replication in the upper respiratory tract will reduce morbidity from otitis media. In addition to these advantages, the nature of SH deletion mutations, involving e.g., nearly 400 nt and ablation of an entire mRNA, represents a type of mutation which will be highly refractory to reversion.

Also discussed in the context of SH gene modifications is a comparison of SH genes among different RSVs, including human and bovine RSVs, and other pneumoviruses to provide additional tools and methods for generating useful RSV recombinant vaccines. For example, the two RSV antigenic subgroups, A and B, exhibit a relatively high degree of conservation in certain SH domains. In two such domains, the N-terminal region and putative membrane-spanning domains of RSV A and B display 84% identity at the amino acid level, while the C-terminal putative ectodomains are more divergent (approx. 50% identity). Comparison of the SH genes of two human RSV subgroup B strains, 8/60 and 18537, identified only a single amino acid difference (Anderson et al., supra). The SH proteins of human versus bovine RSV are approximately 40% identical, and share major structural features including (i) an asymmetric distribution of conserved residues; (ii) very similar hydrophobicity profiles; (iii) the presence of two N-linked glycosylation sites with one site being on each side of the hydrophobic region; and (iv) a single cysteine residue on the carboxyterminal side of the central hydrophobic region of each SH protein. (Anderson et al., supra). By evaluating these and other sequence similarities and differences, selections can be made of heterologous sequence(s) that can be substituted or inserted within infectious human-bovine chimeric RSV clones, for example to yield vaccines having multi-specific immunogenic effects or, alternatively or in addition, desirable effects such as attenuation.

Also disclosed in the context of gene deletions are the effects of changing gene position. For example, deletion of the SH gene results in an effective change in downstream gene position to a more promoter proximal position. This may be associated with an increase in transcription of downstream genes in the recombinant virus. Thus, methods are provided for altering levels of RSV gene expression by changing gene order or position in the genome or antigenome. Decreased levels of expression of downstream genes are expected to specify attenuation phenotypes, whereas increased expression can achieve the opposite effects in recombinant RSV in permissive hosts, e.g., chimpanzees and humans.

In another example described in the above-incorporated references, expression of the NS2 gene is ablated by introduction of stop codons into the translational open reading frame (ORF). The rate of release of infectious virus was reduced for this NS2 knock-out virus compared to wild-type. In addition, comparison of the plaques of the mutant and wild-type viruses showed that those of the NS2 knock-out were greatly reduced in size. This type of mutation can thus be incorporated within viable recombinant human-bovine chimeric RSV to yield altered phenotypes, in this case reduced rate of virus growth and reduced plaque size in vitro. These and other knock-out methods and mutants will therefore provide for yet additional recombinant RSV vaccine agents, based on the known correlation between reduced plaque size in vitro and attenuation in vivo. Expression of the NS2 gene also was ablated by complete removal of the NS2 gene, yielding a virus with a similar phenotype.

Other RSV genes which have been successfully deleted include the NS1 and M2-2 genes. The former was deleted by removal of the polynucleotide sequence encoding the respective protein, and the latter by introducing a frame-shift or altering translational start sites and introducing stop codons. Interestingly, recovered NS1-minus virus produce small plaques in tissue culture albeit not as small as those of the NS2 deletion virus. The fact that the NS1-minus virus can grow, albeit with reduced efficiency, identifies the NS1 protein as an accessory protein, one that is dispensable to virus growth. The plaque size of the NS1-minus virus was similar to that of NS2 knock-out virus in which expression of the NS2 protein was ablated by introducing translational stop codons into its coding sequence The small plaque phenotype is commonly associated with attenuating mutations. This type of mutation can thus be incorporated within viable recombinant RSV to yield altered phenotypes. These and other knock-out methods and mutants will therefore provide for yet additional recombinant human-bovine chimeric RSV vaccine agents, based on the known correlation between plaque size in vitro and attenuation in vivo. The NS2 knock-out mutant exhibited a moderately attenuated phenotype in the upper respiratory tract and a highly attenuated phenotype in the lower respiratory tract in naive chimpanzees. This mutant also elicited greatly reduced disease symptoms in chimps while stimulating significant resistance to challenge by the wild-type virus (Whitehead et al., J. Virol. 73:3438-3442, 1999, incorporated herein by reference).

Yet additional methods and compositions provided within the incorporated references and useful within the invention involve different nucleotide modifications within human-bovine chimeric RSV that alter cis-acting regulatory sequences within the chimeric genome or antigenome. For example, a translational start site for a secreted form of the RSV G glycoprotein can be deleted to disrupt expression of this form of the G glycoprotein. The RSV G protein is synthesized in two forms: as an anchored type II integral membrane protein and as a N-terminally resected form which lacks essentially all of the membrane anchor and is secreted (Hendricks et al., J. Virol. 62:2228-2233, 1988). The two forms have been shown to be derived by translational initiation at two different start sites: the longer form initiates at the first AUG of the G ORF, and the second initiates at the second AUG of the ORF at codon 48 and is further processed by proteolysis (Roberts et al., J. Virol. 68: 4538-4546 1994). The presence of this second start site is highly conserved, being present in all strains of human, bovine and ovine RSV sequenced to date. It has been suggested that the soluble form of the G protein might mitigate host immunity by acting as a decoy to trap neutralizing antibodies. Also, soluble G has been implicated in preferential stimulation of a Th2-biased response, which in turn appears to be associated with enhanced immunopathology upon subsequent exposure to RSV. With regard to an RSV vaccine virus, it is highly desirable to minimize antibody trapping or imbalanced stimulation of the immune system, and so it would be desirable to ablate expression of the secreted form of the G protein. This has been achieved in recombinant virus. Thus, this mutation is particularly useful to qualitatively and/or quantitatively alter the host immune response elicited by the recombinant virus, rather than to directly attenuate the virus.

The incorporated references also describe modulation of the phenotype of recombinant RSV by altering cis-acting transcription signals of exemplary genes, e.g., NS1 and NS2. The results of these nucleotide modifications are consistent with modification of gene expression by altering cis-regulatory elements, for example to decrease levels of readthrough mRNAs and increase expression of proteins from downstream genes. The resulting recombinant viruses will preferably exhibit increased growth kinetics and increased plaque size. Exemplary modifications to cis-acting regulatory sequences include modifications to gene end (GE) and gene start (GS) signals associated with RSV genes. In this context, exemplary changes include alterations of the GE signals of the NS1 and NS2 genes rendering these signals identical to the naturally-occurring GE signal of the RSV N gene. The resulting recombinant virus exhibits increased growth kinetics and plaque size and therefore provide yet additional means for beneficially modifying phenotypes of human-bovine chimeric RSV vaccine candidates.

Chimeric bovine-human RSV formed of a partial or complete BRSV background genome or antigenome and a heterologous gene or genome segment from HRSV may incorporate a heterologous gene or genome segment from a subgroup A or subgroup B HRSV, from both subgroup A and B HRSV, or from one or more specific HRSV strains. Exemplary HRSV strains in this context include the well known strains RSV A2 and Long. In preferred aspects, one or more HRSV glycoprotein genes F, G and SH, or a genome segment encoding a cytoplasmic domain, transmembrane domain, ectodomain or immunogenic epitope of a HRSV glycoprotein gene is substituted for a counterpart gene or genome segment within the BRSV background genome or antigenome. In alternate embodiments one or both of the HRSV glycoprotein genes F and G is/are substituted to replace one or both counterpart F and G glycoprotein genes in the BRSV background genome or antigenome. In one specific example described herein below, the F gene from HRSV Long is substituted into the rBRSV strain ATue51908 in place of the counterpart BRSV F gene. In another example, both HRSV glycoprotein genes F and G of the HRSV strain A2 are substituted to replace counterpart F and G glycoprotein genes in the BRSV ATue51908 strain background genome or antigenome. In alternative embodiments, chimeric human-bovine RSV of the invention incorporate antigenic determinants from more than one RSV strain or subgroup, e.g., both human RSV subgroup A and subgroup B.

Thus, methods and compositions provided in the above-incorporated references that allow production of attenuated human-bovine chimeric RSV vaccine viruses comprising sequences from both RSV subgroups A and B, e.g., to yield a RSV A or B vaccine or a bivalent RSV A/B vaccine (see, e.g., U.S. patent application Ser. No. 09/291,894, filed by Collins et al. on Apr. 13, 1999, incorporated herein by reference). In this context, a human-bovine chimeric RSV may comprise a BRSV into which multiple HRSV gene(s) or genome segment(s) are introduces encoding antigenic determinants from both HRSV A and HRSV B subgroups. This virus can then be attenuated to a desired level by systematic incorporation of attenuating mutations as described above. For example, specific attenuating mutations that have been incorporated into chimeric RSV A/B viruses include: (i) three of the five cp mutations, namely the mutation in N (V267I) and the two in L (C319Y and H1690Y), but not the two in F since these are removed by substitution with the B1 F gene; (ii) the 248 (Q831L), 1030 (Y1321N) and, optionally, 404-L (D1183E) mutations which have been identified in attenuated strain A2 viruses; (iii) the single nucleotide substitution at position 9 in the gene-start signal of the M2 gene, and (iv) deletion of the SH gene. Other immediately available mutations in human-bovine chimeric RSV carrying RSV A and or RSV B genes or genome segments include, but are not limited to, NS1, NS2, G, or M2-2 gene deletions, and the 530 and 1009 mutations, alone or in combination.

In other detailed aspects of the invention, human-bovine chimeric RSV are employed as "vectors" for protective antigens of heterologous pathogens, including other RSVs and non-RSV viruses and non-viral pathogens. Within these aspects, the bovine-human chimeric genome or antigenome comprises a partial or complete RSV "vector genome or antigenome" combined with one or more heterologous genes or genome segments encoding one or more antigenic determinants of one or more heterologous pathogens (see, e.g., U.S. Provisional Patent Application Ser. No. 60/170,195; U.S. patent application Ser. No. 09/458,813; and U.S. patent application Ser. No. 09/459,062, each incorporated herein by reference). The heterologous pathogen in this context may be a heterologous RSV (e.g., a different RSV strain or subgroup) and the heterologous gene(s) or genome segment(s) can be selected to encode one or more of the above identified RSV proteins, as well as protein domains, fragments, and immunogenic regions or epitopes thereof. RSV vector vaccines thus constructed may elicit a polyspecific immune response and may be administered simultaneously or in a coordinate administration protocol with other vaccine agents.

Human-bovine chimeric RSV engineered as vectors for other pathogens may comprise a vector genome or antigenome that is a partial or complete HRSV genome or antigenome, which is combined with or is modified to incorporate one or more heterologous genes or genome segments encoding antigenic determinant(s) of one or more heterologous RSV(s), including heterologous HRSVs selected from HRSV A or HRSV B. In alternative aspects, the vector genome or antigenome is a partial or complete HRSV genome or antigenome and the heterologous gene(s) or genome segment(s) encoding the antigenic determinant(s) is/are of one or more non-RSV pathogens. Typically, the chimeric genome or antigenome incorporates one or more gene(s) or genome segment(s) of a BRSV that specifies attenuation. Alternatively, the vector virus may be comprise a partial or complete BRSV background genome or antigenome incorporating one or more HRSV genes or genome segments, wherein the human-bovine chimeric RSV vector virus is modified to include one or more donor gene(s) or genome segment(s) encoding an antigenic determinant of a non-RSV pathogen.

Thus, in certain detailed aspects of the invention, human-bovine chimeric RSV are provided as vectors for a range of non-RSV pathogens (see, e.g., U.S. Provisional Patent Application Ser. No. 60/170,195; U.S. patent application Ser. No. 09/458,813; and U.S. patent application Ser. No. 09/459,062, each incorporated herein by reference). The vector genome or antigenome for use within these aspects of the invention may comprise a partial or complete BRSV or HRSV genome or antigenome incorporating, respectively, a heterologous HRSV or BRSV gene or genome segment, and the heterologous pathogen may be selected from measles virus, subgroup A and subgroup B respiratory syncytial viruses, HPIV1, HPIV2, HPIV3, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses.

For example, a HRSV or BRSV vector genome or antigenome for constructing bovine-human chimeric RSV of the invention may incorporate heterologous antigenic determinant(s) selected from the measles virus HA and F proteins, or antigenic domains, fragments and epitopes thereof. In exemplary embodiments, a transcription unit comprising an open reading frame (ORF) of a measles virus HA gene is added to or incorporated within a BRSV or HRSV3 vector genome or antigenome. Alternatively bovine-human chimeric RSV of the invention may used as vectors to incorporate heterologous antigenic determinant(s) from a parainfluenza virus (PIV), for example by incorporating one or more genes or genome segments that encode(s) a HPIV1, HPIV2, or HPIV3 HN or F glycoprotein or immunogenic domain(s) or epitope(s) thereof.

As noted above, exemplary embodiments of the invention feature replacement or addition of a heterologous gene(s), genome segment(s), or single or multiple nucleotides of a human or bovine RSV, which are added to or substituted within a partial or complete background bovine or human RSV genome or antigenome to produce the human-bovine chimeric RSV genome or antigenome. In one aspect of the invention, human-bovine chimeric RSV incorporate a partial or complete bovine background RSV genome or antigenome combined with one or more heterologous gene or genome segment from one or more human RSV subgroup(s) or strain(s). Alternatively, human-bovine chimeric RSV may incorporate a partial or complete human background RSV genome or antigenome combined with a heterologous gene or genome segment from one or more bovine RSV. Genes and genome segments that are selected for use as heterologous inserts or additions to the background genome or antigenome include any wild-type or mutant genes or genome segments encoding an RSV NS1, NS2, N, P, M, SH, M2(ORF1), M2(ORF2), L, F or G proteins, or a portion thereof or any additional genome segments. Preferably, the heterologous human gene(s) encode(s) an RSV F, G or SH glycoprotein to provide desired immunogenic effects. In one exemplary embodiment, one or more human RSV glycoprotein genes F, SH, and/or G are added to or substituted within a partial or complete bovine genome or antigenome to yield an attenuated, infectious human-bovine chimera that elicits an anti-human RSV immune response in a susceptible host. Alternatively, the human-bovine chimeric RSV may incorporate one or more genome segment(s) encoding a cytoplasmic domain, transmembrane domain, ectodomain or immunogenic epitope of a human RSV F, G or SH glycoprotein. These immunogenic proteins, domains and epitopes also generate novel immune responses in an immunized host. For example, addition or substitution of one or more immunogenic gene(s) or genome segment(s) from a human RSV subgroup or strain to or within a bovine background genome or antigenome yields a recombinant, chimeric virus or subviral particle capable of generating an immune response directed against one or more specific human RSV "donor" subgroups or strains, while the bovine backbone confers an attenuated phenotype making the chimera a useful candidate for vaccine development. Thus, heterologous donor genes or genome segments from one RSV strain or subgroup are combined with or substituted within a recipient RSV genome or antigenome that serves as a background for the donor gene or genome segment. The recipient genome or antigenome may act as a "vector" to import and express heterologous genes or genome segments encoding one or more antigenic determinants of a different virus to yield chimeric RSV exhibiting novel structural and/or phenotypic, particularly immunogenic, characteristics. Alternatively, addition or substitution of the heterologous gene or genome segment within a selected background RSV yields attenuation, growth changes, or other desired phenotypic changes, as compared with corresponding phenotypes of the unmodified recipient and/or donor.

The introduction of heterologous immunogenic proteins, domains and epitopes to produce chimeric RSV is particularly useful to generate novel immune responses in an immunized host. Addition or substitution of an immunogenic gene or genome segment from one, donor RSV subgroup or strain within a recipient genome or antigenome of a different RSV subgroup or strain can generate an immune response directed against the donor subgroup or strain, the recipient subgroup or strain, or against both the donor and recipient subgroup or strain. To achieve this purpose, human-bovine chimeric RSV may also be constructed that express a chimeric protein, e.g., an immunogenic glycoprotein having a cytoplasmic tail and/or transmembrane domain specific to one RSV fused to an ectodomain of a different RSV to provide, e.g., a human-bovine fusion protein, or a fusion protein incorporating domains from two different human RSV subgroups or strains. In a preferred embodiment, a human-bovine chimeric RSV genome or antigenome encodes a chimeric glycoprotein in the recombinant virus or subviral particle having both human and bovine glycoprotein domains or immunogenic epitopes. For example, a heterologous genome segment encoding a glycoprotein ectodomain from a human RSV F, SH or G glycoprotein may be joined with a polynucleotide sequence (i.e., a genome segment) encoding the corresponding bovine F, SH or G glycoprotein cytoplasmic and endo domains to form the human-bovine chimeric RSV genome or antigenome.

In other embodiments, human-bovine chimeric RSV useful in a vaccine formulation can be conveniently modified to accommodate antigenic drift in circulating virus. Typically the modification will be in the G and/or F proteins. An entire G or F gene, or a genome segment encoding a particular immunogenic region thereof, from one RSV strain is incorporated into a chimeric RSV genome or antigenome cDNA by replacement of a corresponding region in a recipient clone of a different RSV strain or subgroup, or by adding one or more copies of the gene, such that several antigenic forms are represented. Progeny virus produced from the modified RSV clone can then be used in vaccination protocols against emerging RSV strains.

A variety of additional embodiments of the invention involve the addition or substitution of only a portion of a donor gene of interest to the recipient genome or antigenome. Commonly, non-coding nucleotides such as cis-acting regulatory elements and intergenic sequences need not be transferred with the donor gene coding region. Thus, a coding sequence (e.g., a partial or complete open reading frame (ORF)) of a particular gene may be added or substituted to the partial or complete background genome or antigenome under control of a heterologous promoter (e.g., a promoter existing in the background genome or antigenome) of a counterpart gene or different gene as compared to the donor sequence. A variety of additional genome segments provide useful donor polynucleotides for inclusion within a chimeric genome or antigenome to express chimeric RSV having novel and useful properties. For example, heterologous genome segments may encode part or all of a glycoprotein cytoplasmic tail region, transmembrane domain or ectodomain, an epitopic site or region, a binding site or region containing a binding site, an active site or region containing an active site, etc., of a selected protein from a human or bovine RSV. These and other genome segments can be added to a complete background genome or antigenome or substituted therein for a counterpart genome segment to yield novel chimeric RSV recombinants. Certain recombinants will express a chimeric protein, e.g., a protein having a cytoplasmic tail and/or transmembrane domain of one RSV fused to an ectodomain of another RSV.

According to one aspect of the invention, human-bovine chimeric RSV are constructed by substituting the heterologous gene or genome segment for a counterpart gene or genome segment in a partial RSV background genome or antigenome. Alternatively, the heterologous gene or genome segment may be added as a supernumerary gene or genome segment in combination with a complete (or partial if another gene or genome segment is deleted) RSV background genome or antigenome. The heterologous gene or genome segment may be added at an intergenic position within a partial or complete RSV background genome or antigenome so as not to disrupt an open reading frame within the background genome or antigenome.

The heterologous gene or genome segment may be added or substituted at a position corresponding to a wild-type gene order position of a counterpart gene or genome segment within the partial or complete RSV background genome or antigenome, which counterpart gene or genome segment is thereby replaced or displaced (e.g., to a more promoter-distal position). In yet additional embodiments, the heterologous gene or genome segment is added or substituted at a position that is more promoter-proximal or promoter-distal compared to a wild-type gene order position of the counterpart gene or genome segment within the background genome or antigenome, which enhances or reduces, respectively, expression of the heterologous gene or genome segment.

With regard to gene order, a number of the foregoing incorporated references have focused on modification of the naturally-occurring order in RSV and other viruses. For example, in RSV the NS1, NS2, SH and G genes were deleted individually, and the NS1 and NS2 gene were deleted together, thereby shifting the position of each downstream gene relative to the viral promoter. For example, when NS1 and NS2 are deleted together, N is moved from position 3 to position 1, P from position 4 to position 2, and so on. Alternatively, deletion of any other gene within the gene order will affect the position (relative to the promoter) only of those genes which are located further downstream. For example, SH occupies position 6 in wild type virus, and its deletion does not affect M at position 5 (or any other upstream gene) but moves G from position 7 to 6 relative to the promoter. It should be noted that gene deletion also can occur (rarely) in a biologically-derived mutant virus. For example, a subgroup B RSV that had been passaged extensively in cell culture spontaneously deleted the SH and G genes (Karron et al., *Proc. Natl. Acad. Sci. USA* 94:13961-13966, 1997; incorporated herein by reference). Note that "upstream" and "downstream" refer to the promoter-proximal and promoter-distal directions, respectively (the promoter is at the 3' leader end of negative-sense genomic RNA).

Gene order shifting modifications (i.e., positional modifications moving one or more genes to a more promoter-proximal or promoter-distal location in the recombinant viral genome) with human-bovine chimeric RSV of the invention result in viruses with altered biological properties. For example, RSV lacking NS1, NS2, SH, G, NS1 and NS2 together, or SH and G together, have been show to be attenuated in vitro, in vivo, or both. It is likely that this phenotype was due primarily to the loss of expression of the specific viral protein. However, the altered gene map also likely contributed to the observed phenotype. This effect is well-illustrated by the SH-deletion virus, which grew more efficiently than wild type in some cell types, probably due to an increase in the efficiency of transcription, replication or both resulting from the gene deletion and resulting change in gene order and possibly genome size. In other viruses, such as RSV in which NS1 and/or NS2 were deleted, altered growth that might have occurred due to the change in gene order likely was obscured by the more dominant phenotype due to the loss of expression of the RSV protein(s).

Yet additional changes have been introduced to change the gene order of RSV in an effort to improve its properties as a live-attenuated vaccine. (see, U.S. Provisional Patent Application entitled RESPIRATORY SYNCYTIAL VIRUS VACCINES EXPRESSING PROTECTIVE ANTIGENS FROM PROMOTOR-PROXIMAL GENES, filed by Krempl et al., Jun. 23, 2000 and identified by Ser. No. 60/213,708, incorporated herein by reference). In particular, the G and F genes were shifted, singly and in tandem, to a more promoter-proximal position relative to their wild-type gene order. These two proteins normally occupy positions 7 (G) and 8 (F) in the RSV gene order (NS1-NS2-N-P-M-SH-G-F-M2-L). In order to increase the possibility of successful recovery, the manipulations were performed in a version of RSV in which the SH gene had been deleted (Whitehead et al., *J. Virol.* 73:3438-42 (1999), incorporated herein by reference). This facilitates recovery because this virus makes larger plaques in vitro (Bukreyev et al., *J. Virol.*, 71:8973-82 (1997), incorporated herein by reference). G and F were then moved individually to position 1, or were moved together to positions 1 and 2, respectively.

Surprisingly, recombinant RSV were readily recovered in which G or F were moved to position 1, or in which G and F were moved to positions 1 and 2, respectively. This result differed greatly from previous studies with VSV, where movement of the single VSV glycoprotein gene by only two positions was very deleterious to virus growth. The ability to recover these altered viruses also was surprising because RSV replicates inefficiently and because RSV has a complex gene order and movement of the glycoprotein genes involved a large number of position changes. Indeed, the rearranged RSV's grew at least as well as their immediate parent having the wild type order of genes. As indicated above, this is particularly important for RSV, since the wild type virus grows inefficiently in cell culture and a further reduction in replication in vitro would likely render vaccine preparation unfeasible. Thus, it is remarkable that all of the NS1-NS2-N-P-M proteins could be displaced by one or two positions relative to the promoter without a significant decrease in growth fitness. In addition, examination of the expression of the G glycoprotein showed that it was increased up to several-fold over that of its parent virus. This indicated that a vaccine virus containing G and/or F in the first position expresses a higher molar amount of these protective antigens compared to the other viral proteins, and thus represent a virus with desired vaccine properties.

Similarly extensive modifications in gene order also were achieved with two highly attenuated vaccine candidates in which the NS2 gene was deleted on its own, or in which the NS1 and NS2 genes were deleted together. In these two vaccine candidates, the G and F glycoproteins were moved together to positions 1 and 2 respectively, and the G, F and SH glycoproteins were deleted from their original downstream position. Thus, the recovered viruses G1F2ΔNS2ΔSH and G1F2/ΔNS1ΔNS2ΔSH had two and three genes deleted respectively in addition to the shift of the G and F genes. To illustrate the extent of the changes involved, the gene orders of wild type RSV (NS1-NS2-N-P-M-SH-G-F-M2-L) and the G1F2/ΔNS2ΔSH virus (G-F-NS1-N-P-M-M2-L) or the ΔNS1ΔNS2ΔSH (G-F-N-P-M-M2-L) can be compared. This shows that the positions of most or all of the genes relative to the promoter were changed. Nonetheless, these highly attenuated derivatives retained the capacity to be grown in cell culture.

The examples below provide an exemplary construct of an infectious recombinant human-bovine chimeric RSV (rBRSV/HRSV) in which the HRSV G and F genes are substituted into a recombinant bovine RSV (rBRSV) background. The resulting human-bovine chimera contains two genes of HRSV, namely G and F, and eight genes from BRSV, namely NS1, NS2, N, P, M, SH, M2 and L.

In addition to this basic substituted glycoprotein construction, the HRSV G and F genes are shifted to a more promoter-proximal position in the rBRSV backbone, i.e., relative to the wild-type gene order position of the F and G genes in the RSV genome. More specifically, the F and G genes were moved from their usual location relative to the promoter, namely gene positions 7 and 8, respectively, to positions 1 and 2, respectively.

The resulting chimeric recombinant virus, rBRSV/A2-G1F2, was very similar in its levels of F and G protein expression as detected by immunofluorescence to that of wt HRSV, which result is consistent with increased expression of the G and F glycoproteins attributed to the promoter-proximal shift of the genes. Since the present rBRSV/A2-G1F2 virus bears the same constellation of BRSV genes in its genetic background, it is likely to share this strong host range restriction phenotype. In this context, the increased expression of the two protective antigens in vivo will increase the immunogenicity of this virus to produce highly desirable vaccine properties.

To construct chimeric RSV, heterologous genes may be added or substituted in whole or in part to the background genome or antigenome. In the case of chimeras generated by substitution, a selected gene or genome segment encoding a protein or protein region (e.g., a cytoplasmic tail, transmembrane domain or ectodomain, an epitopic site or region, a binding site or region, an active site or region containing an active site, etc.) from a human or bovine RSV is substituted for a counterpart gene or genome segment in the background RSV genome or antigenome to yield novel recombinants having desired phenotypic changes compared to one or both of the respective wild-type (or mutant parent) RSV strains. As used herein, "counterpart" genes or genome segments refer to counterpart polynucleotides from different RSV sources that encode homologous or equivalent proteins or protein domains, epitopes, or amino acid residues, or which represent homologous or equivalent cis-acting signals which may include but are not limited to species and allelic variants among different RSV subgroups or strains.

The human and bovine strains have the same gene map and encode essentially the same constellation of mRNAs and proteins. For example, each has ORFs encoding NS1, NS2, N, P, M, SH, G, F, M2-1, M2-2 and L proteins. The percent amino acid identity between selected human and bovine proteins is: NS1 (69%), NS2 (84%), N (93%), P (81%), M (89%), SH (38%), G (30%), F (18%), M2-1 (80%), L (77%). In general, therefore, there is clearly discernable correspondence between the genes and genome segments of the two viruses, and the design of substitutions, transfers and insertions is straightforward.

Counterpart genes and genome segments for use within the human-bovine chimeric RSV of the invention embrace an assemblage of alternate polynucleotides having a range of size and sequence variation. Useful genome segments in this regard range from about 15-35 nucleotides in the case of genome segments encoding small functional domains of proteins, e.g., epitopic sites, to about 50, 75, 100, 200-500, and 500-1,500 or more nucleotides for genome segments encoding larger domains or protein regions. Selection of counterpart genes and genome segments relies on sequence identity or linear correspondence in the genome between the subject counterparts. In this context, a selected human or bovine polynucleotide "reference sequence" is defined as a sequence or portion thereof present in either the donor or recipient genome or antigenome. This reference sequence is used as a defined sequence to provide a rationale basis for sequence comparison with the counterpart heterologous sequence. For example, the reference sequence may be a defined a segment of a cDNA or gene, or a complete cDNA or gene sequence. Generally, a reference sequence for use in defining counterpart genes and genome segments is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of (Smith & Waterman, *Adv. Appl. Math.* 2:482, 1981), by the homology alignment algorithm of (Needleman & Wunsch, *J. Mol. Biol.* 48:443, 1970), by the search for similarity method of (Pearson & Lipman, *Proc. Natl. Acad. Sci. USA* 85:2444, 1988) (each of which is incorporated by reference), by computerized implementations of these algorithms (GAP, BESTFIT, FASTA, and TFASTA in the Wisconsin Genetics Software Package Release 7.0, Genetics Computer Group, 575 Science Dr., Madison, Wis., incorporated herein by reference), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

Corresponding residue positions between bovine and human RSV may be divergent, identical or may differ by conservative amino acid substitutions. Conservative amino acid substitutions refer to the interchangeability of residues having similar side chains. For example, a conservative group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other amino and imino acids (e.g., 4-hydroxyproline). Moreover, amino acids may be modified by glycosylation, phosphorylation and the like.

The present invention employs cDNA-based methods to construct a variety of recombinant, human-bovine chimeric RSV viruses and subviral particles. These recombinant RSV offer improved characteristics of attenuation and immunogenicity for use as vaccine agents. Desired phenotypic changes that are engineered into human-bovine chimeric RSV include, but are not limited to, attenuation in culture or in a selected host environment, resistance to reversion from the attenuated phenotype, enhanced immunogenic characteristics (e.g., as determined by enhancement, or diminution, of an elicited immune response), upregulation or downregulation of transcription and/or translation of selected viral products, etc. In preferred aspects of the invention, attenuated, human-bovine chimeric RSV are produced in which the chimeric genome or antigenome is further modified by introducing one or more attenuating mutations specifying an attenuating phenotype. These mutations may be generated de novo and tested for attenuating effects according to a rational design mutagenesis strategy as described in the above-incorporated references. Alternatively, the attenuating mutations can be identified in a biologically derived mutant RSV and thereafter incorporated into the human-bovine chimeric RSV of the invention.

Attenuating mutations in biologically derived RSV for incorporation within a human-bovine chimeric RSV vaccine strain may occur naturally or may be introduced into wild-type RSV strains by well known mutagenesis procedures. For example, incompletely attenuated parental RSV strains can be produced by chemical mutagenesis during virus growth in cell cultures to which a chemical mutagen has been added, by selection of virus that has been subjected to passage at suboptimal temperatures in order to introduce growth restriction mutations, or by selection of a mutagenized virus that produces small plaques (sp) in cell culture, as generally described herein and in U.S. Pat. No. 5,922,326, issued Jul. 13, 1999, incorporated herein by reference.

By "biologically derived RSV" is meant any RSV not produced by recombinant means. Thus, biologically derived RSV include naturally occurring RSV of all subgroups and strains, including, e.g., naturally occurring RSV having a wild-type genomic sequence and RSV having genomic variations from a reference wild-type RSV sequence, e.g., RSV having a mutation specifying an attenuated phenotype. Likewise, biologically derived RSV include RSV mutants derived from a parental RSV strain by, inter alia, artificial mutagenesis and selection procedures.

To produce a satisfactorily attenuated RSV from biologically derived strains, mutations are preferably introduced into a parental strain which has been incompletely or partially attenuated, such as the well known ts-1 or ts-1NG or cpRSV mutants of the A2 strain of RSV subgroup A, or derivatives or subclones thereof. Using these and other partially attenuated strains additional mutation(s) can be generated that further attenuate the strain, e.g., to a desired level of restricted replication in a mammalian host, while retaining sufficient immunogenicity to confer protection in vaccinees.

Partially attenuated mutants of the subgroup A or B virus can be produced by well known methods of biologically cloning wild-type virus in an acceptable cell substrate and developing, e.g., cold-passaged mutants thereof, subjecting the virus to chemical mutagenesis to produce ts mutants, or selecting small plaque or similar phenotypic mutants (see, e.g., Murphy et al., International Publication WO 93/21310, incorporated herein by reference). For virus of subgroup B, an exemplary, partially attenuated parental virus is cp 23, which is a mutant of the B1 strain of subgroup B.

Various known selection techniques may be combined to produce partially attenuated mutants from non-attenuated subgroup A or B strains which are useful for further derivatization as described herein. Further, mutations specifying attenuated phenotypes may be introduced individually or in combination in incompletely attenuated subgroup A or B virus to produce vaccine virus having multiple, defined attenuating mutations that confer a desired level of attenuation and immunogenicity in vaccinees.

As noted above, production of a sufficiently attenuated biologically derived RSV mutant can be accomplished by several known methods. One such procedure involves subjecting a partially attenuated virus to passage in cell culture at progressively lower, attenuating temperatures. For example, whereas wild-type virus is typically cultivated at about 34-37° C., the partially attenuated mutants are produced by passage in cell cultures (e.g., primary bovine kidney cells) at suboptimal temperatures, e.g., 20-26° C. Thus, the cp mutant or other partially attenuated strain, e.g., ts-1 or spRSV, is adapted to efficient growth at a lower temperature by passage in MRC-5 or Vero cells, down to a temperature of about 20-24° C., preferably 20-22° C. This selection of mutant RSV during cold-passage substantially reduces any residual virulence in the derivative strains as compared to the partially attenuated parent.

Alternatively, specific mutations can be introduced into biologically derived RSV by subjecting a partially attenuated parent virus to chemical mutagenesis, e.g., to introduce ts mutations or, in the case of viruses which are already ts, additional ts mutations sufficient to confer increased attenuation and/or stability of the ts phenotype of the attenuated derivative. Means for the introduction of ts mutations into RSV include replication of the virus in the presence of a mutagen such as 5-fluorouridine or 5-fluorouracil in a concentration of about $10^{-3}$ to $10^{-5}$ M, preferably about $10^{-4}$ M, exposure of virus to nitrosoguanidine at a concentration of about 100 μg/ml, according to the general procedure described in, e.g., (Gharpure et al., *J. Virol.* 3:414-421, 1969 and Richardson et al., *J. Med. Virol.* 3:91-100, 1978), or genetic introduction of specific ts mutations. Other chemical mutagens can also be used. Attenuation can result from a ts mutation in almost any RSV gene, although a particularly amenable target for this purpose has been found to be the polymerase (L) gene.

The level of temperature sensitivity of replication in exemplary attenuated RSV for use within the invention is determined by comparing its replication at a permissive temperature with that at several restrictive temperatures. The lowest temperature at which the replication of the virus is reduced 100-fold or more in comparison with its replication at the permissive temperature is termed the shutoff temperature. In experimental animals and humans, both the replication and virulence of RSV correlate with the mutant's shutoff temperature. Replication of mutants with a shutoff temperature of 39° C. is moderately restricted, whereas mutants with a shutoff of 38° C. replicate less well and symptoms of illness are mainly restricted to the upper respiratory tract. A virus with a shutoff temperature of 35° C. to 37° C. will typically be fully attenuated in chimpanzees and substantially attenuated in humans. Thus, attenuated biologically derived mutant and human-bovine chimeric RSV of the invention which are ts will have a shutoff temperature in the range of about 35° C. to 39° C., and preferably from 35° C. to 38° C. The addition of a ts mutation into a partially attenuated strain produces a multiply attenuated virus useful within vaccine compositions of the invention.

A number of attenuated RSV strains as candidate vaccines for intranasal administration have been developed using multiple rounds of chemical mutagenesis to introduce multiple mutations into a virus which had already been attenuated during cold-passage (e.g., Connors et al., *Virology* 208: 478-484, 1995; Crowe et al., *Vaccine* 12: 691-699, 1994; and Crowe et al., *Vaccine* 12: 783-790, 1994, incorporated herein by reference). Evaluation in rodents, chimpanzees, adults and infants indicate that certain of these candidate vaccine strains are relatively stable genetically, are highly immunogenic, and may be satisfactorily attenuated. Nucleotide sequence analysis of some of these attenuated viruses indicates that each level of increased attenuation is associated with specific nucleotide and amino acid substitutions. The above-incorporated references also disclose how to routinely distinguish between silent incidental mutations and those responsible for phenotype differences by introducing the mutations, separately and in various combinations, into the genome or antigenome of infectious RSV clones. This process coupled with evaluation of phenotype characteristics of parental and derivative virus mutations responsible for such desired characteristics as attenuation, temperature sensitivity, cold-adaptation, small plaque size, host range restriction, etc.

Mutations thus identified are compiled into a "menu" and are then introduced as desired, singly or in combination, to calibrate a human-bovine chimeric RSV vaccine virus to an appropriate level of attenuation, immunogenicity, genetic resistance to reversion from an attenuated phenotype, etc., as desired. Preferably, the chimeric RSV of the invention are attenuated by incorporation of at least one, and more preferably two or more, attenuating mutations identified from such a menu, which may be defined as a group of known mutations within a panel of biologically derived mutant RSV strains. Preferred panels of mutant RSV strains described herein are cold passaged (cp) and/or temperature sensitive (ts) mutants, for example a panel comprised of RSV mutants designated cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579) (each deposited under the terms of the Budapest Treaty with the American Type Culture Collection (ATCC) of 10801 University Boulevard, Manassas, Va. 20110-2209, U.S.A., and granted the above identified accession numbers).

From this exemplary panel of biologically derived mutants, a large menu of attenuating mutations are provided which can each be combined with any other mutation(s) within the panel for calibrating the level of attenuation in a recombinant, human-bovine chimeric RSV for vaccine use. Additional mutations may be derived from RSV having non-ts and non-cp attenuating mutations as identified, e.g., in small plaque (sp), cold-adapted (ca) or host-range restricted (hr) mutant strains. Attenuating mutations may be selected in coding portions of a donor or recipient RSV gene or in non-coding regions such as a cis-regulatory sequence. For example, attenuating mutations may include single or multiple base changes in a gene start sequence, as exemplified by a single or multiple base substitution in the M2 gene start sequence at nucleotide 7605.

Human-bovine chimeric RSV designed and selected for vaccine use often have at least two and sometimes three or more attenuating mutations to achieve a satisfactory level of attenuation for broad clinical use. In one embodiment, at least one attenuating mutation occurs in the RSV polymerase gene (either in the donor or recipient gene) and involves a nucleotide substitution specifying an amino acid change in the polymerase protein specifying a temperature-sensitive (ts) phenotype. Exemplary human-bovine chimeric RSV in this context incorporate one or more nucleotide substitutions in the large polymerase gene L resulting in an amino acid change at amino acid Asn43, Phe521, Gln831, Met1169, or Tyr1321, as exemplified by the changes, Leu for Phe521, Leu for Gln831, Val for Met1169, and Asn for Tyr1321. Alternately or additionally, chimeric RSV of the invention may incorporate a ts mutation in a different RSV gene, e.g., in the M2 gene. Preferably, two or more nucleotide changes are incorporated in a codon specifying an attenuating mutation, e.g., in a codon specifying a ts mutation, thereby decreasing the likelihood of reversion from an attenuated phenotype.

In accordance with the methods of the invention, human-bovine chimeric RSV can be readily constructed and characterized that incorporate at least one and up to a full complement of attenuating mutations present within a panel of biologically derived mutant RSV strains. Thus, mutations can be assembled in any combination from a selected panel of mutants, for example, cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579). In this manner, attenuation of chimeric vaccine candidates can be finely calibrated for use in one or more classes of patients, including seronegative infants.

In more specific embodiments, human-bovine chimeric RSV for vaccine use incorporate at least one and up to a full complement of attenuating mutations specifying a temperature-sensitive and/or attenuating amino acid substitution at Asn43, Phe521, Gln831, Met1169 or Tyr1321 in the RSV polymerase gene L, or a temperature-sensitive nucleotide substitution in the gene-start sequence of gene M2. Alternatively or additionally, chimeric RSV of claim may incorporate at least one and up to a full complement of mutations from cold-passaged attenuated RSV, for example one or more mutations specifying an amino acid substitution at Val267 in the RSV N gene, Glu218 or Thr523 in the RSV F gene, Cys319 or His1690 in the RSV polymerase gene L.

In other detailed embodiments, the human-bovine chimeric RSV of the invention is further modified to incorporate attenuating mutations selected from (i) a panel of mutations specifying temperature-sensitive amino acid substitutions Gln831 to Leu, and Tyr1321 to Asn in the RSV polymerase gene L; (ii) a temperature-sensitive nucleotide substitution in the gene-start sequence of gene M2; (iii) an attenuating panel of mutations adopted from cold-passaged RSV specifying amino acid substitutions Val267 Ile in the RSV N gene, and Cys319 Tyr and His1690 Tyr in the RSV polymerase gene L; or (iv) deletion or ablation of expression of one or more of the RSV SH, NS1, NS2, G and M2-2 genes. Preferably, these and other examples of human-bovine chimeric RSV incorporate at least two attenuating mutations adopted from biologically derived mutant RSV, which may be derived from the same or different biologically derived mutant RSV strains. Also preferably, these exemplary mutants have one or more of their attenuating mutations stabilized by multiple nucleotide changes in a codon specifying the mutation.

In accordance with the foregoing description, the ability to produce infectious RSV from cDNA permits introduction of specific engineered changes within human-bovine chimeric RSV. In particular, infectious, recombinant RSV are employed for identification of specific mutation(s) in biologically derived, attenuated RSV strains, for example mutations which specify ts, ca, att and other phenotypes. Desired mutations are thus identified and introduced into recombinant, human-bovine chimeric RSV vaccine strains. The capability of producing virus from cDNA allows for routine incorporation of these mutations, individually or in various selected combinations, into a full-length cDNA clone, whereafter the phenotypes of rescued recombinant viruses containing the introduced mutations to be readily determined.

By identifying and incorporating specific, biologically derived mutations associated with desired phenotypes, e.g., a cp or ts phenotype, into infectious chimeric RSV clones, the invention provides for other, site-specific modifications at, or within close proximity to, the identified mutation. Whereas most attenuating mutations produced in biologically derived RSV are single nucleotide changes, other "site specific" mutations can also be incorporated by recombinant techniques into biologically derived or recombinant RSV. As used herein, site-specific mutations include insertions, substitutions, deletions or rearrangements of from 1 to 3, up to about 5-15 or more altered nucleotides (e.g., altered from a wild-type RSV sequence, from a sequence of a selected mutant RSV strain, or from a parent recombinant RSV clone subjected to mutagenesis). Such site-specific mutations may be incorporated at, or within the region of, a selected, biologically derived mutation. Alternatively, the mutations can be introduced in various other contexts within an RSV clone, for example at or near a cis-acting regulatory sequence or nucleotide sequence encoding a protein active site, binding site, immunogenic epitope, etc. Site-specific RSV mutants typically retain a desired attenuating phenotype, but may additionally exhibit altered phenotypic characteristics unrelated to attenuation, e.g., enhanced or broadened immunogenicity, and/or improved growth. Further examples of desired, site-specific mutants include recombinant RSV designed to incorporate additional, stabilizing nucleotide mutations in a codon specifying an attenuating mutation. Where possible, two or more nucleotide substitutions are introduced at codons that specify attenuating amino acid changes in a parent mutant or recombinant RSV clone, yielding a biologically derived or recombinant RSV having genetic resistance to reversion from an attenuated phenotype. In other embodiments, site-specific nucleotide substitutions, additions, deletions or rearrangements are introduced upstream (N-terminal direction) or downstream (C-terminal direction), e.g., from 1 to 3, 5-10 and up to 15 nucleotides or more 5' or 3', relative to a targeted nucleotide position, e.g., to construct or ablate an existing cis-acting regulatory element.

In addition to single and multiple point mutations and site-specific mutations, changes to human-bovine chimeric RSV disclosed herein include deletions, insertions, substitutions or rearrangements of whole genes or genome segments. These mutations may alter small numbers of bases (e.g., from 15-30 bases, up to 35-50 bases or more), large blocks of nucleotides (e.g., 50-100, 100-300, 300-500, 500-1,000 bases), or nearly complete or complete genes (e.g., 1,000-1,500 nucleotides, 1,500-2,500 nucleotides, 2,500-5,000, nucleotides, 5,00-6,5000 nucleotides or more) in the donor or recipient genome or antigenome, depending upon the nature of the change (i.e., a small number of bases may be changed to insert or ablate an immunogenic epitope or change a small genome segment, whereas large block(s) of bases are involved when genes or large genome segments are added, substituted, deleted or rearranged.

In additional aspects, the invention provides for supplementation of mutations adopted into a chimeric RSV clone from biologically derived RSV, e.g., cp and ts mutations, with additional types of mutations involving the same or different genes in a further modified chimeric RSV clone. RSV encodes ten mRNAs and ten or eleven proteins. Three of these are transmembrane surface proteins, namely the attachment G protein, fusion F protein involved in penetration, and small hydrophobic SH protein. G and F are the major viral neutralization and protective antigens. Four additional proteins are associated with the viral nucleocapsid, namely the RNA binding protein N, the phosphoprotein P, the large polymerase protein L, and the transcription elongation factor M2 ORF1. A second ORF in M2, the M2-2 ORF encodes an important RNA regulatory factor. The matrix M protein is part of the inner virion and probably mediates association between the nucleocapsid and the envelope. Finally, there are two non-structural proteins, NS1 and NS2, of unknown function. Each of these proteins can be selectively altered in terms of expression levels, or can be added deleted, substituted or rearranged, in whole or in part, alone or in combination with other desired modifications, to yield a human-bovine chimeric RSV exhibiting novel vaccine characteristics.

Thus, in addition to or in combination with attenuating mutations adopted from biologically derived RSV mutants, the present invention also provides a range of additional methods for attenuating or otherwise modifying the phenotype of human-bovine chimeric RSV based on recombinant engineering of infectious RSV clones. A variety of alterations can be produced in an isolated polynucleotide sequence encoding the donor gene or genome segment or the background genome or antigenome for incorporation into infectious clones. More specifically, to achieve desired structural and phenotypic changes in chimeric RSV, the invention allow's for introduction of modifications which delete, substitute, introduce, or rearrange a selected nucleotide or plurality of nucleotides from a parent chimeric genome or antigenome, as well as mutations which delete, substitute, introduce or rearrange whole gene(s) or genome segment(s), within a human-bovine chimeric RSV clone.

Desired modifications of infectious human-bovine chimeric RSV are typically selected to specify a desired phenotypic change, e.g., a change in viral growth, temperature sensitivity, ability to elicit a host immune response, attenuation, etc. These changes can be brought about either in a donor or recipient genome or antigenome by, e.g., mutagenesis of a parent RSV clone to ablate, introduce or rearrange a specific gene(s) or genome region(s) (e.g., a genome segment that encodes a protein structural domain, such as a cytoplasmic, transmembrane or extracellular domain, an immunogenic epitope, binding region, active site, etc. or a cis-acting signal). Genes of interest in this regard include all of the genes of the RSV genome: 3'-NS1-NS2-N-P-M-SH-G-F-M21I/M2-2-L-5', as well as heterologous genes from other RSV, other viruses and a variety of other non-RSV sources as indicated herein.

Also provided are modifications in a human-bovine chimeric RSV which simply alter or ablate expression of a selected gene, e.g., by introducing a termination codon within a selected RSV coding sequence, changing the position of an RSV gene relative to an operably linked promoter, introducing an upstream start codon to alter rates of expression, modifying (e.g., by changing position, altering an existing sequence, or substituting an existing sequence with a heterologous sequence) GS and/or GE transcription signals to alter phenotype (e.g., growth, temperature restrictions on transcription, etc.), and various other deletions, substitutions, additions and rearrangements that specify quantitative or qualitative changes in viral replication, transcription of selected gene(s), or translation of selected protein(s).

The ability to analyze and incorporate other types of attenuating mutations into human-bovine chimeric RSV for vaccine development extends to a broad assemblage of targeted changes in RSV clones. For example, deletion of the SH gene yields a recombinant RSV having novel phenotypic characteristics, including enhanced growth. In the present invention, an SH, NS1 or NS2 gene (or any other selected, non-essential gene or genome segment) is deleted in a chimeric RSV, which may also have one or more additional mutations specifying an attenuated phenotype, e.g., one or more mutation(s) adopted from a biologically derived attenuated RSV mutant. In exemplary embodiments, an SH, NS1 or NS2 gene is deleted in combination with one or more cp and/or ts mutations adopted from cpts248/404, cpts530/1009, cpts530/1030, or another selected mutant RSV strain, to yield a recombinant RSV having increased yield of virus, enhanced attenuation, and resistance to phenotypic reversion, due to the combined effects of the different mutations.

Any RSV gene which is not essential for growth, for example the SH, NS1 NS2 or M2-2 genes, can be ablated or otherwise modified in a chimeric RSV to yield desired effects on virulence, pathogenesis, immunogenicity and other phenotypic characters. For example, ablation by deletion of a non-essential gene such as SH results in enhanced viral growth in culture. Without wishing to be bound by theory, this effect is likely due in part to a reduced nucleotide length of the viral genome. In the case of one exemplary SH-minus clone, the modified viral genome is 14,825 nt long, 398 nucleotides less than wild-type. By engineering similar mutations that decrease genome size, e.g., in other coding or noncoding regions elsewhere in the RSV genome, such as in the P, M, F and M2 genes, the invention provides several readily obtainable methods and materials for improving chimeric RSV growth.

In addition, a variety of other genetic alterations can be produced in a RSV genome or antigenome for incorporation into infectious human-bovine chimeric RSV, alone or together with one or more attenuating mutations adopted from a biologically derived mutant RSV. Additional heterologous genes and genome segments (e.g. from different RSV genes, different RSV strains or types, or non-RSV sources) may be inserted in whole or in part, the order of genes changed, gene overlap removed, an RSV genome promoter replaced with its antigenome counterpart, portions of genes removed or substituted, and even entire genes deleted. Different or additional modifications in the sequence can be made to facilitate manipulations, such as the insertion of unique restriction sites in various intergenic regions or elsewhere. Nontranslated gene sequences can be removed to increase capacity for inserting foreign sequences.

Also provided within the invention are genetic modifications in a human-bovine chimeric RSV which alter or ablate the expression of a selected gene or genome segment without removing the gene or genome segment from the chimeric RSV clone. For example, this can be achieved by introducing a frame shift mutation or termination codon within a selected coding sequence, changing the position of a gene or introducing an upstream start codon to alter its rate of expression, or changing GS and/or GE transcription signals to alter phenotype (e.g., growth, temperature restrictions on transcription, etc.). In one such example, expression of the M2-2 ORF is knocked out, which yields highly desired phenotypic changes for development of a vaccine virus, including altered growth kinetics, reduced RNA replication and increased transcription. Thus, the M2-2 knock-out exhibits significant attenuation with a concomitant increase, rather than decrease, in antigen expression.

In more detailed aspects of the invention, human-bovine chimeric RSV is provided in which expression of the NS2 gene is ablated at the translational level without deletion of the gene or of a segment thereof, by, e.g., introducing two tandem translational termination codons into a translational open reading frame (ORF). This yields viable virus in which a selected gene has been silenced at the level of translation without deleting its gene. These forms of knock-out virus will often exhibit reduced growth rates and small plaque sizes in tissue culture. Thus, these methods provide yet additional, novel types of attenuating mutations which ablate expression of a viral gene that is not one of the major viral protective antigens. In this context, knock-out virus phenotypes produced without deletion of a gene or genome segment can be alternatively produced by deletion mutagenesis, as described herein, to effectively preclude correcting mutations that may restore synthesis of a target protein. Several other gene knock-outs for human-bovine chimeric RSV can be made using alternate designs and methods that are well known in the art (as described, for example, in (Kretschmer et al., *Virology* 216:309-316, 1996; Radicle et al., *Virology* 217: 418-412, 1996; and Kato et al., *EMBOSS J.* 16:178-587, 1987; and Schneider et al., *Virology* 277:314-322, 1996, each incorporated herein by reference).

Other mutations for incorporation into human-bovine chimeric RSV of the invention include mutations directed toward cis-acting signals, which can be identified, e.g., by mutational analysis of RSV minigenomes. For example, insertional and deletional analysis of the leader and trailer and flanking sequences identifies viral promoters and transcription signals and provides a series of mutations associated with varying degrees of reduction of RNA replication or transcription. Saturation mutagenesis (whereby each position in turn is modified to each of the nucleotide alternatives) of these cis-acting signals also has identified many mutations which reduced (or in one case increased) RNA replication or transcription. Any of these mutations can be inserted into a human-bovine chimeric RSV antigenome or genome as described herein. Evaluation and manipulation of trans-acting proteins and cis-acting RNA sequences using the complete antigenome cDNA is assisted by the use of RSV minigenomes (see, e.g., Grosfeld et al., *J. Virol.* 69: 5677-5686, 1995, incorporated herein by reference), whose helper-dependent status is useful in the characterization of those mutants which are too inhibitory to be recovered in replication-independent infectious virus.

Additional mutations within human-bovine chimeric RSV involve replacement of the 3' end of genome with its counterpart from antigenome, which is associated with changes in RNA replication and transcription. In addition, the intergenic regions (Collins et al., *Proc. Natl. Acad. Sci. USA* 83:4594-4598, 1986, incorporated herein by reference) can be shortened or lengthened or changed in sequence content, and the naturally-occurring gene overlap (Collins et al., *Proc. Natl. Acad. Sci. USA* 84:5134-5138, 1987, incorporated herein by reference) can be removed or changed to a different intergenic region by the methods described herein. In one exemplary embodiment, the level of expression of specific RSV proteins, such as the protective F and G antigens, can be increased by substituting the natural sequences with ones which have been made synthetically and designed to be consistent with efficient translation. In this context, it has been shown that codon usage can be a major factor in the level of translation of mammalian viral proteins (Haas et al., *Current Biol.* 6:315-324, 1996, incorporated herein by reference). Examination of the codon usage of the mRNAs encoding the F and G proteins of RSV, which are the major protective antigens, shows that the usage is consistent with poor expression. Thus, codon usage can be improved by the recombinant methods of the invention to achieve improved expression for selected genes. In another exemplary embodiment, a sequence surrounding a translational start site (preferably including a nucleotide in the −3 position) of a selected RSV gene is modified, alone or in combination with introduction of an upstream start codon, to modulate chimeric RSV gene expression by specifying up- or down-regulation of translation.

Alternatively, or in combination with other RSV modifications disclosed herein, human-bovine chimeric RSV gene expression can be modulated by altering a transcriptional GS signal of a selected gene(s) of the virus. In one exemplary embodiment, the GS signal of NS2 is modified to include a defined mutation (e.g., the 404(M2) mutation described herein below) to superimpose a ts restriction on viral replication.

In alternative embodiments, levels of gene expression in the human-bovine chimeric RSV are modified at the level of transcription. In one aspect, the position of a selected gene in the RSV gene map can be changed to a more promoter-proximal or promoter-distal position, whereby the gene will be expressed more or less efficiently, respectively. According to this aspect, modulation of expression for specific genes can be achieved yielding reductions or increases of gene expression from two-fold, more typically four-fold, up to ten-fold or more compared to wild-type levels often attended by a commensurate decrease in expression levels for reciprocally, positionally substituted genes. In one example, the NS2 gene (second in order in the RSV gene map) is substituted in position for the SH gene (sixth in order), yielding a predicted decrease in expression of NS2. In other exemplary embodiments, the F and G genes are transpositioned singly or together to a more promoter-proximal or promoter-distal site within the chimeric RSV gene map to achieve higher or lower levels of gene expression, respectively. These and other transpositioning changes yield novel chimeric RSV clones having attenuated phenotypes, for example due to decreased expression of selected viral proteins involved in RNA replication, or having other desirable properties such as increased antigen expression.

Infectious human-bovine chimeric RSV clones of the invention can also be engineered according to the methods and compositions disclosed herein to enhance immunogenicity and induce a level of protection greater than that provided by infection with a wild-type RSV or a parent chimeric RSV. For example, an immunogenic epitope from a heterologous RSV strain or type, or from a non-RSV source such as PIV, can be added to a chimeric clone by appropriate nucleotide changes in the polynucleotide sequence encoding the chimeric genome or antigenome. Alternatively, chimeric RSV can be engineered to add or ablate (e.g., by amino acid insertion, substitution or deletion) immunogenic proteins, protein domains, or forms of specific proteins (such as the secreted form of G) associated with desirable or undesirable immunological reactions.

Within the methods of the invention, additional genes or genome segments may be inserted into or proximate to the human-bovine chimeric RSV genome or antigenome. These genes may be under common control with recipient genes, or may be under the control of an independent set of transcription signals. Genes of interest include the RSV genes identified above, as well as non-RSV genes. Non-RSV genes of interest include those encoding cytokines (e.g., IL-2 through IL-18, especially IL-2, IL-6 and IL-12, IL-18, etc.), gamma-interferon, and proteins rich in T helper cell epitopes. These additional proteins can be expressed either as a separate protein, or as a chimera engineered from a second copy of one of the RSV proteins, such as SH. This provides the ability to modify and improve the immune responses against RSV both quantitatively and qualitatively.

In exemplary embodiments of the invention, insertion of foreign genes or genome segments, and in some cases of noncoding nucleotide sequences, within a human-bovine chimeric RSV genome results in a desired increase in genome length causing yet additional, desired phenotypic effects. Increased genome length results in attenuation of the resultant RSV, dependent in part upon the length of the insert. In addition, the expression of certain proteins, e.g. a cytokine, from a non-RSV gene inserted into human-bovine chimeric RSV will result in attenuation of the virus due to the action of the protein. Exemplary cytokines that yield an infectious, attenuated viral phenotype and high level cytokine expression from RSV transfected cells include interleukin-2 (IL-2), IL-4, GM-CSF, and γ-interferon. Additional effects including augmentation of cellular and or humoral immune responses will also attend introduction of cytokines into human-bovine chimeric RSV of the invention.

Deletions, insertions, substitutions and other mutations involving changes of whole viral genes or genome segments within human-bovine chimeric RSV of the invention yield highly stable vaccine candidates, which are particularly important in the case of immunosuppressed individuals. Many of these changes will result in attenuation of resultant vaccine strains, whereas others will specify different types of desired phenotypic changes. For example, accessory (i.e., not essential for in vitro growth) genes are excellent candidates to encode proteins that specifically interfere with host immunity (see, e.g., Kato et al., *EMBO. J.* 16:578-87, 1997, incorporated herein by reference). Ablation of such genes in chimeric vaccine viruses is expected to reduce virulence and pathogenesis and/or improve immunogenicity.

In alternative aspects of the invention, the infectious human-bovine chimeric RSV produced from a cDNA-expressed genome or antigenome can be any of the RSV or RSV-like strains, e.g., human, bovine, murine, etc., or of any pneumovirus, e.g., pneumonia virus of mice avian pneumovirus (previously called turkey rhinotracheitis virus). To engender a protective immune response, the RSV strain may be one which is endogenous to the subject being immunized, such as human RSV being used to immunize humans. The genome or antigenome of endogenous RSV can be modified, however, to express RSV genes or genome segments from a combination of different sources, e.g., a combination of genes or genome segments from different RSV species, subgroups, or strains, or from an RSV and another respiratory pathogen such as PIV.

In certain embodiments of the invention, human-bovine chimeric RSV are provided wherein genes or genome segments within a human or bovine RSV (e.g., a human RSV background genome or antigenome) are replaced with counterpart heterologous genes or genome segments from a non-human, non-bovine RSV, e.g., a murine RSV. Substitutions, deletions, and additions of RSV genes or genome segments in this context can include part or all of one or more of the NS1, NS2, N, P, M, SH, M2(ORF1), M2(ORF2) and L genes, or parts of the G and F genes which preferably are outside of the major neutralization and protective epitopes. Also, human or bovine RSV cis-acting sequences, such as promoter or transcription signals, can be replaced with non-human, non-bovine counterpart sequences. Thus, infectious human-bovine chimeric RSV intended for administration to humans can be a human RSV that has been modified to contain genes from a murine RSV in addition to bovine RSV.

Replacement of a human RSV coding sequence (e.g., of NS1, NS2, SH, G, M2-2) or non-coding sequence (e.g., a promoter, gene-end, gene-start, intergenic or other cis-acting element) with a counterpart bovine or murine RSV sequence yields chimeric RSV having a variety of possible attenuating and other phenotypic effects. In particular, host range and other desired effects arise from substituting a bovine or murine RSV gene imported within a human RSV background, wherein the bovine or murine gene does not function efficiently in a human cell, e.g., from incompatibility of the heterologous sequence or protein with a biologically interactive human RSV sequence or protein (i.e., a sequence or protein that ordinarily cooperates with the substituted sequence or protein for viral transcription, translation, assembly, etc.) or, more typically in a host range restriction, with a cellular protein or some other aspect of the cellular milieu which is different between the permissive and less permissive host. In one such embodiment, a chimeric bovine-human RSV incorporates a substitution of the human RSV NP gene or genome segment with a counterpart bovine NP gene or genome segment, which chimera can optionally be constructed to incorporate additional genetic changes, e.g., point mutations or gene deletions. Chimeric human-bovine RSV bearing heterologous genes or cis-acting elements are selected for host range restriction and other desired phenotypes favorable for vaccine use. In exemplary embodiments, bovine RSV sequences are selected for introduction into human RSV based on known aspects of bovine RSV structure and function, as provided in, e.g., Pastey et al., *J. Gen. Viol.* 76:193-197, 1993; Pastey et al., *Virus Res.* 29:195-202, 1993; Zamora et al., *J. Gen. Virol.* 73:737-741, 1992; Mallipeddi et al., *J. Gen. Virol.* 74:2001-2004, 1993; Mallipeddi et al., *J. Gen. Virol.* 73:2441-2444, 1992; and Zamora et al., *Virus Res.* 24:115-121, 1992, each incorporated herein by reference, and in accordance with the teachings disclosed herein.

In other embodiments of the invention, mutations of interest for introduction within human-bovine chimeric RSV are modeled after a tissue culture-adapted nonpathogenic strain of pneumonia virus of mice (the murine counterpart of human RSV) which lacks a cytoplasmic tail of the G protein (Randhawa et al., *Virology* 207:240-245, 1995). Accordingly, in one aspect of the invention the cytoplasmic and/or transmembrane domains of one or more of the human RSV glycoproteins, F, G and SH, are added, deleted, modified, or substituted within a chimeric RSV using a heterologous counterpart sequence (e.g., a sequence from a cytoplasmic, or transmembrane domain of a F, G, or SH protein of murine pneumonia virus) to achieve a desired attenuation. As another example, a nucleotide sequence at or near the cleavage site of the F protein, or the putative attachment domain of the G protein, can be modified by point mutations, site-specific changes, or by alterations involving entire genes or genome segments to achieve novel effects on viral growth in tissue culture and/or infection and pathogenesis.

In more detailed aspects of the invention, human-bovine chimeric RSV are employed as vectors for protective antigens of other pathogens, particularly respiratory tract pathogens such as parainfluenza virus (PIV). For example, chimeric RSV may be engineered which incorporate sequences that encode protective antigens from PIV to produce infectious, attenuated vaccine virus. The cloning of PIV cDNA and other disclosure for implementing these and other more detailed aspects of the invention is provided in U.S. patent application Ser. No. 09/083,793 (corresponding to International Publication No. WO 98/53078) and its priority, U.S. provisional application Ser. No. 60/047,575; U.S. patent application Ser. No. 09/350,821; and U.S. patent application Ser. No. 09/586, 479 and its priority, provisional application Ser. No. 60/143, 134, each incorporated herein by reference. These disclosures include description of the following plasmids that may be employed to produce infectious PIV viral clones: p3/7(131) (ATCC 97990); p3/7(131)2G (ATCC 97989); and p218(131) (ATCC 97991); each deposited under the terms of the Budapest Treaty with the American Type Culture Collection (ATCC) of 10801 University Boulevard, Manassas, Va. 20110-2209, U.S.A., and granted the above identified accession numbers.

According to this aspect of the invention, a human-bovine chimeric RSV is provided which comprises a chimera of a bovine and human RSV genomic or antigenomic sequence and at least one PIV sequence, for example a polynucleotide containing sequences from both bovine and human RSV, and PIV1, PIV2, PIV3 or bovine PIV. For example, individual genes of RSV may be replaced with counterpart genes from human PIV, such as the F glycoprotein genes of PIV1, PIV2, or PIV3. Alternatively, a selected, heterologous genome segment, such as a cytoplasmic tail, transmembrane domain or ectodomain of substituted for a counterpart genome segment in, e.g., the same gene in RSV, within a different gene in RSV, or into a non-coding sequence of the RSV genome or antigenome. In one embodiment, a genome segment from an F gene of HPIV3 is substituted for a counterpart human RSV genome segment to yield constructs encoding chimeric proteins, e.g. fusion proteins having a cytoplasmic tail and/or transmembrane domain of RSV fused to an ectodomain of RSV to yield a novel attenuated virus, and/or a multivalent vaccine immunogenic against both PIV and RSV. The cloning of PIV cDNA and other disclosure for implementing these and other more detailed aspects of the invention is provided in U.S. patent application Ser. No. 09/083,793 (corresponding to International Publication No. WO 98/53078) and its priority, provisional application Ser. No. 60/047,575; U.S. patent application Ser. No. 09/350,821; and U.S. patent application Ser. No. 09/586,479 and its priority, provisional application Ser. No. 60/143,134, each incorporated herein by reference.

Thus human-bovine chimeric RSV of the invention may be employed as vectors for expressing antigenic determinants of a wide variety of other pathogens. Typically, a bovine-human chimeric genome or antigenome is employed as partial or complete RSV vector genome or antigenome. Incorporated within the vector genome or antigenome is one or more heterologous genes or genome segments encoding antigenic determinant(s) of one or more heterologous pathogens. In certain embodiments, the heterologous pathogen is a heterologous RSV, and the heterologous gene(s) or genome segment(s) incorporated in the human-bovine chimeric RSV vector genome or antigenome encode(s) one or more RSV NS1, NS2, N, P, M, SH, M2(ORF1), M2(ORF2), L, F or G protein(s) or fragment(s) thereof. For example, the vector genome or antigenome may include a partial or complete RSV A genome or antigenome, and the heterologous gene or genome segment encoding the antigenic determinant may be of a RSV B subgroup virus.

In other alternative embodiments, the human-bovine chimeric RSV is employed as a vector for expressing one or more antigenic determinants of a non-RSV pathogen. The chimeric vector virus thus constructed may express antigenic determinants of RSV as well as of the non-RSV pathogen, or may elicit a mono-specific immune response against the non-RSV pathogen. In one embodiment, human-bovine chimeric RSV incorporate one or more HPIV1, HPIV2, or HPIV3 gene(s) or genome segment(s) encoding one or more HN and/or F glycoprotein(s) or antigenic domain(s), fragment(s) or epitope(s) thereof. In more detailed aspects, a transcription unit comprising an open reading frame (ORF) of an HPIV2 HN or F gene is added to or incorporated within the chimeric HBRSV vector genome or antigenome.

Human-bovine chimeric RSV employed as vectors include chimeric RSV wherein the vector genome or antigenome is a partial or complete BRSV genome or antigenome, and the heterologous gene(s) or genome segment(s) encoding the antigenic determinant(s) is/are of one or more HRSV(s). For example, the partial or complete BRSV genome or antigenome may incorporate one or more gene(s) or genome segment(s) encoding one or more HRSV glycoprotein genes selected from F, G and SH, or one or more genome segment(s) encoding cytoplasmic domain, transmembrane domain, ectodomain or immunogenic epitope portion(s) of F, G, and/or SH of HRSV.

In yet additional vector constructs of the invention, the vector genome or antigenome includes a partial or complete HRSV or BRSV genome or antigenome, and the heterologous pathogen is selected from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses. From these and other pathogens, useful heterologous antigenic determinant(s) for incorporation within the human-bovine chimeric RSV may be selected from measles virus HA and F proteins, subgroup A or subgroup B respiratory syncytial virus F, G, SH and M2 proteins, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein; filovirus G protein, bunyavirus G protein, Flavivirus E and NS1 proteins, and alphavirus E protein, and antigenic domains, fragments and epitopes thereof. For example, a human-bovine chimeric RSV of the invention may be used as a vector wherein heterologous pathogen is measles virus and the heterologous antigenic determinant(s) is/are selected from the measles virus HA and F proteins and antigenic domains, fragments and epitopes thereof. To construct such recombinants, a transcription unit comprising an open reading frame (ORF) of a measles virus HA gene is added to or incorporated within a HRSV vector genome or antigenome. Similar recombinants are readily constructed for other non-RSV pathogens in accordance with the teachings of the present disclosure.

In addition to the above described modifications to human-bovine chimeric RSV, different or additional modifications in RSV clones can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences.

In another aspect of the invention, compositions (e.g., isolated polynucleotides and vectors incorporating a human-bovine chimeric RSV-encoding cDNA) are provided for producing an isolated infectious chimeric RSV. Using these compositions and methods, infectious chimeric RSV are generated from a chimeric RSV genome or antigenome, a nucleocapsid (N) protein, a nucleocapsid phosphoprotein (P), a large (L) polymerase protein, and an RNA polymerase elongation factor. In related aspects of the invention, compositions and methods are provided for introducing the aforementioned structural and phenotypic changes into a recombinant chimeric RSV to yield infectious, attenuated vaccine viruses.

Introduction of the foregoing defined mutations into an infectious, human-bovine chimeric RSV clone can be achieved by a variety of well known methods. By "infectious clone" with regard to DNA is meant cDNA or its product, synthetic or otherwise, which can be transcribed into genomic or antigenomic RNA capable of serving as template to produce the genome of an infectious virus or subviral particle. Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA as described herein has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. This can be through the intermediate of a single-stranded phagemid form, such as using the Muta-gene kit of Bio-Rad Laboratories (Richmond, Calif.) or a method using a double-stranded plasmid directly as template such as the Chameleon mutagenesis kit of Stratagene (La Jolla, Calif.), or by the polymerase chain reaction employing either an oligonucleotide primer or template which contains the mutation(s) of interest. A mutated subfragment can then be assembled into the complete antigenome or genome cDNA. A variety of other mutagenesis techniques are known and available for use in producing the mutations of interest in the RSV antigenome or genome cDNA. Mutations can vary from single nucleotide changes to replacement of large cDNA pieces containing one or more genes or genome regions.

Thus, in one illustrative embodiment mutations are introduced by using the Muta-gene phagemid in vitro mutagenesis kit available from Bio-Rad. In brief, cDNA encoding a portion of an RSV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome fragment is then amplified and the mutated piece is then reintroduced into the full-length genome or antigenome clone.

The ability to introduce defined mutations into infectious RSV has many applications, including the analyses of RSV molecular biology and pathogenesis. For example, the functions of RSV proteins can be investigated and manipulated by introducing mutations which ablate or reduce their level of expression, or which yield mutant protein. In one exemplary embodiment, recombinant RSV is constructed in which expression of a viral gene, namely the SH gene, is ablated, e.g., by deletion of the mRNA coding sequence and flanking transcription signals. Surprisingly, not only could this virus be recovered, but it grew efficiently in tissue culture. In fact, its growth was substantially increased over that of the wild-type, based on both yield of infectious virus and on plaque size. This improved growth in tissue culture from the SH deletion and other RSV derivatives of the invention provides useful tools for developing RSV vaccines, which overcome the problem of RSV's poor yield in tissue culture that had complicated production of vaccine virus in other systems. These deletions are highly stable against genetic reversion, rendering the RSV clones derived therefrom particularly useful as vaccine agents.

In another exemplary embodiment, chimeric RSV are provided that incorporate a mutation that deletes the M2 gene (M2ORF2) (Collins and Wertz, *J. Virol.* 54:65-71, 1985; Collins et al., *J. Gen. Virol.* 71:3015-3020, 1990, Collins et al., *Proc. Natl. Acad. Sci. USA* 93:81-85, 1996, each incorporated herein by reference), or reduces or ablates expression of M2 ORF2 to yield novel RSV vaccine candidates (see U.S. Provisional Patent Application No. 60/143,097, filed by Collins et al. on Jul. 9, 1999, incorporated herein by reference). In preferred aspects, expression of M2 ORF2 is reduced or ablated by modifying the chimeric RSV genome or antigenome to incorporate a frame shift mutation or one or stop codons in M2 ORF2 yielding a "knock out" viral clone. Alternatively, M2 ORF2 is deleted in whole or in part to render the M2-2 protein partially or entirely non-functional or to disrupt its expression altogether to yield a M2 ORF2 "deletion mutant" chimeric RSV. Alternatively, the M2-2 ORF may be transpositioned in the genome or antigenome to a more promoter-proximal or promoter-distal position compared to the natural gene order position of M2-2 gene to up-regulate or down-regulate expression of the M2-2 ORF. In additional embodiments, the M2-2 ORF is incorporated in the genome or antigenome as a separate gene having a gene start and gene end gene end signal, which modification results in up-regulation of the M2-2 ORF.

The chimeric RSV of the invention further modified to incorporate mutations in M2 ORF2 possess highly desirable phenotypic characteristics for vaccine development. The above identified modifications in the chimeric genome or antigenome specify one or more desired phenotypic changes in the resulting virus or subviral particle. Vaccine candidates are thus generated that exhibit one or more characteristics identified as (i) a change in mRNA transcription, (ii) a change in the level of viral protein expression; (iii) a change in genomic or antigenomic RNA replication, (iv) a change in viral growth characteristics, (v), a change in viral plaque size, and/or (vi) a change in cytopathogenicity.

In exemplary RSV chimeras incorporating an M2 ORF 2 deletion or knock out mutation, desired phenotypic changes include attenuation of viral growth compared to growth of a corresponding wild-type or mutant parental RSV strain. In more detailed aspects, viral growth in cell culture may be attenuated by approximately 10-fold or more attributable to mutations in M2 ORF2. Kinetics of viral growth are also shown to be modified in a manner that is beneficial for vaccine development.

Also included within the invention are chimeric, M2-ORF 2 deletion and knock out mutant RSV that exhibit delayed kinetics of viral mRNA synthesis compared to kinetics of mRNA synthesis of corresponding wild-type or mutant parental RSV strains. Despite these delayed transcription kinetics, these novel vaccine candidates exhibit an increase in cumulative mRNA synthesis compared to parental virus. These phenotypic changes typically are associated with an increase in viral protein accumulation in infected cells compared to protein accumulation in cells infected with wild-type or other parental RSV strains. At the same time, viral RNA replication is reduced in M2 ORF2 chimeric RSV compared to that of a parental RSV strain having normal M2 ORF2 function, whereby accumulation of genomic or antigenomic RNA is reduced.

Within preferred aspects of the invention, chimeric M2 ORF2 deletion and "knock out" RSV are engineered to express undiminished or, more typically, increased levels of viral antigen(s) while also exhibiting an attenuated phenotype. Immunogenic potential is thus preserved due to the undiminished or increased mRNA transcription and antigen expression, while attenuation is achieved through incorporation of the heterologous gene(s) or gene segment(s) and concomitant reductions in RNA replication and virus growth attributable to the M2-ORF 2 deletion and knock out mutation. This novel suite of phenotypic traits is highly desired for vaccine development. Other useful phenotypic changes that are observed in M2 ORF2 deletion and knock out chimeric RSV include a large plaque phenotype and altered cytopathogenicity compared to corresponding wild-type or mutant parental RSV strains.

The invention also provides methods for producing an infectious human-bovine chimeric RSV from one or more isolated polynucleotides, e.g., one or more cDNAs. According to the present invention cDNA encoding a RSV genome or antigenome is constructed for intracellular or in vitro coexpression with the necessary viral proteins to form infectious RSV. By "RSV antigenome" is meant an isolated positive-sense polynucleotide molecule which serves as the template for the synthesis of progeny RSV genome. Preferably a cDNA is constructed which is a positive-sense version of the RSV genome, corresponding to the replicative intermediate RNA, or antigenome, so as to minimize the possibility of hybridizing with positive-sense transcripts of the complementing sequences that encode proteins necessary to generate a transcribing, replicating nucleocapsid, i.e., sequences that encode N, P, L and M2(ORF1) protein. In an RSV minigenome system, genome and antigenome were equally active in rescue, whether complemented by RSV or by plasmids, indicating that either genome or antigenome can be used and thus the choice can be made on methodologic or other grounds.

A native RSV genome typically comprises a negative-sense polynucleotide molecule which, through complementary viral mRNAs, encodes eleven species of viral proteins, i.e., the nonstructural species NS1 and NS2, N, P, matrix (M), small hydrophobic (SH), glycoprotein (G), fusion (F), M2(ORF1), M2(ORF2), and L, substantially as described in (Mink et al., *Virology* 185:615-624, 1991; Stec et al., *Virology* 183:273-287, 1991; and Connors et al., *Virol.* 208:478-484, 1995; Collins et al., *Proc. Nat. Acad. Sci. USA* 93:81-85, 1996), each incorporated herein by reference. For purposes of the present invention the genome or antigenome of the recombinant RSV of the invention need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule, or can be expressed directly from the genome or antigenome cDNA.

By recombinant RSV is meant a RSV or RSV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in RSV gene expression, for example, a promoter, a structural or coding sequence which is transcribed into RSV RNA, and appropriate transcription initiation and termination sequences.

To produce infectious RSV from cDNA-expressed genome or antigenome, the genome or antigenome is coexpressed with those RSV proteins necessary to (i) produce a nucleocapsid capable of RNA replication, and (ii) render progeny nucleocapsids competent for both RNA replication and transcription. Transcription by the genome nucleocapsid provides the other RSV proteins and initiates a productive infection. Alternatively, additional RSV proteins needed for a productive infection can be supplied by coexpression.

An RSV antigenome may be constructed for use in the present invention by assembling cloned cDNA segments, representing in aggregate the complete antigenome, by polymerase chain reaction (PCR; described in, e.g., U.S. Pat. Nos. 4,683,195 and 4,683,202, and *PCR Protocols*: A Guide to Methods and Applications, Innis et al., eds., Academic Press, San Diego, 1990, incorporated herein by reference) of reverse-transcribed copies of RSV mRNA or genome RNA. For example, cDNAs containing the lefthand end of the antigenome, spanning from an appropriate promoter (e.g., T7 RNA polymerase promoter) and the leader region complement to the SH gene, are assembled in an appropriate expression vector, such as a plasmid (e.g., pBR322) or various available cosmid, phage, or DNA virus vectors. The vector may be modified by mutagenesis and/or insertion of synthetic polylinker containing unique restriction sites designed to facilitate assembly. For example, a plasmid vector described herein was derived from pBR322 by replacement of the PstI-EcoRI fragment with a synthetic DNA containing convenient restriction enzyme sites. Use of pBR322 as a vector stabilized nucleotides 3716-3732 of the RSV sequence, which otherwise sustained nucleotide deletions or insertions, and propagation of the plasmid was in bacterial strain DH10B to avoid an artifactual duplication and insertion which otherwise occurred in the vicinity of nt 4499. For ease of preparation the G, F and M2 genes can be assembled in a separate vector, as can be the L and trailer sequences. The right-hand end (e.g., L and trailer sequences) of the antigenome plasmid may contain additional sequences as desired, such as a flanking ribozyme and tandem T7 transcriptional terminators. The ribozyme can be hammerhead type (e.g., Grosfeld et al., *J. Virol.* 69:5677-5686, 1995), which would yield a 3' end containing a single nonviral nucleotide, or can any of the other suitable ribozymes such as that of hepatitis delta virus (Perrotta et al., *Nature* 350:434-436, 1991) which would yield a 3' end free of non-RSV nucleotides. A middle segment (e.g., G-to-M2 piece) is inserted into an appropriate restriction site of the leader-to-SH plasmid, which in turn is the recipient for the L-trailer-ribozyme-terminator piece, yielding a complete antigenome. In an illustrative example described herein, the leader end was constructed to abut the promoter for T7 RNA polymerase which included three transcribed G residues for optimal activity; transcription donates these three nonviral G's to the 5' end of the antigenome. These three nonviral G residues can be omitted to yield a 5' end free of nonviral nucleotides. To generate a nearly correct 3' end, the trailer end was constructed to be adjacent to a hammerhead ribozyme, which upon cleavage would donate a single 3'-phosphorylated U residue to the 3' end of the encoded RNA.

In certain embodiments of the invention, complementing sequences encoding proteins necessary to generate a transcribing, replicating RSV nucleocapsid are provided by one or more helper viruses. Such helper viruses can be wild-type or mutant. Preferably, the helper virus can be distinguished phenotypically from the virus encoded by the RSV cDNA. For example, it is desirable to provide monoclonal antibodies which react immunologically with the helper virus but not the virus encoded by the RSV cDNA. Such antibodies can be neutralizing antibodies. In some embodiments, the antibodies can be used to neutralize the helper virus background to facilitate identification and recovery of the recombinant virus, or in affinity chromatography to separate the helper virus from the recombinant virus. Mutations can be introduced into the RSV cDNA which render the recombinant RSV nonreactive or resistant to neutralization with such antibodies.

A variety of nucleotide insertions and deletions can be made in the human-bovine chimeric RSV genome or antigenome to generate a properly attenuated clone. The nucleotide length of the genome of wild-type human RSV (15,222 nucleotides) is a multiple of six, and members of the Paramyxovirus and Morbillivirus genera typically abide by a "rule of six," i.e., genomes (or minigenomes) replicate efficiently only when their nucleotide length is a multiple of six (thought to be a requirement for precise spacing of nucleotide residues relative to encapsidating NP protein). Alteration of RSV genome length by single residue increments had no effect on the efficiency of replication, and sequence analysis of several different minigenome mutants following passage showed that the length differences were maintained without compensatory changes. Thus, RSV lacks the strict requirement of genome length being a multiple of six, and nucleotide insertions and deletions can be made in the RSV genome or antigenome without defeating replication of the recombinant RSV of the present invention.

Alternative means to construct cDNA encoding a human-bovine chimeric RSV genome or antigenome include by reverse transcription-PCR using improved PCR conditions (e.g., as described in Cheng et al., *Proc. Natl. Acad. Sci. USA* 91:5695-5699, 1994; Samal et al., *J. Virol.* 70:5075-5082, 1996, each incorporated herein by reference) to reduce the number of subunit cDNA components to as few as one or two pieces. In other embodiments different promoters can be used (e.g., T3, SP6) or different ribozymes (e.g., that of hepatitis delta virus. Different DNA vectors (e.g., cosmids) can be used for propagation to better accommodate the large size genome or antigenome.

The N, P and L proteins, necessary for RNA replication, require an RNA polymerase elongation factor such as the M2(ORF1) protein for processive transcription. Thus M2(ORF1) or a substantially equivalent transcription elongation factor for negative strand RNA viruses is required for the production of infectious RSV and is a necessary component of functional nucleocapsids during productive infection.

The need for the M2(ORF1) protein is consistent with its role as a transcription elongation factor. The need for expression of the RNA polymerase elongation factor protein for negative strand RNA viruses is a feature of the present invention. M2(ORF1) can be supplied by expression of the complete M2-gene, either by the chimeric genome or antigenome or by coexpression therewith, although in this form the second ORF2 may also be expressed and have an inhibitory effect on RNA replication. Therefore, for production of infectious virus using the complete M2 gene the activities of the two ORFs should be balanced to permit sufficient expression of M(ORF1) to provide transcription elongation activity yet not so much of M(ORF2) to inhibit RNA replication. Alternatively, the ORF1 protein is provided from a cDNA engineered to lack ORF2 or which encodes a defective ORF2. Efficiency of virus production may also be improved by co-expression of additional viral protein genes, such as those encoding envelope constituents (i.e., SH, M, G, F proteins).

Isolated polynucleotides (e.g., cDNA) or expressed from the antigenome or genome cDNA, encoding the human-bovine chimeric RSV genome or antigenome and, separately, or in cis, or expressed from the antigenome or genome cDNA, the N, P, L and M2(ORF1) proteins, are inserted by transfection, electroporation, mechanical insertion, transduction or the like, into cells which are capable of supporting a productive RSV infection, e.g., HEp-2, FRhL-DBS2, MRC, and Vero cells. Transfection of isolated polynucleotide sequences may be introduced into cultured cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841-845, 1982), DEAE-dextran mediated transfection (Ausubel et al., (ed.) *Current Protocols in Molecular Biology*, John Wiley and Sons, Inc., NY, 1987, cationic lipid-mediated transfection (Hawley-Nelson et al., *Focus* 15:73-79, 1993) or a commercially available transfection regent, e.g., LipofectACE® (Life Technologies) (each of the foregoing references are incorporated herein by reference).

The N, P, L and M2(ORF1) proteins are encoded by one or more cDNAs and expression vectors which can be the same or separate from that which encodes the genome or antigenome, and various combinations thereof. Additional proteins may be included as desired, encoded by its own vector or by a vector encoding a N, P, L, or M2(ORF1) protein and/or the complete genome or antigenome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., *Virology,* 210:202-205, 1995, incorporated herein by reference). The viral proteins, and/or T7 RNA polymerase, can also be provided from transformed mammalian cells, or by transfection of preformed mRNA or protein.

Alternatively, synthesis of antigenome or genome can be conducted in vitro (cell-free) in a combined transcription-translation reaction, followed by transfection into cells. Or, antigenome or genome RNA can be synthesized in vitro and transfected into cells expressing RSV proteins.

To select candidate chimeric vaccine viruses according to the invention, the criteria of viability, attenuation and immunogenicity are determined according to well known methods. Viruses which will be most desired in vaccines of the invention must maintain viability, have a stable attenuation phenotype, exhibit replication in an immunized host (albeit at lower levels), and effectively elicit production of an immune response in a vaccinee sufficient to confer protection against serious disease caused by subsequent infection from wild-type virus. Clearly, the heretofore known and reported RS virus mutants do not meet all of these criteria. Indeed, contrary to expectations based on the results reported for known attenuated RSV, viruses of the invention are not only viable and more appropriately attenuated than previous mutants, but are more stable genetically in vivo than those previously studied mutants—retaining the ability to stimulate a protective immune response and in some instances to expand the protection afforded by multiple modifications, e.g., induce protection against different viral strains or subgroups, or protection by a different immunologic basis, e.g., secretory versus serum immunoglobulins, cellular immunity, and the like. Prior to the invention, genetic instability of the ts phenotype following replication in vivo has been common for ts viruses (Murphy et al., *Infect. Immun.* 37:235-242, 1982).

To propagate a human-bovine chimeric RSV virus for vaccine use and other purposes, a number of cell lines which allow for RSV growth may be used. RSV grows in a variety of human and animal cells. Preferred cell lines for propagating attenuated RS virus for vaccine use include DBS-FRhL-2, MRC-5, and Vero cells. Highest virus yields are usually achieved with epithelial cell lines such as Vero cells. Cells are typically inoculated with virus at a multiplicity of infection ranging from about 0.001 to 1.0 or more, and are cultivated under conditions permissive for replication of the virus, e.g., at about 30-37° C. and for about 3-5 days, or as long as necessary for virus to reach an adequate titer. Virus is removed from cell culture and separated from cellular components, typically by well known clarification procedures, e.g., centrifugation, and may be further purified as desired using procedures well known to those skilled in the art.

Human-bovine chimeric RSV which has been attenuated and otherwise modified as described herein can be tested in various well known and generally accepted in vitro and in vivo models to confirm adequate attenuation, resistance to phenotypic reversion, and immunogenicity for vaccine use. In in vitro assays, the modified virus (e.g., a multiply attenuated, biologically derived or recombinant RSV) is tested for temperature sensitivity of virus replication, i.e. ts phenotype, and for the small plaque phenotype. Modified viruses are further tested in animal models of RSV infection. A variety of animal models have been described and are summarized in (Meignier et al., eds., Animal Models of Respiratory Syncytial Virus Infection, Merieux Foundation Publication, 1991, which is incorporated herein by reference). A cotton rat model of RSV infection is described in (U.S. Pat. No. 4,800,078 and Prince et al., *Virus Res.* 3:193-206, 1985), which are incorporated herein by reference, and is considered predictive of attenuation and efficacy in humans and non-human primates. In addition, a primate model of RSV infection using the chimpanzee is predictive of attenuation and efficacy in humans, as is described in detail in (Richardson et al., *J. Med. Virol.* 3:91-100, 1978; Wright et al., *Infect. Immun.* 37:397-400, 1982; Crowe et al., *Vaccine* 111:1395-1404, 1993, each incorporated herein by reference).

RSV model systems, including rodents and chimpanzees for evaluating attenuation and infectivity of RSV vaccine candidates are widely accepted in the art and the data obtained therefrom correlate well with RSV infection and attenuation. The mouse and cotton rat models are especially useful in those instances in which candidate RSV viruses display inadequate growth in chimpanzees, for example in the case of RSV subgroup B viruses.

In accordance with the foregoing description and based on the examples below, the invention also provides isolated, infectious human-bovine chimeric RSV compositions for vaccine use. The attenuated chimeric virus which is a component of a vaccine is in an isolated and typically purified form. By isolated is meant to refer to RSV which is in other than a native environment of a wild-type virus, such as the nasopharynx of an infected individual. More generally, isolated is meant to include the attenuated virus as a component of a cell culture or other artificial medium where it can be propagated and characterized in a controlled setting. For example, attenuated RSV of the invention may be produced by an infected cell culture, separated from the cell culture and added to a stabilizer.

Chimeric RSV vaccines of the invention contain as an active ingredient an immunogenically effective amount of RSV produced as described herein. Biologically derived or recombinant RSV can be used directly in vaccine formulations, or lyophilized. Lyophilized virus will typically be maintained at about 4° C. When ready for use the lyophilized virus is reconstituted in a stabilizing solution, e.g., saline or comprising SPG, Mg++ and HEPES, with or without adjuvant, as further described below. The biologically derived or recombinantly modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, aluminum phosphate, aluminum hydroxide, or alum, which are materials well known in the art. Preferred adjuvants also include Stimulon® QS-21 (Aquila Biopharmaceuticals, Inc., Farmingham, Mass.), MPL® (3-0-deacylated monophosphoryl lipid A; RIBI ImmunoChem Research, Inc., Hamilton, Mont.), and interleukin-12 (Genetics Institute, Cambridge, Mass.).

Upon immunization with a human-bovine chimeric RSV vaccine composition as described herein, via aerosol, droplet, oral, topical or other route, the immune system of the host responds to the vaccine by producing antibodies specific for one or more RSV virus proteins, e.g., F and/or G glycoproteins. As a result of the vaccination the host becomes at least partially or completely immune to RSV infection, or resistant to developing moderate or severe RSV disease, particularly of the lower respiratory tract.

Human-bovine chimeric RSV vaccines of the invention may comprise attenuated chimeric virus that elicits an immune response against a single RSV strain or antigenic subgroup, e.g. A or B, or against multiple RSV strains or subgroups. In this context, the chimeric RSV can elicit a monospecific immune response or a polyspecific immune response against multiple RSV strains or subgroups. Alternatively, chimeric RSV having different immunogenic characteristics can be combined in a vaccine mixture or administered separately in a coordinated treatment protocol to elicit more effective protection against one RSV strain, or against multiple RSV strains or subgroups.

The host to which the vaccine is administered can be any mammal susceptible to infection by RSV or a closely related virus and capable of generating a protective immune response to antigens of the vaccinizing virus. Thus, suitable hosts include humans, non-human primates, bovine, equine, swine, ovine, caprine, lagamorph, rodents, etc. Accordingly, the invention provides methods for creating vaccines for a variety of human and veterinary uses.

The vaccine compositions containing the attenuated human-bovine chimeric RSV of the invention are administered to a patient susceptible to or otherwise at risk of RSV infection in an "immunogenically effective dose" which is sufficient to induce or enhance the individual's immune response capabilities against RSV. In the case of human subjects, the attenuated virus of the invention is administered according to well established human RSV vaccine protocols, as described in, e.g., (Wright et al., *Infect. Immun.* 37:397-400, 1982; Kim et al., *Pediatrics* 52:56-63, 1973; and Wright et al., *J. Pediatr.* 88:931-936, 1976), which are each incorporated herein by reference. Briefly, adults or children are inoculated intranasally via droplet with an immunogenically effective dose of RSV vaccine, typically in a volume of 0.5 ml of a physiologically acceptable diluent or carrier. This has the advantage of simplicity and safety compared to parenteral immunization with a non-replicating vaccine. It also provides direct stimulation of local respiratory tract immunity, which plays a major role in resistance to RSV. Further, this mode of vaccination effectively bypasses the immunosuppressive effects of RSV-specific maternally-derived serum antibodies, which typically are found in the very young. Also, while the parenteral administration of RSV antigens can sometimes be associated with immunopathologic complications, this has never been observed with a live virus.

In all subjects, the precise amount of human-bovine chimeric RSV vaccine administered and the timing and repetition of administration will be determined based on the patient's state of health and weight, the mode of administration, the nature of the formulation, etc. Dosages will generally range from about $10^3$ to about $10^6$ plaque forming units (PFU) or more of virus per patient, more commonly from about $10^4$ to $10^5$ PFU virus per patient. In any event, the vaccine formulations should provide a quantity of attenuated RSV of the invention sufficient to effectively stimulate or induce an anti-RSV immune response, e.g., as can be determined by complement fixation, plaque neutralization, and/or enzyme-linked immunosorbent assay, among other methods. In this regard, individuals are also monitored for signs and symptoms of upper respiratory illness. As with administration to chimpanzees, the attenuated virus of the vaccine grows in the nasopharynx of vaccinees at levels approximately 10-fold or more lower than wild-type virus, or approximately 10-fold or more lower when compared to levels of incompletely attenuated RSV.

In neonates and infants, multiple administration may be required to elicit sufficient levels of immunity. Administration should begin within the first month of life, and at intervals throughout childhood, such as at two months, six months, one year and two years, as necessary to maintain sufficient levels of protection against native (wild-type) RSV infection. Similarly, adults who are particularly susceptible to repeated or serious RSV infection, such as, for example, health care workers, day care workers, family members of young children, the elderly, individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be indicated for administration to different recipient groups. For example, an engineered chimeric RSV strain expressing a cytokine or an additional protein rich in T cell epitopes may be particularly advantageous for adults rather than for infants. RSV vaccines produced in accordance with the present invention can be combined with viruses expressing antigens of another subgroup or strain of RSV to achieve protection against multiple RSV subgroups or strains. Alternatively, the vaccine virus may incorporate protective epitopes of multiple RSV strains or subgroups engineered into one RSV clone as described herein.

Typically when different vaccine viruses are used they will be administered in an admixture simultaneously, but they may also be administered separately. For example, as the F glycoproteins of the two RSV subgroups differ by only about 10% in amino acid sequence, this similarity is the basis for a cross-protective immune response as observed in animals immunized with RSV or F antigen and challenged with a heterologous strain. Thus, immunization with one strain may protect against different strains of the same or different subgroup. However, optimal protection probably will require immunization against both subgroups.

The human-bovine chimeric RSV vaccines of the invention elicit production of an immune response that is protective against serious lower respiratory tract disease, such as pneumonia and bronchiolitis when the individual is subsequently infected with wild-type RSV. While the naturally circulating virus is still capable of causing infection, particularly in the upper respiratory tract, there is a very greatly reduced possibility of rhinitis as a result of the vaccination and possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup.

Preferred human-bovine chimeric RSV of the present invention exhibit a very substantial diminution of virulence when compared to wild-type virus that is circulating naturally in humans. The chimeric virus is sufficiently attenuated so that symptoms of infection will not occur in most immunized individuals. In some instances the attenuated virus may still be capable of dissemination to unvaccinated individuals. However, its virulence is sufficiently abrogated such that severe lower respiratory tract infections in the vaccinated or incidental host do not occur.

The level of attenuation of human-bovine chimeric RSV vaccine virus may be determined by, for example, quantifying the amount of virus present in the respiratory tract of an immunized host and comparing the amount to that produced by wild-type RSV or other attenuated RSV which have been evaluated as candidate vaccine strains. For example, the attenuated chimeric virus of the invention will have a greater degree of restriction of replication in the upper respiratory tract of a highly susceptible host, such as a chimpanzee, compared to the levels of replication of wild-type virus, e.g., 10- to 1000-fold less. Also, the level of replication of the attenuated RSV vaccine strain in the upper respiratory tract of the chimpanzee should be less than that of the RSV A2 ts-1 mutant, which was demonstrated previously to be incompletely attenuated in seronegative human infants. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention must be sufficiently infectious and immunogenic in humans to confer protection in vaccinated individuals. Methods for determining levels of RS virus in the nasopharynx of an infected host are well known in the literature. Specimens are obtained by aspiration or washing out of nasopharyngeal secretions and virus quantified in tissue culture or other by laboratory procedure. See, for example, (Belshe et al., *J. Med. Virology* 1:157-162, 1977; Friedewald et al., *J. Amer. Med. Assoc.* 204:690-694, 1968; Gharpure et al., *J. Virol.* 3:414-421, 1969; and Wright et al., *Arch. Ges. Virusforsch.* 41:238-247, 1973), each incorporated herein by reference. The virus can conveniently be measured in the nasopharynx of host animals, such as chimpanzees.

In some instances it may be desirable to combine the human-bovine chimeric RSV vaccines of the invention with vaccines which induce protective responses to other agents, particularly other childhood viruses. For example, a chimeric RSV vaccine of the present invention can be administered simultaneously with parainfluenza virus vaccine, such as described in Clements et al., *J. Clin. Microbiol.* 29:1175-1182, 1991), which is incorporated herein by reference. In another aspect of the invention the chimeric RSV can be employed as a vector for protective antigens of other respiratory tract pathogens, such as PIV, by incorporating the sequences encoding those protective antigens into the chimeric RSV genome or antigenome which is used to produce infectious chimeric RSV, as described herein.

In yet another aspect of the invention a chimeric RSV is employed as a vector for transient gene therapy of the respiratory tract. According to this embodiment the chimeric RSV genome or antigenome incorporates a sequence which is capable of encoding a gene product of interest. The gene product of interest is under control of the same or a different promoter from that which controls RSV expression. The infectious RSV produced by coexpressing the recombinant RSV genome or antigenome with the N, P, L and M2(ORF1) proteins and containing a sequence encoding the gene product of interest is administered to a patient. This can involve a recombinant RSV which is fully infectious (i.e., competent to infect cultured cells and produce infectious progeny), or can be a recombinant RSV which, for example, lacks one or more of the G, F and SH surface glycoprotein genes and is propagated in cells which provide one or more of these proteins in trans by stable or transient expression. In such a case, the recombinant virus produced would be competent for efficient infection, but would be highly inefficient in producing infectious particles. The lack of expressed cell surface glycoproteins also would reduce the efficiency of the host immune system in eliminating the infected cells. These features would increase the durability and safety of expression of the foreign gene.

With regard to gene therapy, administration is typically by aerosol, nebulizer, or other topical application to the respiratory tract of the patient being treated. Human-bovine chimeric RSV is administered in an amount sufficient to result in the expression of therapeutic or prophylactic levels of the desired gene product. Examples of representative gene products which are administered in this method include those which encode, for example, those particularly suitable for transient expression, e.g., interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

The following examples are provided by way of illustration, not limitation.

Example I

Construction of cDNA Encoding a Chimeric BRSV/HRSV Antigenome and Recovery of Infectious rBRSV/A2 Chimeric Virus Infectious rBRSV can be recovered from cloned cDNAs encoding a viral antigenomic RNA and the N, P, M2-1 and L support proteins (Buchholz et al., *J. Virol.* 73:251-259, 1999), using a strategy similar to that described for HRSV (Collins et al., *Proc. Natl. Acad. Sci. USA* 92:11563-11567, 1995; Bermingham and Collins, *Proc. Natl. Acad. Sci. USA* 96:11259-11264, 1999; Bukreyev et al., *J. Virol.* 70:6634-6641, 1996; Bukreyev et al., *J. Virol.* 71:8973-8982, 1997; Whitehead et al., *J. Virol.* 72:4467-4471, 1998; Whitehead et al., *Virology* 247:232-239, 1998; Collins et al., *Virology* 259:251-255, 1999; Bukreyev et al., *Proc. Natl. Acad. Sci. USA* 96:2367-2372, 1999; Juhasz et al., *Vaccine* 17:1416-1424, 1999; Juhasz et al., *J. Virol.* 73:5176-5180, 1999; Teng and Collins, *J. Virol.* 73:466-473, 1999; Whitehead et al., *J. Virol.* 73:9773-9780, 1999; Whitehead et al., *J. Virol.* 73:871-877, 1999; Whitehead et al., *J. Virol.* 73:3438-3442, 1999; Murphy et al., U.S. Pat. No. 5,993,824; each incorporated herein by reference). However, T7 RNA polymerase was supplied through the use of a cell line that stably expresses this enzyme, rather than by infection with a vaccinia virus recombinant expressing the enzyme (Buchholz et al., *J. Virol.* 73:251-259, 1999).

The cDNA for rBRSV is designed to encode a complete rBRSV antigenomic RNA with authentic 3' and 5' ends without additional heterologous terminal nucleotides. This cDNA encodes infectious rBRSV with in vitro growth properties that are essentially indistinguishable from those of its biological parent, the ATue51908 strain (id.), which is in turn derived from the A51908 strain supplied by the American Type Culture Collection.

Figure 1B:
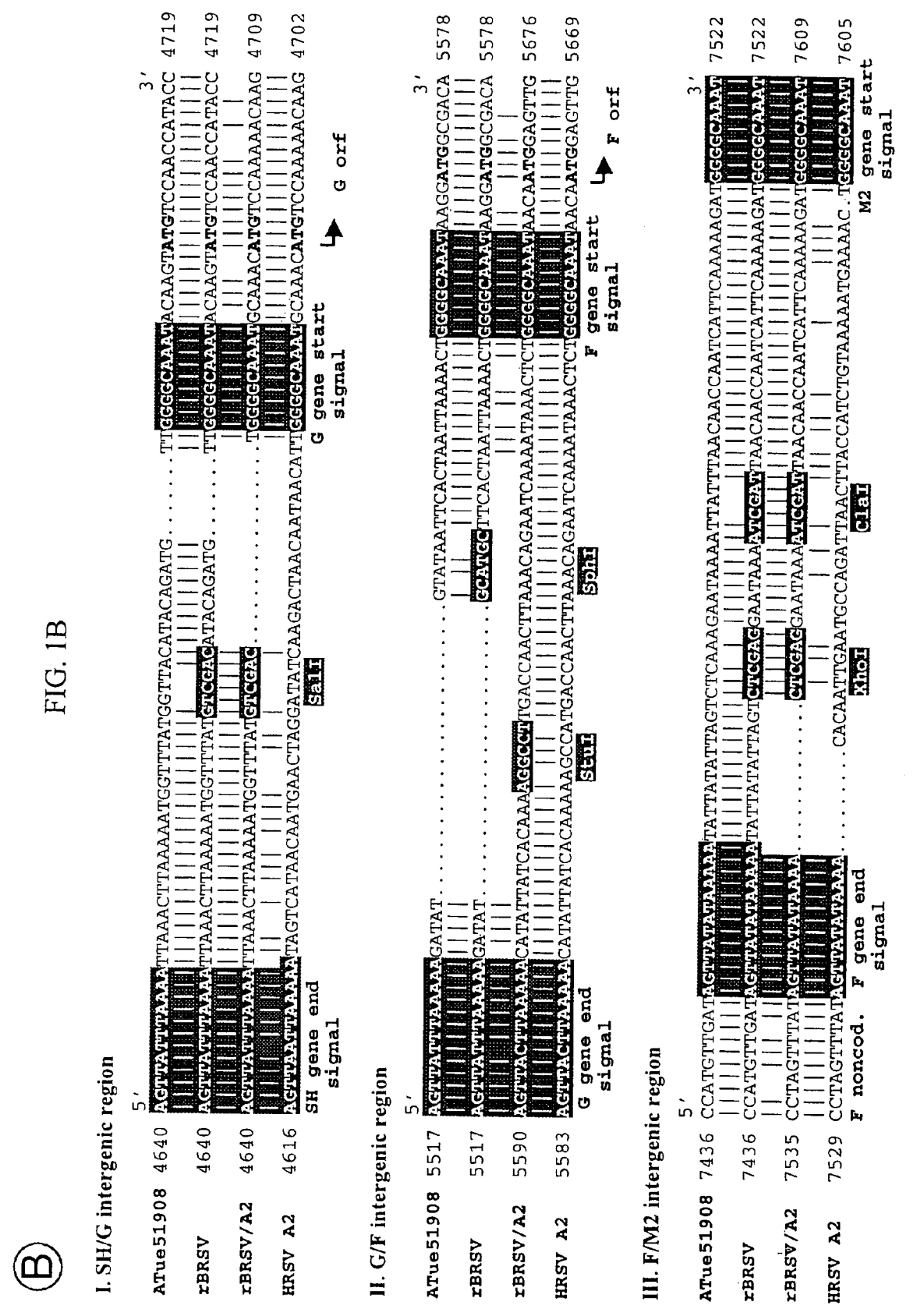

For use within the instant invention, the foregoing plasmid was modified by site-directed mutagenesis according to standard procedures (Kunkel, et al., *Methods Enzymol.* 154:367-382, 1987; incorporated herein by reference) as follows: First, the unique synthetic NotI site in the NS1 noncoding region (Buchholz, et al., *J. Virol.* 73:251-9, 1999, incorporated herein by reference) was removed to yield the ATue51908 wild type sequence (GenBank Accession no. AF 092942). Second, synthetic marker restriction sites were introduced into the SH/G (SalI, ATue51908 nt 4,673), the G/F SphI, ATue51908 nt 5,539) and the F/M2 (XhoI, ATue51908 nt 7,471 and ClaI, ATue51908 nt 7,485) intergenic regions (FIG. 1B). The resulting plasmid was termed pBRSV18 (the Genbank accession number for the BRSV cDNA in pBRSV18 is AF092942). This cDNA served as the parent for constructing BRSV/HRSV chimeras. The rBRSV recovered from this parental cDNA was essentially indistinguishable from the biologically-derived ATue51908 virus in terms of in vitro growth characteristics, and thus is considered to exhibit a wild type growth phenotype.

The G and F genes (nt 4,674 to 7,551) of the previously-reported recombinant version of HRSV strain A2 (U.S. Provisional Patent Application No. 60/007,083, filed Sep. 27, 1995; U.S. patent application Ser. No. 08/720,132, filed Sep. 27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. Pat. No. 5,993,824, issued Nov. 30, 1999; International Publication No. WO 98/02530; Collins, et al., *Proc. Nat. Acad. Sci. USA* 92:11563-11567, 1995; each incorporated herein by reference) were amplified with oligonucleotide primers which introduced a SalI site immediately upstream of the G gene and an XhoI site immediately downstream of the F gene (FIG. 1B). The PCR product was cloned and the sequence of the insert was confirmed in its entirety. Subsequently, these SalI and XhoI restriction sites were used to transfer an approximately 2,885 bp fragment spanning the HRSV G and F genes, including gene start and gene end/polyadenylation signals, into pBRSV18, replacing the respective BRSV genes. The resulting plasmid encoding a chimeric BRSV antigenome with the glycoprotein genes derived from HRSV A2 was termed pBRSV/A2-10. FIG. 1A represents a schematic overview of the genome organization of the recombinant viruses (rBRSV and rBRSV/A2) expressed from pBRSV18 and pBRSV/A2-10. The chimeric antigenome synthesized from the plasmid is 15,227 nt in length, 87 nt longer than that of the parental rBRSV.

Recombinant RSVs were recovered from cDNA essentially as described elsewhere herein and in the above-incorporated references. 32-mm dishes of subconfluent BSR T7/5 cells stably expressing phage T7 RNA polymerase were transfected with of 5 μg of the respective full length plasmids (pBRSV18 or pBRSV/A2-10) and a set of four support plasmids (2.5 g pN, 2.5 μg pP, 0.5 μg, pL, and 0.5 μg pM2) from which the BRSV N, P, L, and M2 proteins are expressed. All cDNA constructs were cloned under control of a T7 promoter. The expression plasmids contained an EMCV IRES sequence, allowing cap-independent translation. Transfections were done using Superfect (Qiagen, Valencia, Calif.) transfection reagent. Two hours after transfection, the supernatant was removed, cells were washed and maintained in minimum essential medium supplemented with 3% fetal calf serum (FCS). Three days after transfection, the cells were split in a 1 to 3 ratio. Cells and supernatant were harvested 7 days after transfection. Duplicate transfections were overlaid with methylcellulose, incubated 5 days without splitting, and examined by immunochemical staining. This showed that PBRSV18 and pBRSV/A2-10 yielded similar levels of recovered virus, approximately 100 foci per 32-mm dish. By this criterion, the rBRSV/A2 virus exhibited essentially the same viability as the rBRSV parent.

To verify the identities of the recovered viruses, viral RNA was recovered from infected cells and analyzed by reverse transcription (RT)PCR. The reactions were performed with primers designed to copy and amplify the three regions of genomic RNA which contained the marker restriction sites shown in FIG. 1B which would distinguish between ATue51908, rBRSV, and rBRSV/A2. The primers used for RT were antigenome sense, complementary to a region of the BRSV (strain ATue51908) M gene (ATue51908 nt 3612 to 3635), to the BRSV G gene (ATue51908 nt 5372 to 5392) or to the HRSV A2 G gene (HRSV A2 nt 5442-5463), and to the BRSV F gene (ATue51908 nt 7218 to 7240) or HRSV A2 F gene (A2 nt 7309 to 7329). An aliquot of the RT product was used for PCR, using the respective first-strand primer noted above and reverse primers, corresponding to the genomic sequences, downstream of the respective intergenic regions (ATue51908 nt 4886 to 4862 and HRSV A2 4878 to 4856, reverse primers downstream of the SH/G intergenic region; ATue51908 nt 5964 to 5941 and HRSV A2 nt 6055 to 6033, reverse primers downstream of the G/F intergenic region, and ATue51908 nt 7852 to 7832, reverse primer downstream of the F/M2 intergenic region).

Figure 2A:
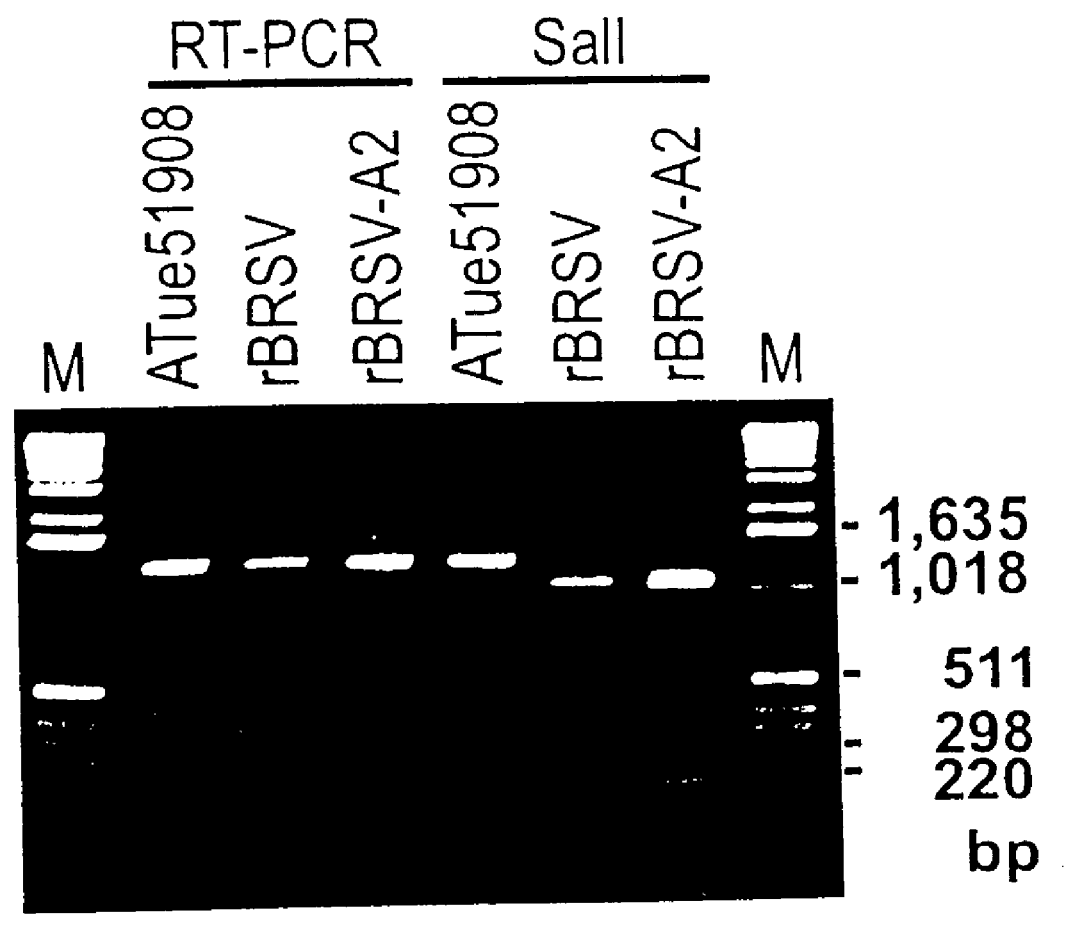
Figure 2B:
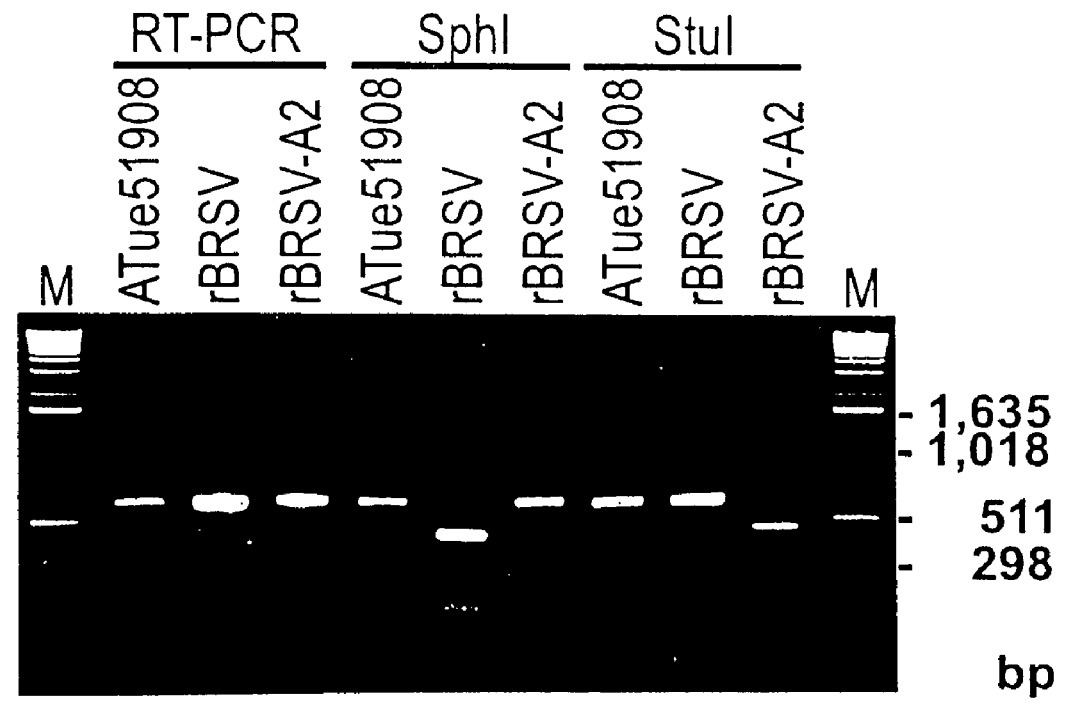
Figure 2C:
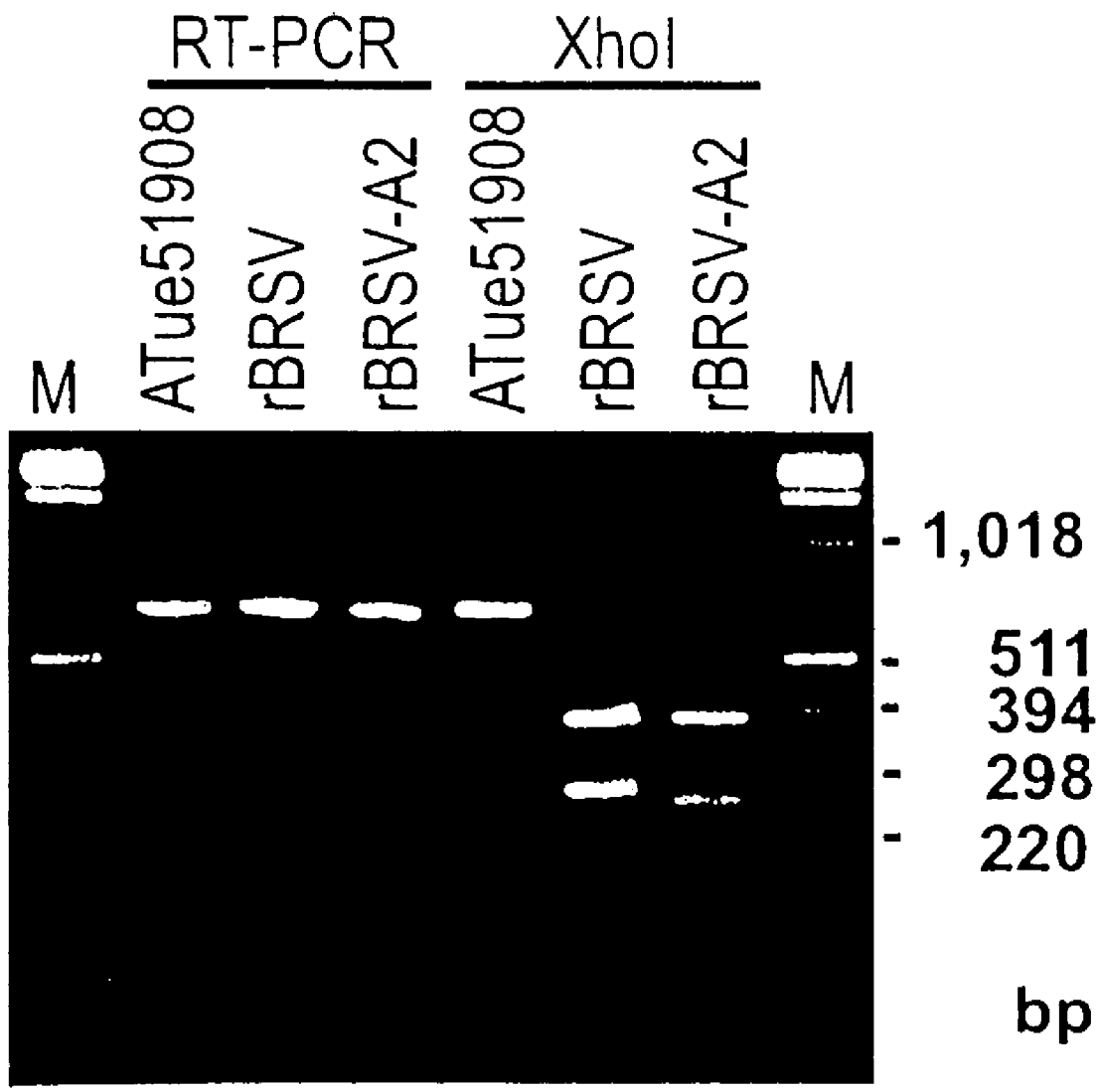

As shown in FIGS. 2A and 2B, the RT-PCR reactions each yielded a single cDNA product whose electrophoretic mobility in each case was consistent with calculated predictions. No PCR product was detected if the RT step was omitted, demonstrating that the product was derived from RNA rather than from contaminating DNA. The RT-PCR products were subjected to digestion with diagnostic restriction enzymes (SalI, StuI, SphI, and XhoI) and analyzed by electrophoresis on an agarose gel. In all cases, the expected restriction pattern was obtained, indicating that each virus contained the expected restriction site markers. Specifically, the ATue51908 biologically-derived virus lacked all four sites within the examined region, both recombinants contained a single SolI located in the SH/G intergenic region and a single XhoI site within the F/M2 region, rBRSV contained a single SphI site within the G/F intergenic region, and rBRSV/A2 contained a single StuI site within this latter region. In addition, the RT-PCR products were sequenced using an automated sequencer (LI-COR, MWG), which confirmed the expected sequences. Thus, the chimeric rBRSV/A2 virus had the expected structure, and there were no sequence changes during recovery.

Example II

In Vitro Analysis of Recombinant Chimeric rBRSV/A2 Virus

To prepare stocks of virus for further analysis, monolayers of bovine MDBK cells were infected with a multiplicity of infection (MOI) of 0.1 with rBRSV or rBRSV/A2. After 90 minutes of adsorption, the inoculum was removed and cells were maintained in minimum essential medium supplemented with 3% fetal bovine serum (FBS). When the cytopathic effect (CPE) was pronounced, typically after 4 to 7 days of incubation, the medium was adjusted to 100 mM $MgSO_4$ and to 50 mM HEPES (pH 7.5) in order to stabilize the virus (Fernie and Gerin, *Virology* 106:141-4, 1980, incorporated herein by reference), and cells and medium were subjected to three rounds of rapid freezing to −70° C. and rapid thawing in order to release virus. Cell debris was removed by centrifugation. Biologically-derived HRSV strain Long was propagated in HEp-2 cells in the same manner. Strain Long is very similar to strain A2 with regard to sequence analysis and reactivity with most monoclonal antibodies, and thus serves as a surrogate for strain A2 in these particular assays (Johnson, et al., *Proc. Nat. Acad. Sci. USA* 84:5625-9, 1987; Johnson and Collins, *J Gen. Virol.* 70:1539-47, 1989; Lopez, et al., *Virus Res.* 10:249-61, 1988, each incorporated herein by reference). The ATue51908 biologically-derived parent was not analyzed in parallel because its in vitro growth properties are substantially the same as its recombinant derivative rBRSV, which therefore was used as the BRSV control. Virus titrations were carried out as described previously (Buchholz, et al., *J. Virol.* 73:251-9, 1999, incorporated herein by reference).

The expression of G protein in human HEp-2 cells by rBRSV, rBRSV/A2 and HRSV strain Long was examined by indirect immunofluorescence. HEp-2 cells were infected with an MOI of 0.1 and, 36 h post infection, were fixed with 80% acetone and incubated at 37° C. for 30 minutes with mouse monoclonal antibody (mab) G66 directed to BRSV G (1:1000 dilution), (Furze, et al., *J. Gen. Virol.* 75:363-70, 1994; Langedijk, et al., *J. Virol.* 71:4055-61, 1997, each incorporated herein by reference), or mab 021/01G directed against HRSV G (1:40 dilution), (Garcia-Barreno, et al., *J. Virol.* 63:925-32, 1989; Martinez and Melero, *J. Gen. Virol.* 79:2215-20, 1998, each incorporated herein by reference). Cells were stained with a fluorescein isothiocyanate conjugated goat anti-mouse IgG (Dianova, Hamburg) and counterstained with 0.01% Evans Blue.

As expected, the BRSV-specific mab reacted with rBRSV but not with rBRSV/A2 or HRSV (Table 1). In contrast, the HRSV-specific mab reacted with rBRSV/A2 and HRSV, but not with rBRSV. The patterns of reactivity of rBRSV and HRSV were consistent with their bovine and human specificities, respectively, and the pattern of reactivity of rBRSV/A2 confirmed that it expressed a G protein of human rather than bovine origin. On the other hand, the chimeric rBRSV/A2 virus induced cytopathic effect (CPE) in HEp-2 cells which was more similar to that of rBRSV than HRSV. For example, in cultures infected with HRSV, nearly 100% of the cells showed positive immunofluorescence, compared to 20% infected with rBRSV and 20-30% infected with rBRSV/A2. In addition, HRSV induced pronounced CPE with the formation of large syncytia, whereas rBRSV and rBRSV/A2 caused a reduced level of CPE and the formation of smaller syncytia. Thus, the infectivity and CPE of the chimeric rBRSV/A2 virus in this human cell line more closely resembles that of its rBRSV parent. This indicates that transfer of the surface glycoproteins G and F alone to rBRSV does not confer full permissivity of HRSV for growth in human cells—suggesting that additional HRSV genes help determine growth characteristics in HEp-2 cells.

TABLE 1

Confirmation by reactivity with monoclonal antibodies[a] of the presence of the appropriate F and G glycoproteins in the rBRSV/A2 and rBRSV/LongF recombinant viruses.

| mab | specificity | rBRSV[a] | rBRSV/A2[a] | rBRSV/LongF[a] | HRSV[a] |
|---|---|---|---|---|---|
| G66 | BRSV G | + | − | + | − |
| 021/1G | HRSV G | − | + | − | + |
| 2F | RSV F | + | + | + | + |
| 44F | HRSV F | − | + | + | + |

[a]Reactivity in indirect immunofluorescence assay and immunoelectron microscopy.

Figure 3:
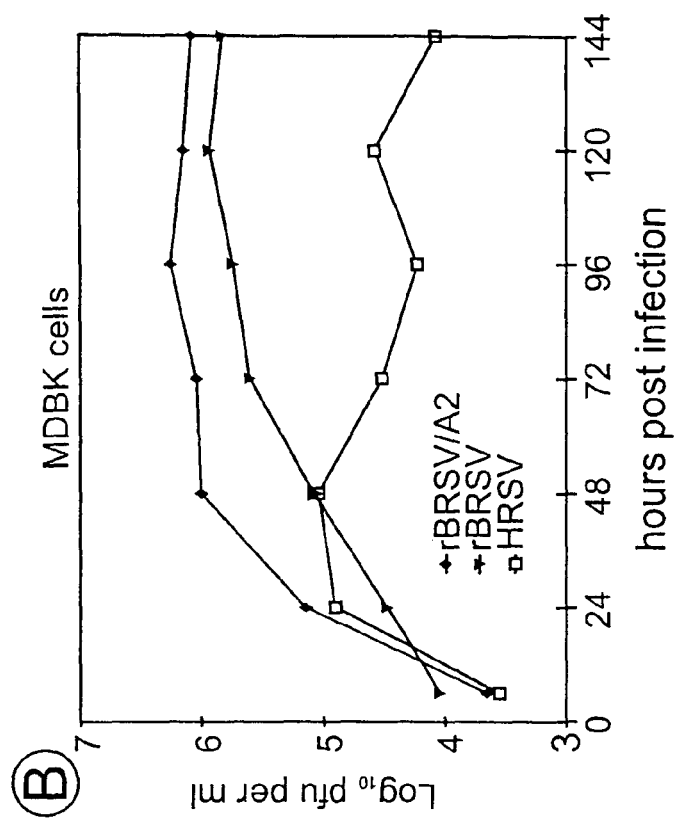
FIG. 3 shows a comparison of the growth of rBRSV, rBRSV/A2 and HRSV strain Long in human HEp-2 cells (Panel A) and bovine MDBK cells (Panel B). Duplicate cell monolayers in 24-well dishes were infected with an MOI of 0.1 of either virus. Supernatant aliquots were taken at the indicated times, frozen at −70° C. and titrated later in duplicate. Each value is the mean titer of material from two wells of infected cells.
Figure 3:
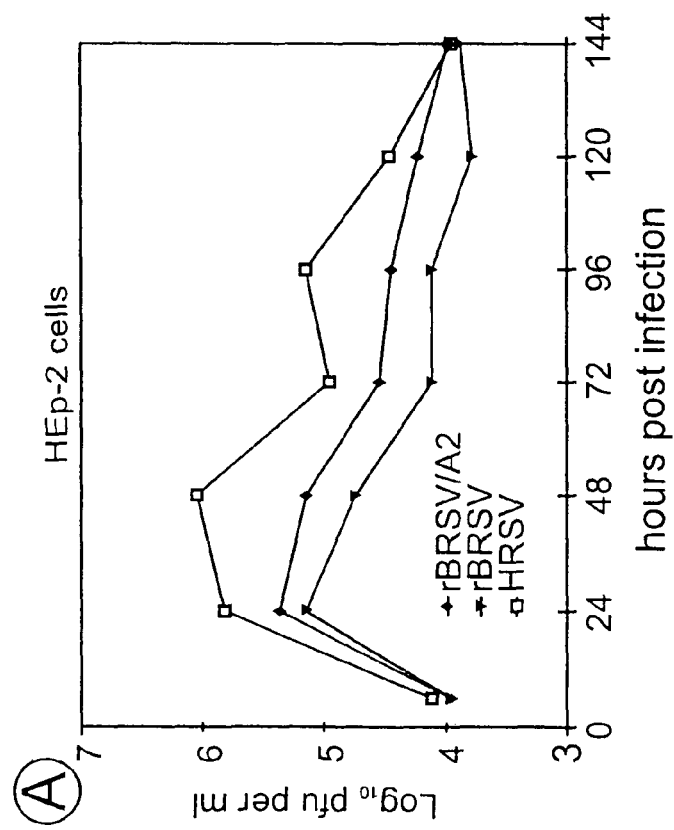

Multicycle growth of rBRSV, rBRSV/A2, and HRSV strain Long was compared in MDBK and HEp-2 cells (FIG. 3). Equal numbers of subconfluent MDBK cells and HEp-2 cells in 24-well dishes were infected with virus at an MOI of 0.1. After 90 minutes adsorption, the inoculum was removed and the cells were washed twice with medium containing 3% FBS. At various times after infection, duplicate wells were harvested, the medium was adjusted to 100 mM MgSO$_4$ and 50 mM HEPES (pH 7.5), and the cells and medium were quickly frozen and thawed three times. The medium was clarified by centrifugation and the virus was titrated. In HEp-2 cells, HRSV produced approximately 10-fold more virus than rBRSV (FIG. 3, Panel A), whereas in MDBK cells the situation was reversed (FIG. 3, Panel B). In MDBK cells, HRSV reached a maximum titer after 2 days, whereas rBRSV continued to grow and reached a maximum after 4 to 5 days. These results are consistent with partial restriction of growth for HRSV in this bovine cell line. Interestingly, the chimeric rBRSV/A2 replicated better than rBRSV by approximately 2-fold in both the human and bovine cell lines, and in the bovine cells its growth curve resembled that of rBRSV rather than HRSV. These results indicate that the growth characteristics of the chimeric virus were not identical to either parent, consistent with its chimeric nature. The ability to replicate efficiently in this multi-cycle growth experiment indicates that the HRSV G and F proteins are functional in the rBRSV background. Most importantly, these results indicate that the chimeric virus is fully competent for growth in two cell lines, one of human origin and one of bovine.

Immunoelectron microscopy was employed to examine virions for the presence of G protein of the appropriate specificity. MDBK cells were infected with an MOI of 0.1 of rBRSV, rBRSV/A2, or HRSV. At 72 hours post infection, when CPE was pronounced, the material was fixed with buffered 0.05% glutaraldehyde for 15 min to stabilize the virion structure. The monolayer was scraped off the plate and after low speed centrifugation, the pellet was resuspended in a small amount of buffer. Glow discharged formvar coated 300 mesh copper grids, stabilized with carbon, were floated on drops of cell suspension. Nonspecific adsorption of antibodies was blocked by treating the grids with 1% cold water fish gelatin (Sigma, Deisenhofen, Germany) in standard phosphate buffered saline (PBS) containing 1% bovine serum albumin (PBS-BSA). Subsequently, the grids were floated for 45 min on drops of monoclonal antibodies (2F, specific to HRSV and BRSV F, 44F, specific to HRSV F, 021/1G, specific to HRSV G, and 66G, specific to BRSV G (Garcia-Barreno et al., *J. Virol.* 63:925-932, 1989; Martinez et al., *J. Gen. Virol.* 79:2215-2220, 1998)), diluted in PBS-BSA. After several washings in PBS-BSA, bound antibodies were detected with colloidal gold (10 nm) labeled goat anti-mouse immunoglobulin Fab (GAF10, BioCell Int., Cardiff, United Kingdom) and negatively stained with phosphotungstic acid (PTA), pH 6.0. The grids were examined using a 400 T transmission electron microscope (Philips, The Netherlands). This process leaves virion structure intact and allows detection of external surface antigens.

Figure 4:
FIG. 4 provides an electron microscopic examination of virions of recombinant BRSV after fixation with glutardaldehyde, followed by immunogold labeling and negative staining (overview and enlargement) (Panel A), compared to virions detected in ultra thin sections (Panel B). The long filamentous virion shape as well as the antigenic epitopes on the virion surface are conserved by the preparation technique. (Panel A bar: 2µ, enlargement: bar: 100 nm, Panel B bar: 150 nm.
Figure 4:
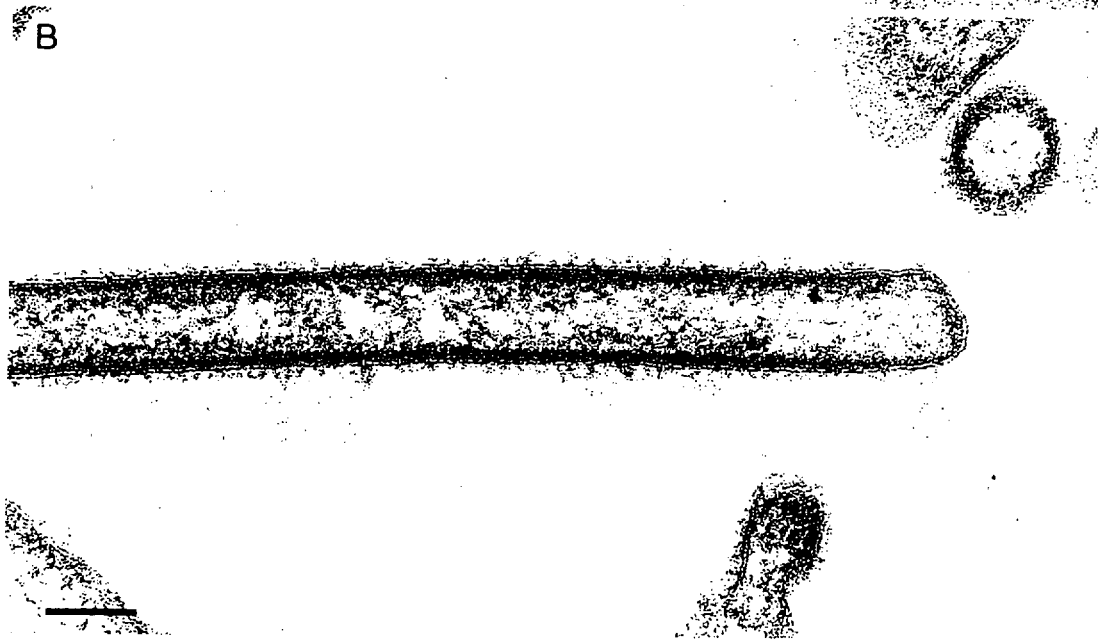

Electron microscope analyses revealed large amounts of filamentous particles with a diameter of 100 to 200 nm and of several μm in length in preparations of rBRSV (FIG. 4, Panel A), rBRSV/A2, and HRSV strain Long. Comparison of material after ultrathin section and after glutardialdehyde fixation proved that the shape of the virions was maintained after glutardialdehyde fixation. Variations in the virion diameter that are observed after glutaraldehyde fixation might be due to dehydration of the particles during the fixation procedure (FIG. 4, Panels A and B). Furthermore, the antigenic structure and reactivity of monoclonal antibodies was unaffected (FIG. 4, Panel A, insert).

Figure 5:
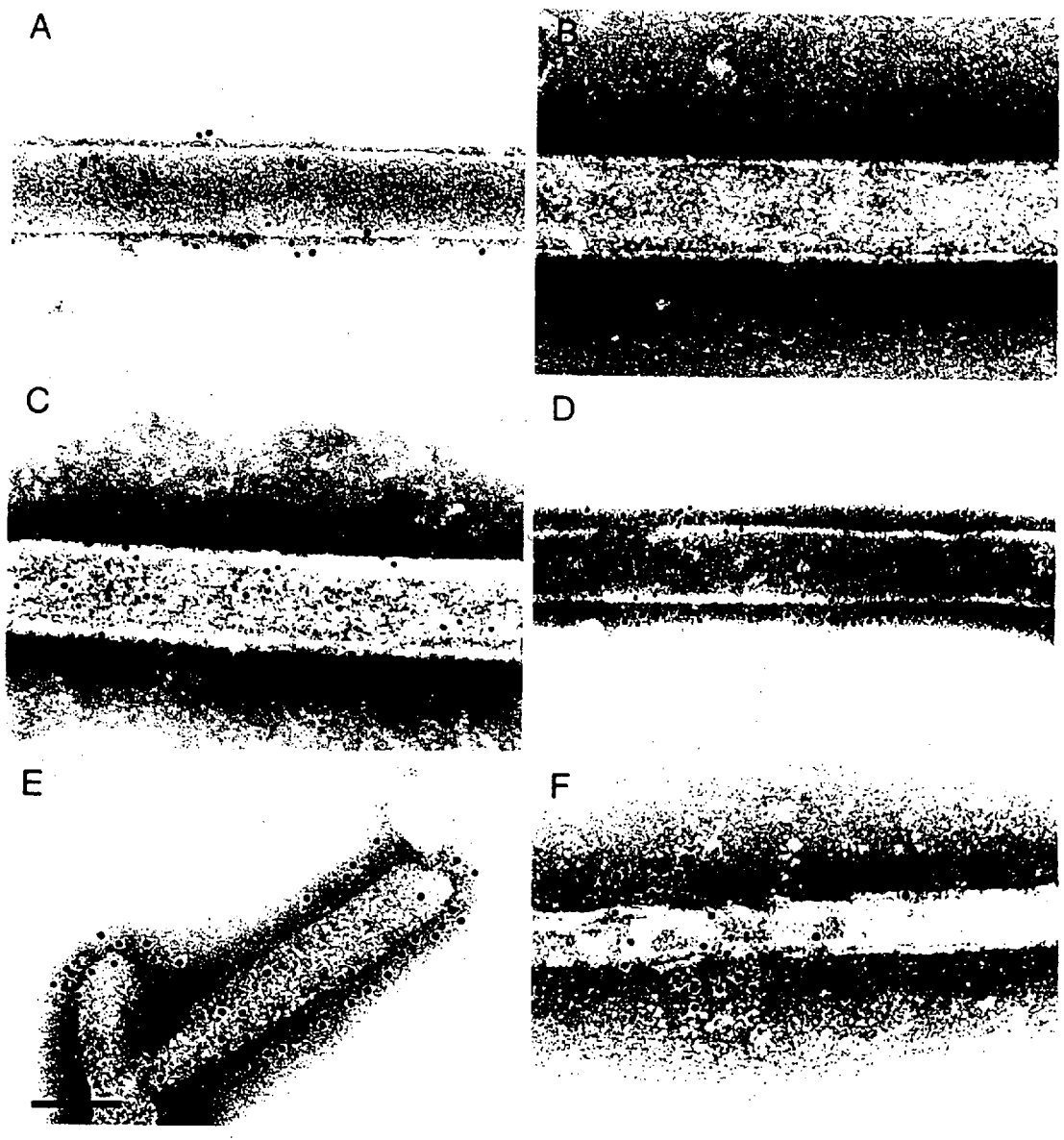
FIG. 5 shows immunogold labeling using monoclonal antibodies reacting with both HRSV F and BRSV F protein (Panels A, C and E) or exclusively with HRSV F protein (Panels B, D and F). Labeling of preparations of rBRSV (Panels A and B), rBRSV/A2 (Panels C and D), and of HRSV, strain Long (Panels E and F). Bar: 150 nm.

The virus preparations were subjected to immunoelectron microscopy using the set of antibodies directed to BRSV and HRSV G and F proteins (Table 1), followed by labeling with gold-conjugated goat anti-mouse immunoglobulin, and negatively stained. Using a monoclonal antibody directed to HRSV F (FIG. 5, Panels B, D and F), a dense immunogold labeling of the rBRSV/A2 virion surface could be observed (FIG. 5, Panel D), comparable to the labeling intensity of the HRSV virion surface (FIG. 5, Panel F), whereas no specific labeling of rBRSV virions was detected (FIG. 5, Panel B). Antibody 2F, reacting with both BRSV and HRSV F protein (FIG. 5, Panels A, C and E), was used as control to demonstrate the intact antigenic structure of all virus preparations, including the BRSV preparation. This confirmed that the rBRSV/A2 chimeric virus and HRSV positive control virus contained the HRSV F protein, whereas the rBRSV negative control virus did not, as expected.

Figure 6:
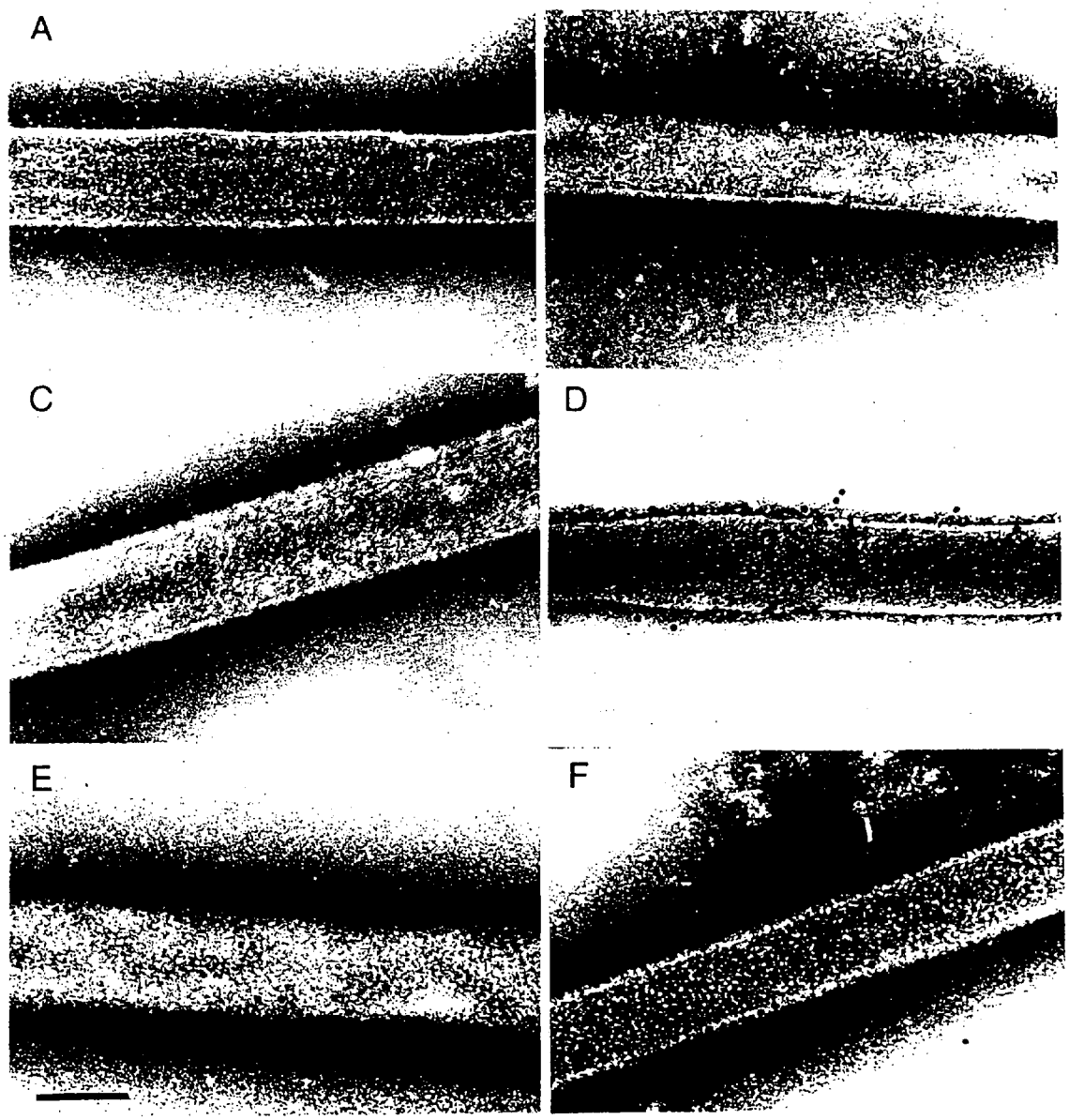
FIG. 6 shows immunogold labeling using monoclonal antibodies reacting with BRSV G protein (Panels A, C and E) or with HRSV G protein (Panels B, D and F). Labeling of preparations of rBRSV (Panels A and B), rBRSV/A2 (Panels C and D), and of HRSV strain Long (Panels E, F). Bar: 150 nm.

A monoclonal antibody directed to HRSV G protein reacted with rBRSV/A2 (FIG. 6, Panel D), as well as with HRSV particles (FIG. 6, Panel F), and failed to react with the rBRSV virion surface (FIG. 6, Panel B). When using an antibody directed to BRSV G as a control, only the rBRSV virion surface was immunogold labeled (FIG. 6, Panel A), but not the virion surface of the chimeric virions (rBRSV/A2, FIG. 6, Panel C) or of HRSV (FIG. 6, Panel E). These results confirmed that the rBRSV/A2 chimeric virus and HRSV control virus contained the HRSV G protein and not that of BRSV, whereas the rBRSV control virus contained the BRSV G protein and not that of HRSV. Thus, the rBRSV/A2 chimeric virus indeed bore the HRSV G and F proteins as surface glycoproteins, and present in amounts comparable to that of biologically-derived virus.

Example III

Figure 7A:
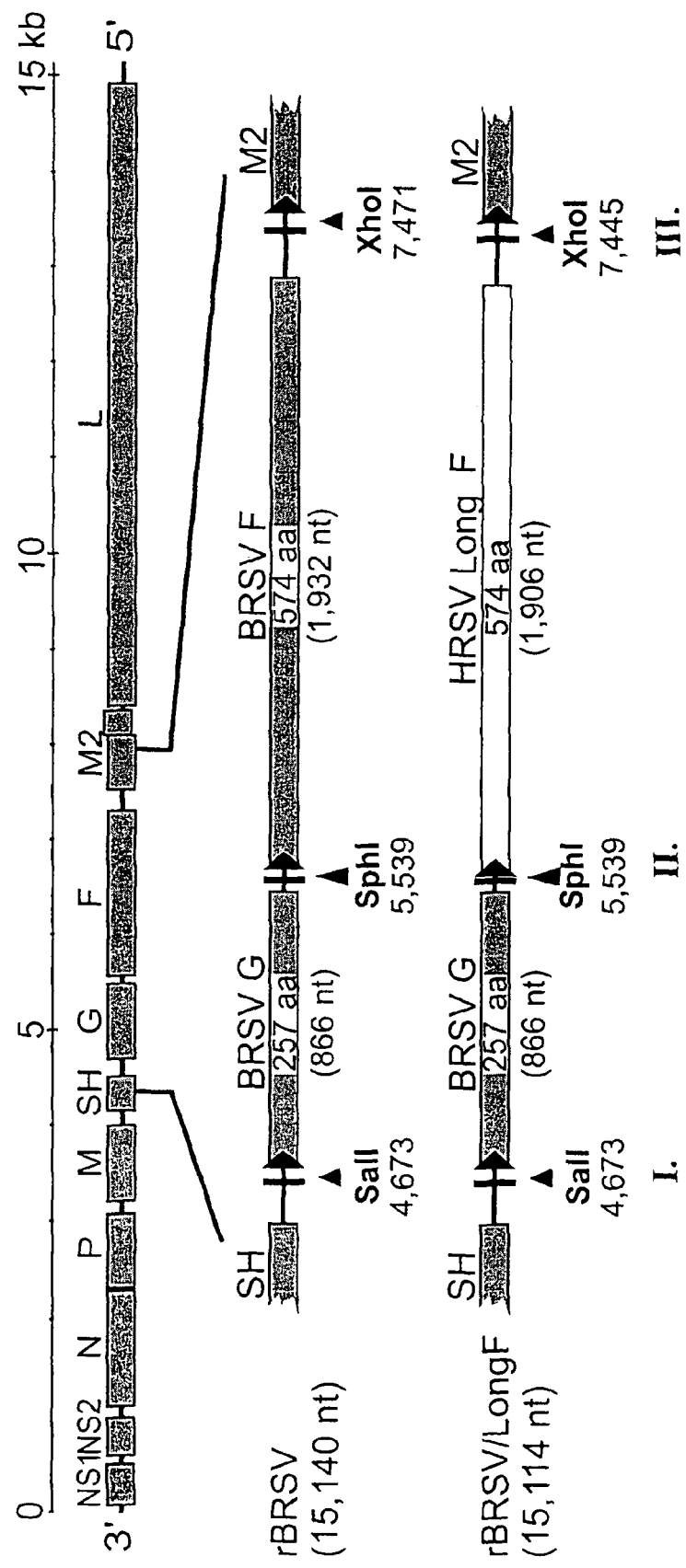

Construction of cDNA Encoding a Chimeric BRSV/HRSV Virus Containing a Single Gene Replacement Involving a Different HRSV Subgroup A Virus The chimeric rBRSV/A2 virus described above involved the simultaneous substitution of two surface glycoproteins, G and F. It was of interest to determine whether a BRSV/HRSV chimeric virus could be made in which the substitution involved only one of the two glycoproteins, and whether the substitution could be made with a different subgroup A strain, namely the Long strain. A second BRSV antigenome cDNA was constructed which contains the HRSV strain Long F gene in place of the BRSV F gene (FIGS. 7A and 7B). Total RNA was made from HEp-2 cells infected with HRSV strain Long. Subsequently, RT-PCR was performed using primers FLa (5'-AG GAATTCGCATGCGGGGCAAATAACAATGGAGTTGCCAATC-3' (SEQ ID NO.: 21), nt 1 to 28 of the HRSV strain Long F gene sequence, containing an EcoRI/SphI adapter, underlined) and FLRa (5'-AG GAATTCTCGAGTTTTTATATAACTATAAACTAGGAATCTAC-3' (SEQ ID NO.: 22), HRSV strain Long F gene nt 1903 to 1874, EcoRI/XhoI adapter underlined), yielding a PCR product of 1,930 bp. The EcoRI adapters were used to clone the PCR product into pBluescript SK—(Stratagene, La Jolla, Calif.). The PCR product was sequenced, and a 1,906 bp fragment was excised with SphI and XhoI and transferred into the SphI-XhoI window of PBRSV18, yielding pBRSV/LongF-12. This encodes a chimeric RSV antigenome of 15,114 nt.

Plasmid pBRSV/LongF-12 was transfected onto BSR T7/5 cells stably expressing T7 RNA polymerase, as described above. Five days after transfection, a cytopathic effect of rounding cells typical for RSV could be observed in all transfected dishes. The recovery rates of rBRSV, rBRSV/A2 and rBRSV/LongF were comparably high, typically yielding about 100 foci per 32-mm dish. Virus stocks were produced by two passages of the supernatants from transfections on MDBK cells.

Figure 8:
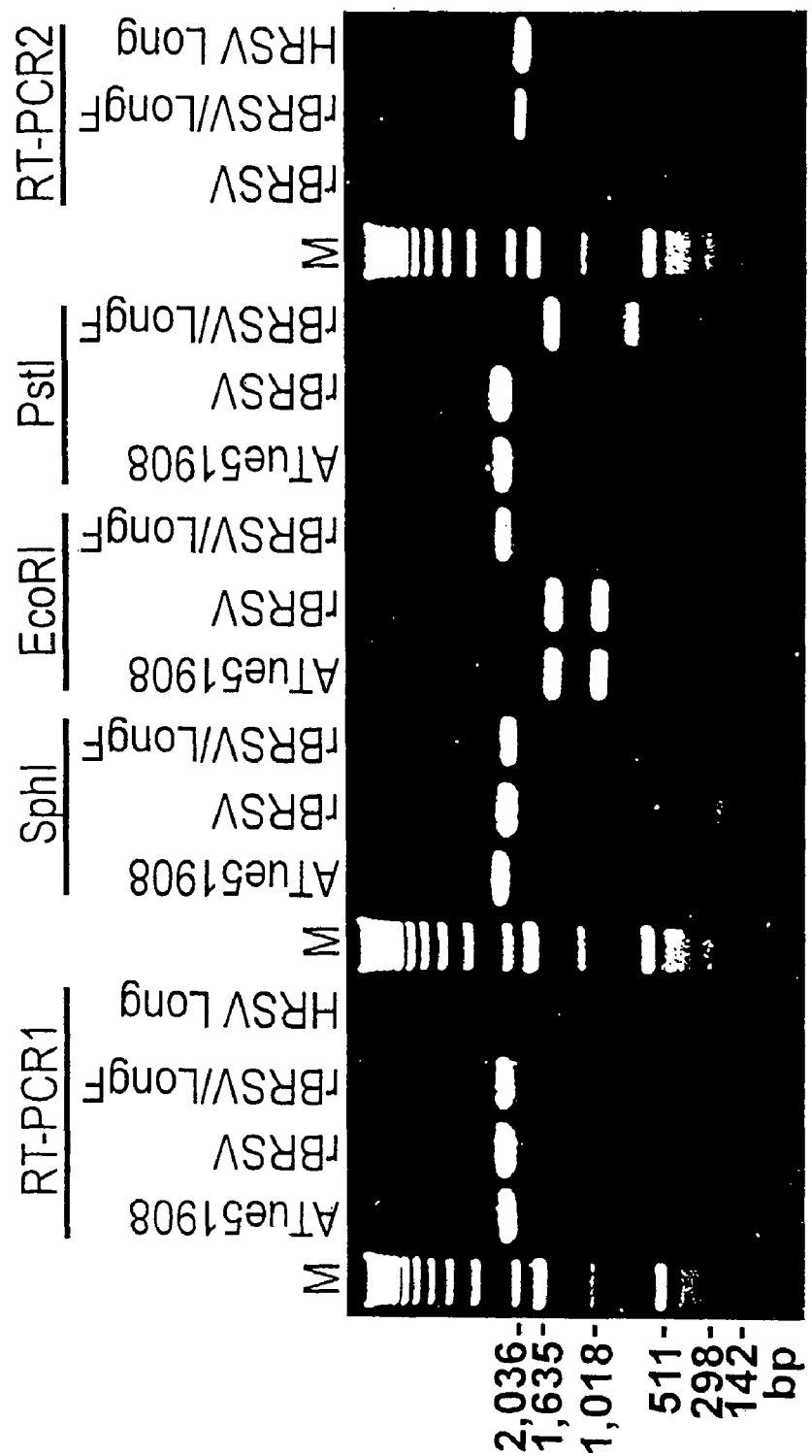
FIG. 8 provides RT-PCR and restriction analysis confirming the identity of the recombinant virus isolate rBRSV/LongF. Two RT-PCRs were done using total RNA from cells infected with indicated virus isolates. The PCR products were analyzed on a 0.8% agarose gel. No PCR product was obtained if the RT step was omitted. Nucleotide lengths are estimates based on calculated sizes. M, 1 kb DNA ladder (Life Technologies, Gaithersburg, Md.). The size of some marker fragments is indicated on the left. PCR 1 was done using a primer pair hybridizing with sequences of the BRSV backbone (ATue51908 nt 5380-5397 (BRSV G gene), and ATue51908 nt 7567-7550 (BRSV M2 gene), upstream and downstream of the F gene. PCR 1 yielded products of 2,187 nt for BRSV strain ATue51908 and the recombinant analog rBRSV, and 2,161 nt for rBRSV/LongF (these bands are not distinguishable by electrophoretic mobility under these conditions). As expected, no PCR product was obtained from HRSV strain Long RNA using the above BRSV primer pair. The products from PCR 1 were subjected to restriction analysis. As predicted, the recombinant viruses, but not standard BRSV strain ATue51908, was cleaved by SphI (yielding bands of 2,028 bp and 159 bp for rBRSV, and 2,002 bp and 159 bp for rBRSV/LongF), demonstrating the existence of the synthetic SphI marker restriction site (rBRSV and rBRSV/LongF genome pos. 5539). EcoRI cleaves at the naturally occurring EcoRI site of the BRSV ATue51908 and the rBRSV F gene (genome pos. 6233) to yield two fragments of 1,334 nt and 853 nt, whereas the fragment originating from rBRSV/LongF is not cleaved by EcoRI, as predicted. When digested by PstI, as expected, the fragments comprising the BRSV F gene remain uncleaved, and the rBRSV/LongF product is cleaved into three fragments of 1,351 bp, 586 bp, and 224 bp, revealing the existence of two naturally occurring PstI sites (pos. 63 and 649) contained in the HRSV Long F gene. PCR 2 was done using a primer pair hybridizing to the HRSV strain Long F gene (primer FL, 3'-GGGGCAAATAA-CAATGGAGTTGCCAATC-5' (SEQ ID NO. 19), nt 1-28 of the HRSV strain Long F gene sequence, and primer FLr, 5'-TTTTTATATAACTATAAACTAGGAATCTAC-3' (SEQ ID NO.: 20), HRSV strain Long F gene nt 1903-1874), yielding a PCR product of 1,903 bp for rBRSV/LongF and the HRSV strain Long parental virus. As expected, no product was obtained from rBRSV. Digestion with EcoRI and PstI yielded the expected cleavage pattern.

To test the identity of recombinant BRSV containing the HRSV strain Long F gene in place of the BRSV F gene sequence, two RT-PCRs were done (FIG. 8). A first RT-PCR (FIG. 8, PCR1) was done using a primer pair hybridizing with sequences of the BRSV backbone, upstream and downstream of the F gene, yielding products of 2,187 nt for BRSV strain ATue51908 and the recombinant analogue rBRSV, and 2,161 nt for rBRSV/LongF. As expected, no PCR product was obtained from HRSV strain Long RNA using the above BRSV primer pair. When subjected to restriction analysis, the recombinant viruses, but not standard BRSV strain ATue51908, were cleaved by SphI (bands of 2,028 bp and 159 bp for rBRSV, and 2,002 bp and 159 bp for rBRSV/LongF), confirming the presence of the synthetic SphI marker restriction site (rBRSV and rBRSV/LongF pos. 5539). EcoRI cleaves at the naturally occurring EcoRI site of the BRSV ATue51908 and the rBRSV F gene (genome pos. 6233) to yield two fragments of 1,334 nt and 853 nt, whereas the fragment originating from rBRSV/LongF was not cleaved by EcoRI, as predicted. When digested by PstI, the fragments comprising the BRSV F gene remained uncleaved, whereas the rBRSV/LongF product was cleaved into three fragments of 1,351 bp, 586 bp, and 224 bp, confirming the presence of two naturally occurring PstI sites (pos. 63 and 649) contained in the HRSV Long F gene sequence (note that the Long sequence is indicated with regard to the individual gene because a complete genome sequence is not available). A second RT-PCR (FIG. 8, PCR2) was done using a primer pair hybridizing to the HRSV strain Long F gene, yielding a PCR product of 1,903 bp for rBRSV/LongF and the HRSV strain Long parental virus. As expected, no product was obtained from rBRSV. Digestion with PstI and EcoRI yielded the expected cleavage patterns (not shown). In addition, RT-PCR products were sequenced using an automated sequencer (LI-COR, MWG), which confirmed the expected sequences. Thus, the chimeric recombinant rBRSV/LongF virus had the expected structure, and there were no sequence changes during recovery and passage.

Figure 9:
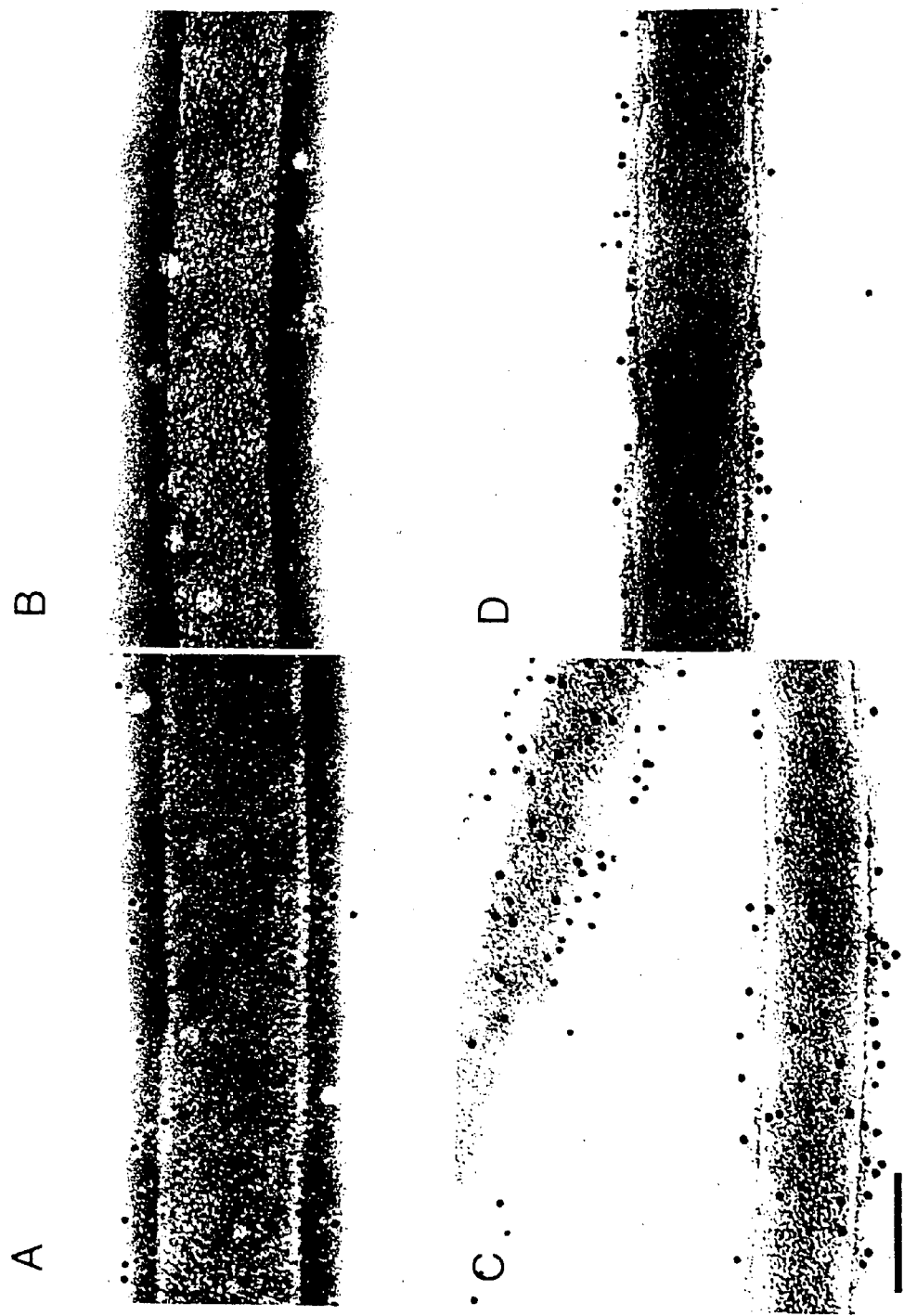
FIG. 9 provides an immunoelectron microscopic analysis of the surface proteins of rBRSV/LongF. Panel A: mab G66 to BRSV G protein; Panel B: mab 021/21G to HRSV G protein; Panel C: mab 2F, reactive with F proteins of both HRSV and BRSV; and Panel D: mab 44F, specific for HRSV F protein. bar: 150 nm.

The rBRSV/LongF chimeric virus was analyzed by immunoelectron microscopy as described above for the rBRSV/A2 virus. Analysis of rBRSV/LongF with mab G66, which is specific for the BRSV G protein, demonstrated strong reactivity (FIG. 9, Panel A), whereas this was not observed with mab 021/21G, specific for the HRSV G protein (FIG. 9, Panel B). There also was strong reactivity or rBRSV/LongF with mab 44F, specific for HRSV F (FIG. 9, Panel D), as well as with mab 2F, which is specific for HRSV and BRSV F proteins (FIG. 9, Panel C). This showed that this chimeric virus contained the parental BRSV G protein together with the heterologous F glycoprotein from HRSV strain Long.

Example IV

Growth of the rBRSV/A2 Chimeric Virus in Seronegative Juvenile Chimpanzees

Young chimpanzees which were determined to be seronegative for HRSV were inoculated by both the intranasal and intratracheal routes with a dose of $10^7$ pfu per ml of rBRSV or rBRSV/A2 at each site (Table 2). Each virus was administered to two chimpanzees. Following inoculation of the virus, nasopharyngeal swab samples were taken daily on days 1-10 and 12, and tracheal lavage samples were taken on days 2, 5, 6, 8 and 12. Specimens were frozen and RSV titers were measured later by plaque assay on HEp-2 cells. The amount of rhinorrhea, a measure of upper respiratory tract illness, was estimated daily and assigned a score of 0-4 (0=none, 1=trace, 2=mild, 3=moderate, 4=severe). The results were compared to historic controls of animals which had received (i) $10^4$ pfu of recombinant HRSV strain A2 wild type virus per site (Whitehead, et al., *J. Virol.* 72:4467-4471, 1998, incorporated herein by reference) or (ii) $10^5$ pfu of the live-attenuated rA2cp28/404 strain A2 vaccine candidate per site (Whitehead, et al., *J. Virol.* 73:3438-3442, 1999, incorporated herein by reference), administered by the same routes (Table 2).

lower respiratory tract. That the shedding was not detected until day 3 or 5 indicates that it was not carryover from the inoculation, as does the length of time over which virus was recovered. The titers were much lower than observed for wild type HRSV and moderately lower than observed for the rA2cp248/404 vaccine candidate. These results indicate that the chimeric virus is highly attenuated. Thus, replacement of the G and F glycoprotein genes of rBRSV with their HRSV

TABLE 2

Replication of recombinant rBRSV and chimeric rBRSV/A2
in the upper and lower respiratory tract of chimpanzees

| Identification | | Nasopharyngeal swab titer ($\log_{10}$pfu/ml) Day post-inoculation | | | | | | | | | | | |
|---|---|---|---|---|---|---|---|---|---|---|---|---|---|
| No. Chimpanzee | Virus | 1 | 2 | 3 | 4 | 5 | 6 | 7 | 8 | 9 | 10 | 12 | Peak |
| 95A016 | rBRSV[a] | <0.7 | <0.7 | <0.7 | <0.7 | <0.7 | <0.7 | <0.7 | <0.7 | <0.7 | <0.7 | <0.7 | <0.7 |
| 95A018 | rBRSV[a] | <0.7 | <0.7 | <0.7 | <0.7 | <0.7 | <0.7 | <0.7 | <0.7 | <0.7 | <0.7 | <0.7 | <0.7 |
| | mean | | | | | | | | | | | | <0.7 |
| 95A007 | rBRSV/A2 | <0.7 | <0.7 | 0.7 | 0.7 | 1.0 | <0.7 | <0.7 | <0.7 | <0.7 | <0.7 | <0.7 | 1.0 |
| 95A008 | rBRSV/A2 | <0.7 | <0.7 | 0.7 | <0.7 | 1.4 | 0.7 | <0.7 | <0.7 | 0.7 | 1.2 | <0.7 | 1.4 |
| | mean | | | | | | | | | | | | 1.2 |
| | rA2cp248/404[b] mean | <0.7 | <0.7 | 1.1 | 2.2 | 1.5 | 2.0 | 1.4 | 1.4 | 1.0 | 0.7 | <0.7 | 2.5[d] |
| | rA2[c] mean | <0.7 | 1.7 | 2.6 | 4.5 | 4.4 | 4.4 | 4.4 | 4.4 | 1.6 | <0.7 | <0.7 | 4.9[d] |

| Identification | | Tracheal lavage titer ($\log_{10}$pfu/ml) Day post-inoculation | | | | | | Peak rhinorrhea |
|---|---|---|---|---|---|---|---|---|
| No. Chimpanzee | Virus | 2 | 5 | 6 | 8 | 12 | Peak | score |
| 95A016 | rBRSV[a] | <0.7 | <0.7 | <0.7 | <0.7 | <0.7 | <0.7 | 0 |
| 95A018 | rBRSV[a] | <0.7 | <0.7 | <0.7 | <0.7 | <0.7 | <0.7 | 0 |
| | mean | | | | | | <0.7 | 0.0 |
| 95A007 | rBRSV/A2 | <0.7 | 0.7 | 1.2 | <0.7 | <0.7 | 1.2 | 0 |
| 95A008 | rBRSV/A2 | <0.7 | 0.7 | 2.0 | <0.7 | <0.7 | 2.0 | 0 |
| | mean | | | | | | 1.6 | 0.0 |
| | rA2cp248/404[b] mean | <0.7 | 1.0 | 1.0 | <0.7 | <0.7 | 1.4[d] | 0.8 |
| | rA2[c] mean | 2.0 | 4.2 | 3.3 | 2.2 | <0.7 | 4.7[d] | 2.5 |

[a]Each virus was administered at a dose of $10^7$ pfu/ml in a 1.0 ml inoculum per site intranasally and intratracheally. Nasopharyngeal swab samples were collected on days 1-10 and 12 and tracheal lavage samples were collected on days 2, 5, 6, 8 and 12.
[b]Virus rA2cp248/404 was evaluated in 4 chimpanzees at a dose of $10^5$ pfu/ml. (Whitehead, et al., J. Virol. 73: 3438-3442, 1999).
[c]Virus rA2 (rA2sites) was evaluated in 4 chimpanzees at a dose of $10^4$ pfu/ml. (Whitehead, et al., J. Virol. 72: 4467-4471, 1998).
[d]Mean peak titers are calculated using the peak virus titer achieved in each animal. Because peak virus titers were achieved on different days for each animal, the mean peak titer exceeds that of the mean titer on any given day.

Wild type HRSV is highly permissive in seronegative chimpanzees, and in this exercise replicated to peak mean titers of more than 4.5 $\log_{10}$ pfu per ml of nasal swab or tracheal lavage sample (Table 2). The peak rhinorrhea score was 2.5. The live-attenuated vaccine candidate rA2cp248/404 (see, e.g., U.S. Pat. No. 5,993,824, issued Nov. 30, 1999; International Publication No. WO 98/02530; Collins, et al., *Proc Natl. Acad. Sci. USA* 92:11563-11567, 1995; Whitehead, et al., *Virology* 247:232-239, 1998, each incorporated herein by reference) replicated to mean peak titers of 2.5 and 1.4 $\log_{10}$ pfu per ml of swab/lavage in the upper and lower respiratory tracts, respectively, and had a peak rhinorrhea score of 0.8. In contrast, there was no detectable replication of rBRSV in either the upper or lower respiratory tracts and no evidence of disease. Thus, even when administered at 100-1000 times the dose of HRSV, rBRSV was highly restricted for replication in chimpanzees. The rBRSV/A2 chimera exhibited replication over several days in both the upper and lower counterparts, which transferred the major antigenic determinants, confers improved growth in chimpanzees whereas other BRSV genes contribute to a highly attenuated phenotype.

The animals which received rBRSV or rBRSV/A2 virus were challenged on day 30 with $10^4$ pfu per site of wild type HRSV administered intranasally and intratracheally (Table 3). Nasopharyngeal swabs and tracheal lavages were taken at 3, 5, 7, and 10 days following challenge, and the shed virus was assayed by plaque assay. Prior immunization with either virus modestly reduced disease symptoms during challenge. Although the chimeric virus exhibited improved growth in chimpanzees over BRSV due to the incorporation of human RSV sequences, the highly restricted nature of replication in the chimeric virus indicates that fine-tuning of this vaccine candidate will involve reducing attenuation for primates.

TABLE 3

Replication of wtRSV A2 challenge virus in chimpanzees previously inoculated with either rBRSV or rBRSV/A2[a]

| Chimp Identification No. | Virus used for immunization | Nasopharyngeal swab titer ($\log_{10}$pfu/ml) Day post-inoculation | | | | | | Tracheal lavage titer ($\log_{10}$pfu/ml) Day post-inoculation | | | | | Peak rhinorrhea score |
|---|---|---|---|---|---|---|---|---|---|---|---|---|---|
| | | 0 | 3 | 5 | 7 | 10 | Peak | 3 | 5 | 7 | 10 | Peak | |
| 95A016 | rBRSV | <0.7 | 3.7 | 4.1 | 1.0 | <0.7 | 4.1 | 5.2 | 6.0 | <0.7 | <0.7 | 6.0 | 1 |
| 95A018 | rBRSV | <0.7 | 3.8 | 3.0 | <0.7 | <0.7 | 3.8 | 2.0 | 4.5 | <0.7 | <0.7 | 4.5 | 1 |
| mean | | | | | | | 4.0 | | | | | 5.3 | 1.0 |
| 95A007 | rBRSV/A2 | <0.7 | 4.6 | 4.3 | 1.6 | <0.7 | 4.6 | 5.7 | 6.3 | 1.7 | <0.7 | 6.3 | 2 |
| 95A008 | rBRSV/A2 | <0.7 | 2.2 | 5.4 | 1.7 | <0.7 | 5.4 | 3.2 | 6.3 | 2.8 | <0.7 | 6.3 | 2 |
| mean | | | | | | | 5.0 | | | | | 6.3 | 2.0 |

[a] Each chimpanzee was challenged on day 30 with wtRSV A2 administered intranasally and intratracheally at a dose of $10^4$ pfu/ml in a 1.0 ml inoculum per site. Nasopharyngeal swab samples and tracheal lavage samples were collected on the indicated days.

Example V

Construction of a Chimeric BRSV/HRSV Containing the HRSV G and F Genes in a Promoter-Proximal Shifted Position The present example describes construction of an infectious rBRSV/HRSV chimera in which the HRSV G and F genes are substituted into a recombinant bovine RSV (rBRSV) background. The resulting human-bovine chimera contains two genes of HRSV, namely G and F, and eight genes from BRSV, namely NS1, NS2, N, P, M, SH, M2 and L. In addition to this basic substituted glycoprotein construction, the HRSV G and F genes were also shifted to a more promoter-proximal position in the rBRSV backbone, i.e., relative to a wild-type gene order position of the F and G genes in the RSV genome. More specifically, the F and G genes were moved from their usual location relative to the promoter, namely gene positions 7 and 8, respectively, to positions 1 and 2, respectively.

Complete infectious rBRSV was produced as above in which nucleotide substitutions were made to create unique NotI, SalI and XhoI sites at positions 67, 4,673 and 7,471, respectively (FIG. 10A) (Buchholz et al., J. Virol. 73:251-259, 1999; Buchholz et al., J. Virol. 74:1187-1199, 2000, incorporated herein by reference). The NotI site is contained within the upstream nontranslated region of the BRSV NS1 gene, and the SalI and XhoI sites are in intergenic regions. Digestion of the rBRSV antigenomic cDNA with SalI and XhoI excised the BRSV G and F genes in their entirety and created compatible cohesive ends that were ligated. This resulted in an rBRSV antigenomic cDNA lacking the G and F genes and containing a 64-nucleotide SH-M2 intergenic region with the following sequence: TTAAACTTAAAAATGGTTTATGtcgaG-GAATAAAATCGATTAACAACCAATCAT TCAAAAA-GAT (SEQ ID NO. 23) (the tetranucleotide cohesive ends of the original cleaved SalI and XhoI sites are in small case). For comparison, the naturally-occurring BRSV F-M2 intergenic sequence is 55 nucleotides in length.

A cDNA containing the HRSV G and F genes was prepared by PCR with mutagenic primers used to modify the cDNA ends. Specifically, PCR was used to amplify nucleotides 4692-7551 of the complete HRSV antigenomic cDNA (spanning from the ATG of the G ORF to the end of the F gene-end signal), and the primers were designed to add, immediately after the F gene-end signal, the first 6 nucleotides of the F-M2 IG followed by a copy of the NS1 gene-start signal. The PCR primers also were designed to add a BlpI site and an NotI site each on both ends of the cDNA. The sequence of the cDNA fragment that was subjected to PCR was confirmed by dideoxynucleotide sequencing. This cDNA was then inserted as a NotI fragment into the unique NotI site of the rBRSV antigenomic cDNA lacking the G and F genes as described above. A correct recombinant was identified by restriction fragment mapping, and was designated rBRSV/A2-G1 F2. The structure of the encoded genomic RNA is shown in FIG. 10C. As shown, in this cDNA the G and F genes were moved from positions 7 and 8 relative to the promoter to positions 1 and 2.

Figure 11:
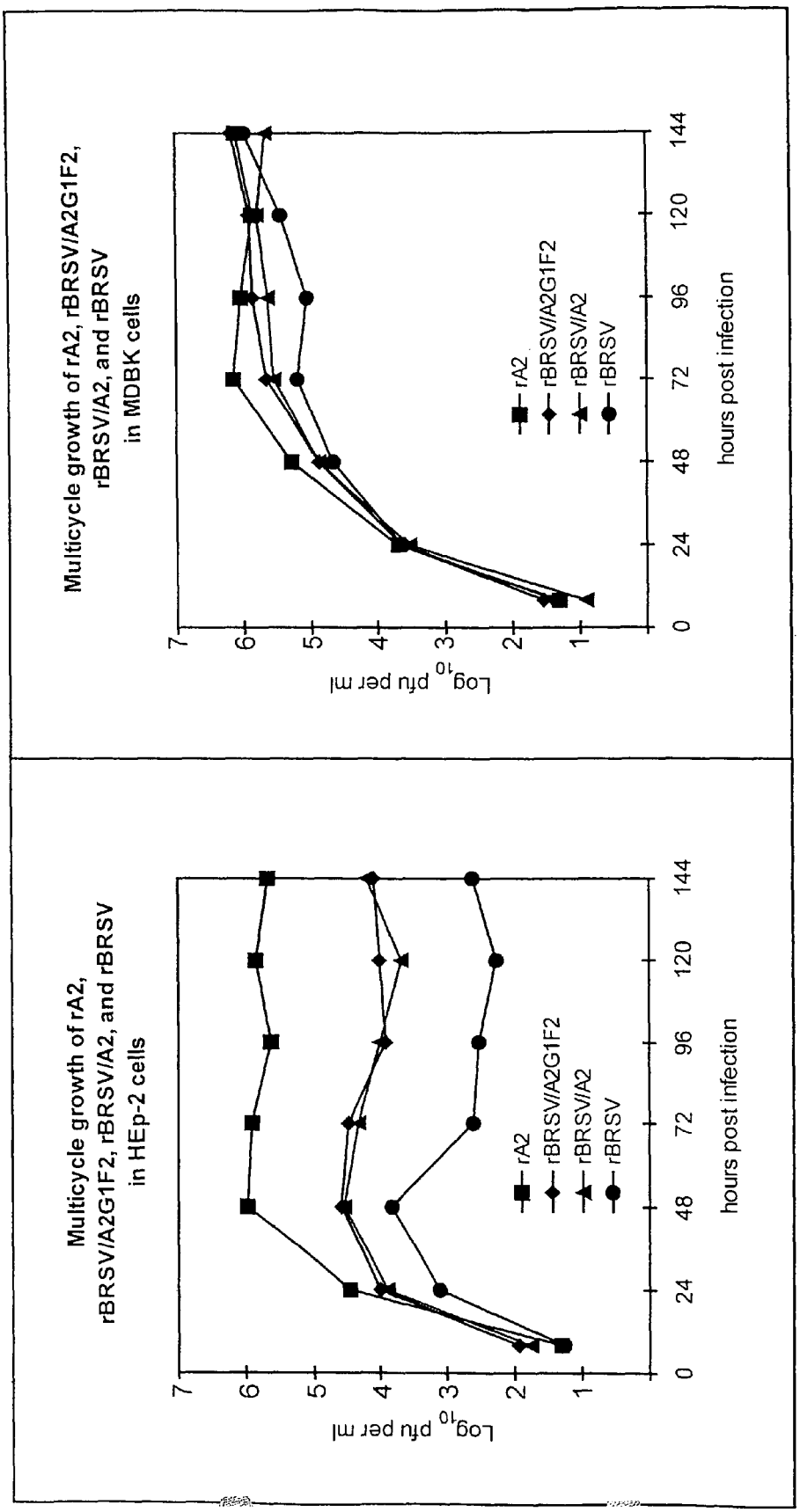
FIG. 11 depicts multicycle growth of RBRSV, rHRSV (rA2), rBRSV/A2, and rBRSV/A2-G1 F2 in HEp-2 human (left panel) and MDBK bovine (right panel) cells. Duplicate cell monolayers were infected with the indicated virus at an MOI of 0.1 and incubated at 37° C., and medium aliquots were harvested at the indicated times, flash frozen, stored at −70° C. and titrated later in duplicate. Each value is the mean titer of two wells.

A plasmid encoding the antigenomic RNA of rBRSV/A2-G1 F2 was transfected, together with plasmids encoding the N, P, M2-1 and L support proteins, into BSR T7/5 cells, which stably express the T7 RNA polymerase, as described above (see also, Buchholz et al., J. Virol. 73:251-259, 1999; Buchholz et al., J. Virol. 74:1187-1199, 2000, each incorporated herein by reference), and infectious virus was recovered. The recovered rBRSV/A2-G1F2 virus was compared to rBRSV, rHRSV (also called rA2) and rBRSV/A2 with regard to the efficiency of multicycle growth in human HEp-2 cells and bovine MDBK cells. As described above (see also, Buchholz et al, J. Virol. 74:1187-1199, 2000, incorporated herein by reference), rHRSV grows much more efficiently than rBRSV in HEp-2 cells, and the rBRSV/A2 virus grows with an efficiency intermediate between that of each parent. As shown in FIG. 11, the efficiency of replication of rBRSV/A2-G1F2 was indistinguishable from that of rBRSV/A2. Thus, unexpectedly, the change in the location of the G and F genes did not reduce the efficiency of growth in vitro, which novel result allows for efficient production of RSV vaccine virus.

Figure 12:
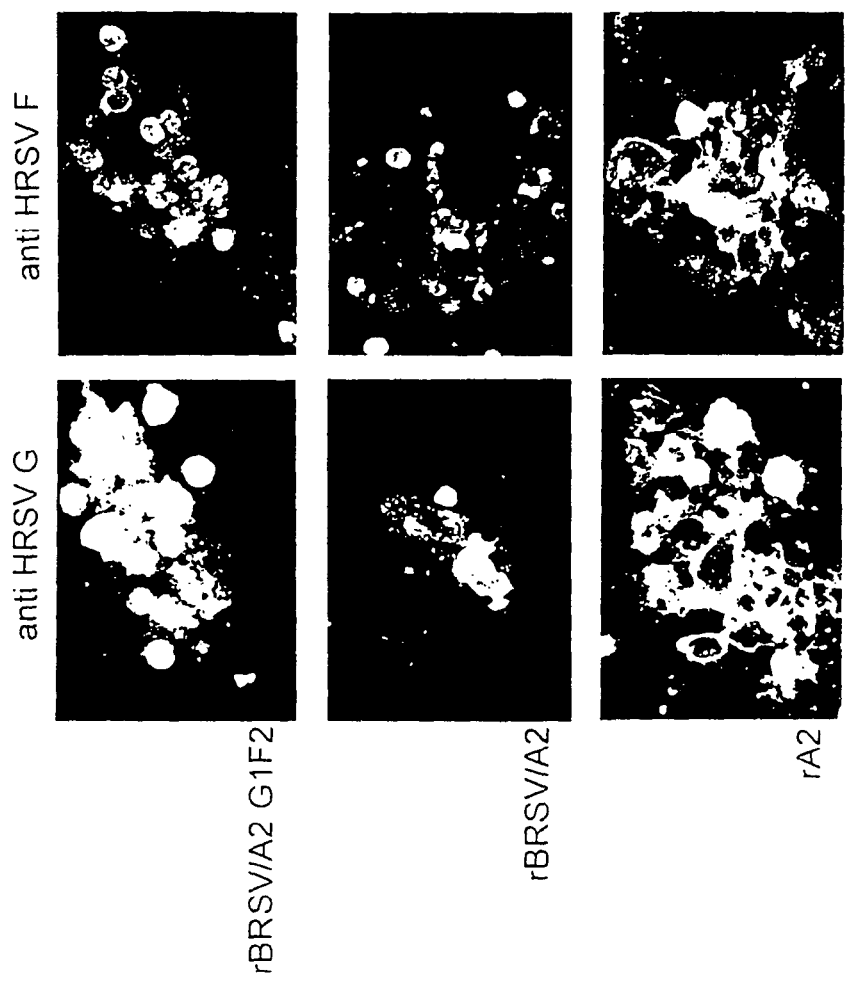
FIG. 12. shows indirect immunofluorescence of HEp-2 cells infected with rBRSV/A2-G1F2, rBRSV/A2, or rA2. Cells were infected at an MOI of 0.1, incubated at 37° C. for 96 hours, fixed with acetone, permeabilized and reacted with monoclonal antibody 021/1G, specific to the G protein of HRSV, or with monoclonal antibody 44F, specific to the F protein of HRSV. Antibody binding was visualized by reaction with a tagged antibody specific to murine IgG.

Immunofluorescence was performed on HEp-2 cells infected with wt HRSV or the chimeric viruses rBRSV/A2 or rBRSV/A2-G1F2. This was performed using two monoclonal antibodies specific to the HRSV G or F proteins, namely 021/01G and 44F, respectively (Lopez et al., J. Virol. 72:6922-6928, 1998; Melero et al., J. Gen. Virol. 78:2411-2418, 1997, each incorporated herein by reference). The staining was done with each monoclonal antibody individually. Although this assay is only semi-quantitative, it has been previously determined that the assay distinguishes reliably between wt rBRSV and rBRSV/A2 (the latter bearing the HRSV G and F genes in the normal genome location in the rBRSV backbone). In particular, wt HRSV gives a very strong, extensive pattern of immunofluorescence indicative of efficient and extensive antigen expression, while rBRSV/A2 gives a weaker, more diffuse, less extensive pattern (Buchholz et al., J. Virol. 74:1187-1199, 2000, incorporated herein by reference). A comparable assay conducted for rBRSV/A2-G1F2 (FIG. 12), shows that the pattern of immunofluorescence for this promoter-shifted chimeric virus was very similar to that of wt HRSV. This result is consistent with increased expression of the G and F glycoproteins. At the same time, the cytopathic effect associated with rBRSV/A2-G1F2 was reduced compared to wt HRSV, and more closely resembled that of rBRSV/A2 as described previously (Buchholz et al., *J. Virol.* 74:1187-1199, 2000, incorporated herein by reference). Specifically, rBRSV/A2 and rBRSV/A2-G1F2 induced fewer and smaller syncytia.

Thus, the present example documents modification of the rBRSV/A2 virus, which contains the genes for the major protective antigens of HRSV, the G and F proteins, in the background of BRSV which is strongly attenuated for replication in the respiratory tract of primates. As shown in the preceding example, the rBRSV/A2 virus has a strong host range restriction that renders it highly attenuated in primates. Since the present rBRSV/A2-G1F2 virus bears the same constellation of BRSV genes in its genetic background, it is likely to share this strong host range restriction phenotype, thereby increasing the expression of the two major protective antigens. The increased expression of these two protective antigens in vivo is further expected to increase the immunogenicity of this virus. Thus, the present example modified and improved the rBRSV/A2 virus by moving the HRSV genes to a promoter proximal location. A positional shift of this magnitude, i.e., where the G and F genes were moved from wild type positions 7 and 8 relative to the promoter to new positions 1 and 2, has not been described previously.

Example VI

Construction of a Chimeric BRSV/HRSV With Envelope-Associated M, G and F Proteins Derived From HRSV The present example demonstrates yet another human-bovine chimeric RSV which involves modification of an antigenic chimera virus resembling the rBRSV/A2 chimera (having the HRSV G and F protective antigen genes in a BRSV host-range-attenuated background), described above. Both BRSV and HRSV have 4 envelope-associated proteins: the G and F glycoproteins which are the major protective antigens; the small hydrophobic SH protein of unknown function which does not appear to be a neutralization or protective antigen for HRSV (Whitehead et al., *J. Virol.* 73:3438-3442, 1999; Connors et al., *J. Virol.* 65:1634-1637, 1991, each incorporated herein by reference); and the nonglycosylated internal matrix M protein, which is not a protective antigen but is important in virion assembly (Teng and Collins, *J. Virol.* 72:5707-16, 1998, incorporated herein by reference). In this example, a BRSV/HRSV chimeric virus was constructed in which all four BRSV envelope-associated protein genes were deleted, namely BRSV M, SH, G and F, and in which three HRSV envelope-associated protein genes, namely M, G and F, were inserted in their place. Although the HRSV SH gene was not included in this particular recombinant, the construct described in this example is designed so that SH can be readily added at its normal genome position or in other positions.

The previously-described rBRSV/A2 construct (Buchholz et al., *J. Virol.* 74:1187-1199, 2000, incorporated herein by reference) was modified to contain a unique MluI site at position 3204, within the intergenic region between the P and M genes (FIG. 13, panel A; P-M IG). This involved the introduction of 5 nucleotide substitutions. Nucleotide sequence position numbers are relative to the complete rBRSV antigenome (Buchholz et al., *J. Virol.* 73:251-259, 1999; Buchholz et al., *J. Virol.* 74:1187-1199, 2000; GenBank accession number AF092942 or complete rHRSV antigenome in Collins et al., *Proc. Natl. Acad. Sci. USA* 92:11563-11567, 1995; each incorporated herein by reference), and sequence position numbers that refer to the HRSV sequence are underlined. The MluI-SalI fragment was excised and replaced by the MluI-SalI fragment bearing the M gene.

Referring to FIG. 13, panel B, a cDNA containing the HRSV M gene was amplified and modified by PCR using primers that introduced changes to the ends of the cDNAs. Specifically, the M cDNA was modified so that its upstream end contained an MluI site, followed by the last nucleotide of the P-M intergenic region (which is the same in HRSV and BRSV), followed by the complete HRSV M gene, followed by the first 4 nucleotides of the BRSV SH-G intergenic region, followed by a SalI site. The sequence of this cDNA was confirmed to be correct in its entirety. It was digested with MluI and SalI and cloned into the MluI-SalI window of the rBRSV antigenome. This resulted in rBRSV/A2-MGF. As shown in FIG. 13, panel C, this chimera contained a backbone of six BRSV genes, namely NS1, NS2, N, P, M2 and L, and three HRSV envelope-associated protein genes, namely M, G and F.

This antigenomic plasmid was transfected, together with plasmids encoding the N, P, M2-1 and L support proteins, into BSR T7/5 cells, which stably express the T7 RNA polymerase, as described in detail previously (Buchholz et al., *J. Virol.* 73:251-259, 1999; Buchholz et al., *J. Virol.* 74:1187-1199, 2000, each incorporated herein by reference), and infectious virus was recovered.

The foregoing examples demonstrate novel compositions and methods for producing human-bovine chimeric RSV having suitable characteristics of growth, attenuation, immunogenicity and an ability to evoke a specific or multi-specific, protective immune response in susceptible hosts. In more detailed aspects, the foregoing examples demonstrate two extremes with regard to attenuation of chimeric human-bovine RSV bearing the major HRSV antigenic determinants, the G and F proteins. At one extreme is wt HRSV, which grows permissively in humans and chimpanzees and is virulent. At the other extreme is rBRSV/A2, which also bears the HRSV G and F antigenic determinants. This novel chimeric virus was constructed according to the methods of the invention and shown to be viable, safe and highly attenuated in chimpanzees.

The difference between wt HRSV and rBRSV/A2 is determined by 9 genes. In accordance with the teachings herein, stepwise replacement of BRSV genes with HRSV genes, for example into a rBRSV/A2 backbone, will yield candidate vaccine viruses with varying levels of attenuation. A critical aspect of the invention is that the major HRSV antigenic determinants have been shown to yield viable strains for vaccine development. The close correspondence between the HRSV and BRSV genomes, and the interchangeability of the transcription signals as demonstrated in these examples, simplifies gene swaps to practice additional aspects of the invention and develop vaccine strains having desired levels of attenuation. To simplify these methods, the swaps can be done with pairs of genes at a time.

As indicated by the examples herein, genes to be replaced in human-bovine chimeric RSV can be selected that are likely to interact functionally of structurally based on available knowledge of RSV structure/function. These exchanges and other modifications within human-bovine chimeric RSV are further simplified by the fact that proteins that interact are juxtaposed in the genome, for example the N and P nucleocapsid proteins, the M, SH, F and G envelope proteins, and the M2-1, M2-2 and L polymerase components. Thus, additional candidate vaccine strains according to the invention can be achieved, for example, by incorporating two or more juxtaposed genes, e.g., selected from N and P, two or more of the M, SH, F and G envelope genes, or two or more of the M2-1, M2-2 and L genes, together as a heterologous insert or substitution unit in a recipient or background genome or antigenome.

For example, the M and SH genes can be replaced together in rBRSV/A2 with their HRSV counterparts. This will result in a virus in which the viral envelope proteins (G, F, SH and M) are all of HRSV, while the internal proteins are of BRSV. This can be followed, as needed, by replacement of additional BRSV genes with their human counterparts, for example, N and P as another pair, NS1 and NS2 as another, and M2-1, M2-2 and L as another group. The juxtaposition of each pair of genes will simplify the substitutions. At the same time, the converse approach of inserting individual BRSV genes into HRSV, leaving the HRSV G and F antigenic determinants undisturbed, will also yield desired vaccine candidates within the invention. For example, one or more of the N, P, M2-1 and M genes of a human RSV can be individually replaced by their bovine counterparts. Recovered recombinant viruses are then evaluated for the attenuation phenotype in cell culture, rodents, and nonhuman primates, as exemplified herein. In this manner, the invention provides for identification of candidate human-bovine chimeric RSV vaccine viruses having desired levels of attenuation and protective efficacy for treatment and prophylaxis of RSV in various subjects.

Microorganism Deposit Information

The following materials have been deposited with the American Type Culture Collection, 10801 University Boulevard, Manassas, Va. 20110-2209, under the conditions of the Budapest Treaty and designated as follows:

| Plasmid | Accession No. | Deposit Date |
| --- | --- | --- |
| cpts RSV 248 | ATCC VR 2450 | Mar. 22, 1994 |
| cpts RSV 248/404 | ATCC VR 2454 | Mar. 22, 1994 |
| cpts RSV 248/955 | ATCC VR 2453 | Mar. 22, 1994 |
| cpts RSV 530 | ATCC VR 2452 | Mar. 22, 1994 |
| cpts RSV 530/1009 | ATCC VR 2451 | Mar. 22, 1994 |
| cpts RSV 530/1030 | ATCC VR 2455 | Mar. 22, 1994 |
| RSV B-1 cp52/2B5 | ATCC VR 2542 | Sep. 26, 1996 |
| RSV B-1 cp-23 | ATCC VR 2579 | Jul. 15, 1997 |
| p3/7(131) | ATCC 97990 | Apr. 18, 1997 |
| p3/7(131)2G | ATCC 97989 | Apr. 18, 1997 |
| p218(131) | ATCC 97991 | Apr. 18, 1997 |

What is claimed is:

1. An infectious chimeric respiratory syncytial virus (RSV) comprising a major nucleocapsid (N) protein, a nucleocapsid phosphoprotein (P), a large polymerase protein (L), a RNA polymerase elongation factor (M2ORF1), and a partial or complete human-bovine chimeric RSV genome or antigenome comprising a RSV background genome or antigenome of a bovine RSV wherein human RSV glycoprotein genes F and G are substituted to replace the counterpart F and G glycoprotein genes in said partial bovine RSV background genome or antigenome and wherein said human RSV glycoprotein genes F and G are substituted at a position that is more promoter-proximal as compared to the position of said glycoprotein genes F and G in a wild type bovine RSV genome or antigenome.

2. The chimeric RSV of claim 1, wherein the chimeric genome or antigenome further incorporates at least one and up to a full complement of attenuating mutations present within a panel of mutant human RSV strains, said panel comprising cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579).

3. The chimeric RSV of claim 1, wherein the chimeric genome or antigenome incorporates at least one and up to a full complement of attenuating mutations specifying an amino acid substitution at Val267 in the RSV N gene, Glu218 and/or Thr523 in the RSV F gene, Asn43, Cys319, Phe 521, Gln831, Met1169, Tyr1321 and/or His 1690 in the RSV polymerase gene L, and a nucleotide substitution in the gene-start sequence of gene M2.

4. The chimeric RSV of claim 1, wherein the chimeric genome or antigenome further comprises a polynucleotide encoding a non-RSV molecule selected from a cytokine, a T-helper epitope, a restriction site marker, or a protein of a microbial pathogen capable of eliciting a protective immune response in a mammalian host.

5. The chimeric RSV of claim 1, wherein the chimeric genome or antigenome further comprises one or more gene(s) and/or genome segment(s) from parainfluenza virus (PIV).

6. The chimeric RSV of claim 1, wherein the chimeric genome or antigenome further comprises one or more genes or genome segments from measles virus.

7. The chimeric RSV of claim 1 that is a subviral particle.

* * * * *

SEQUENCE LISTING

```
<160> NUMBER OF SEQ ID NOS: 23

<210> SEQ ID NO 1
<211> LENGTH: 80
<212> TYPE: DNA
<213> ORGANISM: Bovine respiratory syncytial virus

<400> SEQUENCE: 1
agttatttaa aattaaactt aaaaatggtt tatggttaca tacagatgtt ggggcaaata      60
caagtatgtc caaccatacc                                                 80

<210> SEQ ID NO 2
<211> LENGTH: 80
<212> TYPE: DNA
<213> ORGANISM: Artificial Sequence
<220> FEATURE:
<223> OTHER INFORMATION: Synthetic bovine RSV

<400> SEQUENCE: 2
agttatttaa aattaaactt aaaaatggtt tatgtcgaca tacagatgtt ggggcaaata      60
caagtatgtc caaccatacc                                                 80

<210> SEQ ID NO 3
<211> LENGTH: 70
<212> TYPE: DNA
<213> ORGANISM: Artificial Sequence
<220> FEATURE:
<223> OTHER INFORMATION: Synthetic human and bovine RSV

<400> SEQUENCE: 3
agttatttaa aattaaactt aaaaatggtt tatgtcgact ggggcaaatg caaacatgtc      60
caaaaacaag                                                            70

<210> SEQ ID NO 4
<211> LENGTH: 87
<212> TYPE: DNA
<213> ORGANISM: Human respiratory syncytial virus
```

-continued

```
<400> SEQUENCE: 4
agttaattaa aaatagtcat aacaatgaac taggatatca agactaacaa taacattggg    60
gcaaatgcaa acatgtccaa aaacaag                                       87

<210> SEQ ID NO 5
<211> LENGTH: 62
<212> TYPE: DNA
<213> ORGANISM: Bovine respiratory syncytial virus

<400> SEQUENCE: 5
agttatttaa aaagatatgt ataattcact aattaaaact ggggcaaata aggatggcga    60
ca                                                                  62

<210> SEQ ID NO 6
<211> LENGTH: 62
<212> TYPE: DNA
<213> ORGANISM: Artificial Sequence
<220> FEATURE:
<223> OTHER INFORMATION: Synthetic bovine RSV

<400> SEQUENCE: 6
agttatttaa aaagatatgc atgcttcact aattaaaact ggggcaaata aggatggcga    60
ca                                                                  62

<210> SEQ ID NO 7
<211> LENGTH: 87
<212> TYPE: DNA
<213> ORGANISM: Artificial Sequence
<220> FEATURE:
<223> OTHER INFORMATION: Synthetic human and bovine RSV

<400> SEQUENCE: 7
agttacttaa aaacatatta tcacaaaagg ccttgaccaa cttaaacaga atcaaaataa    60
actctggggc aaataacaat ggagttg                                       87

<210> SEQ ID NO 8
<211> LENGTH: 87
<212> TYPE: DNA
<213> ORGANISM: Human respiratory syncytial virus

<400> SEQUENCE: 8
agttacttaa aaacatatta tcacaaaaag ccatgaccaa cttaaacaga atcaaaataa    60
actctggggc aaataacaat ggagttg                                       87

<210> SEQ ID NO 9
<211> LENGTH: 87
<212> TYPE: DNA
<213> ORGANISM: Bovine respiratory syncytial virus

<400> SEQUENCE: 9
ccatgttgat agttatataa aaatattata ttagtctcaa agaataaaat tatttaacaa    60
ccaatcattc aaaaagatgg ggcaaat                                       87

<210> SEQ ID NO 10
<211> LENGTH: 87
<212> TYPE: DNA
<213> ORGANISM: Artificial Sequence
<220> FEATURE:
<223> OTHER INFORMATION: Synthetic bovine RSV
```

```
<400> SEQUENCE: 10
ccatgttgat agttatataa aaatattata ttagtctcga ggaataaaat cgattaacaa      60
ccaatcattc aaaaagatgg ggcaaat                                         87

<210> SEQ ID NO 11
<211> LENGTH: 74
<212> TYPE: DNA
<213> ORGANISM: Artificial Sequence
<220> FEATURE:
<223> OTHER INFORMATION: Synthetic human and bovine RSV

<400> SEQUENCE: 11
cctagtttat agttatataa aactcgagga ataaaatcga ttaacaacca atcattcaaa      60
aagatggggc aaat                                                       74

<210> SEQ ID NO 12
<211> LENGTH: 77
<212> TYPE: DNA
<213> ORGANISM: Human respiratory syncytial virus

<400> SEQUENCE: 12
cctagtttat agttatataa aacacaattg aatgccagat taacttacca tctgtaaaaa      60
tgaaaactgg ggcaaat                                                    77

<210> SEQ ID NO 13
<211> LENGTH: 46
<212> TYPE: DNA
<213> ORGANISM: Artificial Sequence
<220> FEATURE:
<223> OTHER INFORMATION: Synthetic human bovine RSV

<400> SEQUENCE: 13
agttatttaa aaagatatgc atgcggggca aataacaatg gagttg                    46

<210> SEQ ID NO 14
<211> LENGTH: 55
<212> TYPE: DNA
<213> ORGANISM: Artificial Sequence
<220> FEATURE:
<223> OTHER INFORMATION: Synthetic respiratory syncytial virus

<400> SEQUENCE: 14
ggggcaaata caagttaatt cgcggccgcc ccctctcttc tttctacaga aaatg          55

<210> SEQ ID NO 15
<211> LENGTH: 35
<212> TYPE: DNA
<213> ORGANISM: Artificial Sequence
<220> FEATURE:
<223> OTHER INFORMATION: Synthetic respiratory syncytial virus

<400> SEQUENCE: 15
gcggccgcta aatttaactc ccttgcttag cgatg                                35

<210> SEQ ID NO 16
<211> LENGTH: 29
<212> TYPE: DNA
<213> ORGANISM: Artificial Sequence
<220> FEATURE:
<223> OTHER INFORMATION: Synthetic respiratory syncytial virus

<400> SEQUENCE: 16
cacaatgggg caaataagct tagcggccg                                       29
```

<210> SEQ ID NO 17
<211> LENGTH: 24
<212> TYPE: DNA
<213> ORGANISM: Artificial Sequence
<220> FEATURE:
<223> OTHER INFORMATION: Synthetic respiratory syncytial virus

<400> SEQUENCE: 17
agttagtaaa aataaagacg cgtt                                          24

<210> SEQ ID NO 18
<211> LENGTH: 29
<212> TYPE: DNA
<213> ORGANISM: Artificial Sequence
<220> FEATURE:
<223> OTHER INFORMATION: Synthetic respiratory syncytial virus

<400> SEQUENCE: 18
ttatgtcgac tggggcaaat gcaaacatg                                     29

<210> SEQ ID NO 19
<211> LENGTH: 28
<212> TYPE: DNA
<213> ORGANISM: Artificial Sequence
<220> FEATURE:
<223> OTHER INFORMATION: Synthetic respiratory syncytial virus

<400> SEQUENCE: 19
ggggcaaata acaatggagt tgccaatc                                      28

<210> SEQ ID NO 20
<211> LENGTH: 29
<212> TYPE: DNA
<213> ORGANISM: Artificial Sequence
<220> FEATURE:
<223> OTHER INFORMATION: Synthetic respiratory syncytial virus

<400> SEQUENCE: 20
tttttatata actataaact aggaatcta                                     29

<210> SEQ ID NO 21
<211> LENGTH: 42
<212> TYPE: DNA
<213> ORGANISM: Artificial Sequence
<220> FEATURE:
<223> OTHER INFORMATION: Synthetic respiratory syncytial virus

<400> SEQUENCE: 21
aggaattcgc atgcggggca aataacaatg gagttgccaa tc                      42

<210> SEQ ID NO 22
<211> LENGTH: 43
<212> TYPE: DNA
<213> ORGANISM: Artificial Sequence
<220> FEATURE:
<223> OTHER INFORMATION: Synthetic respiratory syncytial virus

<400> SEQUENCE: 22
aggaattctc gagtttttat ataactataa actaggaatc tac                     43

<210> SEQ ID NO 23
<211> LENGTH: 64
<212> TYPE: DNA
<213> ORGANISM: Artificial Sequence
<220> FEATURE:

```
<223> OTHER INFORMATION: Synthetic respiratory syncytial virus

<400> SEQUENCE: 23
ttaaacttaa aaatggttta tgtcgaggaa taaaatcgat taacaaccaa tcattcaaaa      60
agat                                                                  64
```